United States Patent
Jatsch et al.

(10) Patent No.: US 9,515,266 B2
(45) Date of Patent: Dec. 6, 2016

(54) MATERIALS FOR ORGANIC ELECTROLUMINESCENT DEVICES

(71) Applicant: Merck Patent GmbH, Darmstadt (DE)

(72) Inventors: Anja Jatsch, Frankfurt am Main (DE); Rémi Manouk Anémian, Seoul (KR); Bernd Schroeder, Villmar-Weyer (DE); Arne Buesing, Frankfurt am Main (DE); Philipp Stoessel, Frankfurt am Main (DE); Christof Pflumm, Darmstadt (DE); Jonas Valentin Kroeber, Frankfurt am Main (DE); Thomas Eberle, Landau (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/352,709

(22) PCT Filed: Sep. 24, 2012

(86) PCT No.: PCT/EP2012/003981
§ 371 (c)(1),
(2) Date: Apr. 18, 2014

(87) PCT Pub. No.: WO2013/056776
PCT Pub. Date: Apr. 25, 2013

(65) Prior Publication Data
US 2014/0275530 A1  Sep. 18, 2014

(30) Foreign Application Priority Data
Oct. 20, 2011 (EP) .................................. 11008426

(51) Int. Cl.
*C07D 209/56* (2006.01)
*H01L 51/00* (2006.01)
*C07D 495/04* (2006.01)
*C07D 209/94* (2006.01)

(52) U.S. Cl.
CPC ......... *H01L 51/0054* (2013.01); *C07D 209/94* (2013.01); *C07D 495/04* (2013.01); *H01L 51/0058* (2013.01); *H01L 51/0061* (2013.01); *H01L 51/0067* (2013.01); *H01L 51/0071* (2013.01); *H01L 51/0072* (2013.01); *H01L 51/0074* (2013.01)

(58) Field of Classification Search
CPC .................................................. C07D 209/56
See application file for complete search history.

(56) References Cited

U.S. PATENT DOCUMENTS

| | | |
|---|---|---|
| 2012/0068170 A1 | 3/2012 | Pflumm et al. |
| 2012/0097899 A1 | 4/2012 | Parham et al. |
| 2013/0060037 A1 | 3/2013 | Lin et al. |
| 2013/0285036 A1 | 10/2013 | Stoessel et al. |
| 2014/0054564 A1 | 2/2014 | Kim et al. |

FOREIGN PATENT DOCUMENTS

| | | |
|---|---|---|
| EP | 2599851 A2 | 6/2013 |
| JP | 2012140365 A | 7/2012 |
| JP | 2013539206 A | 10/2013 |
| KR | 2009-0065201 A | 6/2009 |
| KR | 2011-0043270 A | 4/2011 |
| WO | WO-2010083359 A2 | 7/2010 |
| WO | WO-2010107244 A2 | 9/2010 |
| WO | WO-2010136109 A1 | 12/2010 |
| WO | WO-2011000455 A1 | 1/2011 |
| WO | WO-2012095143 A1 | 7/2012 |

OTHER PUBLICATIONS

International Search Report for PCT/EP2012/003981 mailed Nov. 19, 2012.

*Primary Examiner* — Brian McDowell
(74) *Attorney, Agent, or Firm* — Drinker Biddle & Reath LLP

(57) ABSTRACT

Triphenylene derivatives, in particular for use as triplet matrix materials in organic electroluminescent devices, one of example of which is represented by formula 1. The invention furthermore relates to a process for the preparation of the triphenylene derivatives and to electronic devices comprising the triphenylene derivatives.

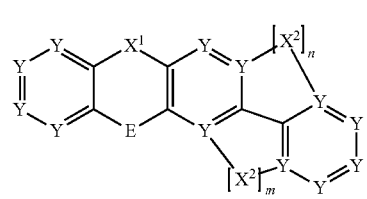

Formula (1)

19 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. §371) of PCT/EP2012/003981, filed Sep. 24, 2012, which claims benefit of European Application No. 11008426.6, filed Oct. 20, 2011, both of which are incorporated herein by reference in their entirely.

The present invention describes triphenylene derivatives, in particular for use as triplet matrix materials in organic electroluminescent devices. The invention furthermore relates to a process for the preparation of the compounds according to the invention and to electronic devices comprising same.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are frequently organometallic complexes, which exhibit phosphorescence instead of fluorescence (M. A. Baldo et al., Appl. Phys. Lett. 1999, 75, 4-6). For quantum-mechanical reasons, an up to four-fold energy and power efficiency is possible using organometallic compounds as phosphorescence emitters. In general, there is still a need for improvement, for example with respect to efficiency, operating voltage and lifetime, in the case of OLEDs, in particular also in the case of OLEDs which exhibit triplet emission (phosphorescence).

The properties of phosphorescent OLEDs are not determined only by the triplet emitters employed. In particular, the other materials used, such as, for example, matrix materials or hole-blocking materials, are also of particular importance here. Improvements in these materials can thus also result in significant improvements in the OLED properties.

In accordance with the prior art, indolocarbazole derivatives (for example in accordance with WO 2007/063754 or WO 2008/056746) or indenocarbazole derivatives (for example in accordance with WO 2010/136109 or WO 2011/000455), in particular those which are substituted by electron-deficient heteroaromatic compounds, such as triazine, are used, inter alia, as matrix materials for phosphorescent emitters. Furthermore, for example, triphenylene derivatives (for example in accordance with JP 2006/143845 or WO 2006/047119) are used as matrix materials for phosphorescent emitters. However, there is still a need for improvement on use of these matrix materials, in particular with respect to the efficiency, the lifetime and the operating voltage of the device.

The object of the present invention is the provision of compounds which are suitable for use in a fluorescent or, in particular, in a phosphorescent OLED, for example as matrix material or as electron-transport or hole-blocking material. In particular, the object of the present invention is to provide matrix materials which are also suitable for red- and green- and optionally also for blue-phosphorescent OLEDs and which result in good efficiency, a long lifetime and low operating voltage. In particular, the properties of the matrix materials have a significant influence the lifetime and efficiency of the organic electroluminescent device.

Surprisingly, it has been found that electroluminescent devices which comprise compounds of the following formula (1), formula (2) or formula (3) have improvements over the prior art, in particular on use as matrix materials for phosphorescent dopants, but also on use as electron-transport or as hole-blocking compounds.

The present invention therefore relates to a compound of the following formula (1), formula (2), formula (3) or formula (4),

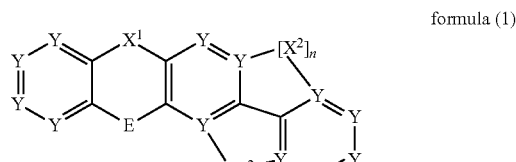

formula (1)

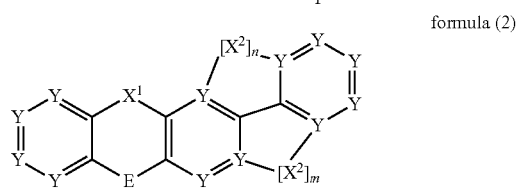

formula (2)

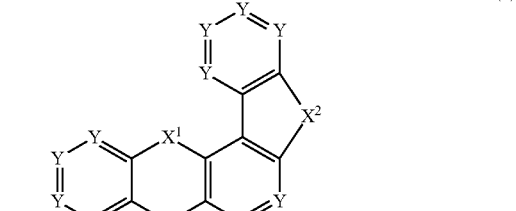

formula (3)

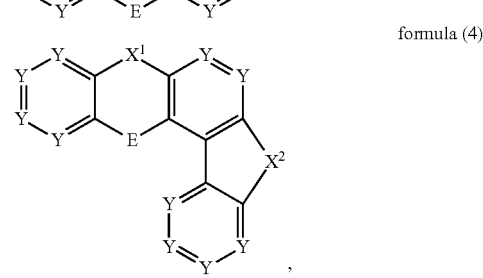

formula (4)

where the following applies to the symbols and indices used:

Y is C if a group $X^2$ is bonded to this group Y, or is on each occurrence, identically or differently, CR or N if no group $X^2$ is bonded to this group Y;

E is a single bond or a divalent bridge selected from $N(R^1)$, $B(R^1)$, $C(R^1)_2$, O, $Si(R^1)_2$, $C=NR^1$, $C=C(R^1)_2$, S, S=O, $SO_2$, $P(R^1)$ and $P(=O)R^1$;

$X^1$, $X^2$ is on each occurrence, identically or differently, a divalent bridge selected from $N(R^1)$, $B(R^1)$, O, $C(R^1)_2$, $Si(R^1)_2$, $C=NR^1$, $C=C(R^1)_2$, S, S=O, $SO_2$, $P(R^1)$ and $P(=O)R^1$; with the proviso that $X^1$ and $X^2$ do not simultaneously stand for O;

R, $R^1$ is on each occurrence, identically or differently, H, D, F, Cl, Br, I, $N(R^2)_2$, $N(Ar)_2$, $C(=O)Ar$, $P(=O)Ar_2$, $S(=O)Ar$, $S(=O)_2Ar$, $CR^2=CR^2Ar$, CN, $NO_2$, $Si(R^2)_3$, $B(OR^2)_2$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by $R^2C=CR^2$, $C\equiv C$, $Si(R^2)_2$, C=O, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals R², or an aryloxy or heteroaryloxy group having 5 to 40 aromatic ring atoms, which may in each case be substituted by one or more radicals R², or an aralkyl or heteroaralkyl group having 5 to 40 aromatic ring atoms, which may in each case be substituted by one or more radicals R², or a combination of these systems; two or more substituents R here together with the atoms to which they are bonded, or two substituents R¹ together with the atom to which they are bonded, may also form a mono- or polycyclic, aliphatic or aromatic ring system with one another;

Ar is on each occurrence, identically or differently, an aromatic or heteroaromatic ring system, preferably an aryl or heteroaryl group having 5 to 40 ring atoms, which may be substituted by one or more radicals R³;

R² is on each occurrence, identically or differently, H, D, F, Cl, Br, I, N(R³)₂, N(Ar)₂, C(=O)Ar, P(=O)Ar₂, S(=O)Ar, S(=O)₂Ar, CR³=CR³Ar, CN, NO₂, Si(R³)₃, B(OR³)₂, OSO₂R³, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals R³, where one or more non-adjacent CH₂ groups may be replaced by R³C=CR³, C≡C, Si(R³)₂, C=O, C=NR³, P(=O)(R³), SO, SO₂, NR³, O, S or CONR³ and where one or more H atoms may be replaced by D, F, Cl, Br, I, CN or NO₂, or an aromatic or heteroaromatic ring system having 5 to 60 aromatic ring atoms, which may in each case be substituted by one or more radicals R³, or an aryloxy or heteroaryloxy group having 5 to 40 aromatic ring atoms, which may be substituted by one or more radicals R³, or an aralkyl or heteroaralkyl group having 5 to 40 aromatic ring atoms, which may be substituted by one or more radicals R³, or a combination of these systems;

R³ is on each occurrence, identically or differently, H, D or an aliphatic hydrocarbon radical having 1 to 20 C atoms or an aryl or heteroaryl group having 5 to 40 ring atoms or a combination of these groups;

n, m are, identically or differently on each occurrence, 0 or 1, with the proviso that n+m=1 or 2;

characterised in that at least one group R and/or R¹ is present which stands for a group of the following formula (5),

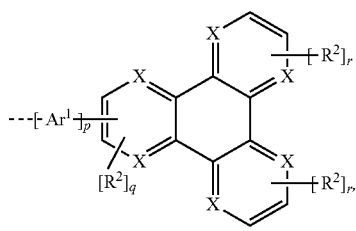

formula (5)

where the dashed bond indicates the linking of the group of the formula (5), R² has the meanings given above and furthermore:

X is C if the group Ar¹ or the remainder of the molecule is bonded to this X, and is on each occurrence, identically or differently, CR² or N in the other cases;

Ar¹ is a divalent aromatic or heteroaromatic ring system having 5 to 40 aromatic ring atoms, which may be substituted by one or more radicals R²;

p is on each occurrence, identically or differently, 0 or 1;

q, r is on each occurrence, identically or differently, 0, 1 or 2.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, etc. Aromatic rings linked to one another by a single bond, such as, for example, biphenyl, are, by contrast, not referred to as an aryl or heteroaryl group, but instead as an aromatic ring system.

An aromatic ring system in the sense of this invention contains 6 to 80 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, a C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are connected, for example, by a short alkyl group. Furthermore, aromatic rings linked to one another by a single bond, such as, for example, biphenyl, are referred to as an aromatic ring system in the sense of this application.

For the purposes of the present invention, an aliphatic hydrocarbon radical or an alkyl group or an alkenyl or alkynyl group, which may typically contain 1 to 40 or also 1 to 20 C atoms and in which, in addition, individual H atoms or CH₂ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkenyl, alkynyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, further preferably F or CN, particularly preferably CN.

An aromatic or heteroaromatic ring system having 5-80 aromatic ring atoms, which may also in each case be substituted by the above-mentioned radicals and which may be linked via any desired positions on the aromatic or heteroaromatic group, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combination of these systems. These groups may each be substituted by the above-mentioned radicals.

Preference is given to the compounds of the formula (1) or formula (2), very particular preference is given to the compounds of the formula (1).

Preference is furthermore given to compounds in which n+m=1.

In a preferred embodiment of the compounds according to the invention, E is selected from a single bond or a divalent bridge selected from $N(R^1)$, $C(R^1)_2$ and O. E is particularly preferably selected from a single bond, $N(R^1)$ or $C(R^1)_2$. E very particularly preferably stands for a single bond.

In a further preferred embodiment of the compounds according to the invention, $X^1$ is selected from the group consisting of $NR^1$ or S. X' particularly preferably stands for $NR^1$.

In a further preferred embodiment of the compounds according to the invention, $X^2$ is selected from the group consisting of $C(R^1)_2$, $NR^1$ or S, particularly preferably $C(R^1)_2$ or $NR^1$, very particularly preferably $C(R^1)_2$.

In a particularly preferred embodiment of the compounds according to the invention, $X^1$ stands for $N(R^1)$, and $X^2$ stands for $C(R^1)_2$. E particularly preferably simultaneously stands for a single bond.

If E, $X^1$ and/or $X^2$ stand for a group $NR^1$, $R^1$ then preferably stands for an aromatic or heteroaromatic ring system having 5 to 60 aromatic ring atoms, preferably having 6 to 24 aromatic ring atoms, which may also be substituted by one or more radicals $R^2$.

If E, $X^1$ and/or $X^2$ stand for a group $C(R^1)_2$, $R^1$ then preferably stands for a straight-chain alkyl group having 1 to 20 C atoms or a branched or cyclic alkyl group having 3 to 20 C atoms, each of which may be substituted by one or more radicals $R^2$, where one or more non-adjacent $CH_2$ groups may be replaced by $R^2C=CR^2$, $C\equiv C$, $Si(R^2)_2$, $C=O$, O, S or $CONR^2$ and where one or more H atoms may be replaced by D, F or CN, or an aromatic or heteroaromatic ring system having 5 to 60 aromatic ring atoms, which may also be substituted by one or more radicals $R^2$.

In a further preferred embodiment of the invention, Y stands for C if a group $X^2$ is bonded to this group Y, or stands, identically or differently on each occurrence, for CR if no group $X^2$ is bonded to this group Y.

In a further preferred embodiment, X stands for $CR^2$, or X stands for C if the group $Ar^1$ or the remainder of the molecule is bonded to this X.

Preferred embodiments of the compounds of the formula (1), (2), (3) or (4) are the compounds of the following formulae (1a), (2a), (3a) and (4a),

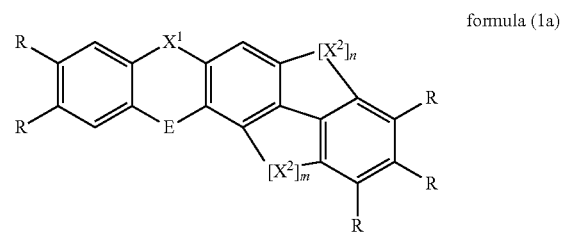

formula (1a)

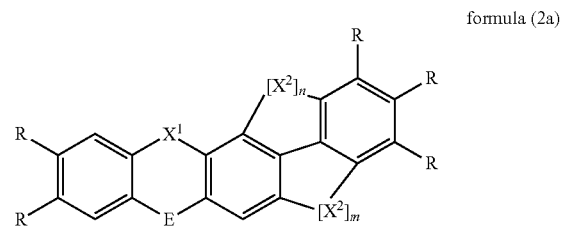

formula (2a)

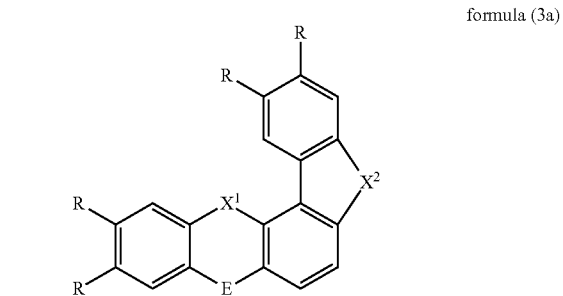

formula (3a)

-continued

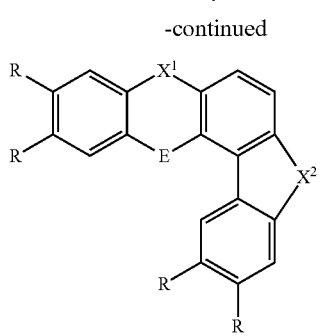
formula (4a)

where the symbols and indices used have the meanings given above. In particular, the symbols used have the preferred meanings given above.

Particular preference is given to structures in which $X^1$ stands for $NR^1$. Particular preference is therefore given to the structures of the following formulae (1b) to (4b),

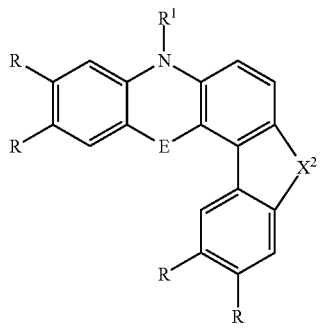

where the symbols and indices used have the meanings given above, in particular the preferred meanings given above.

In a particularly preferred embodiment of the invention, the compound of the formula (1) is selected from the following general structures (1b) to (1i):

formula (1b)
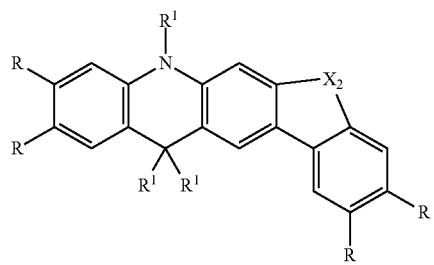

formula (1c)
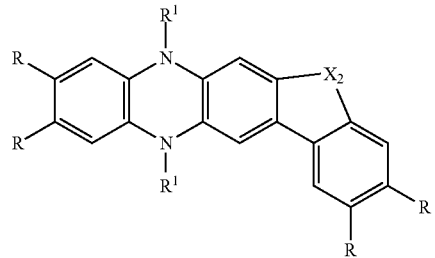

formula (1d)
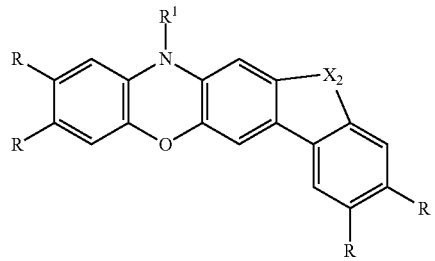

formula (1e)
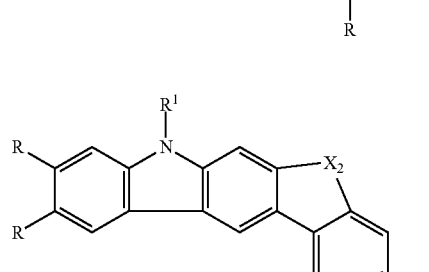

formula (1f)
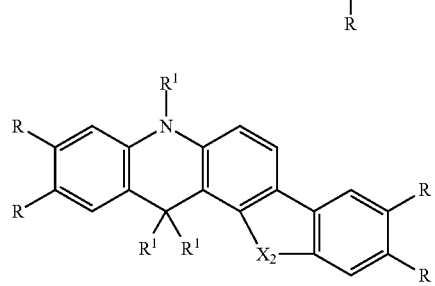
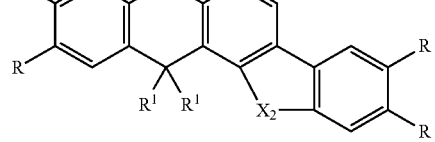

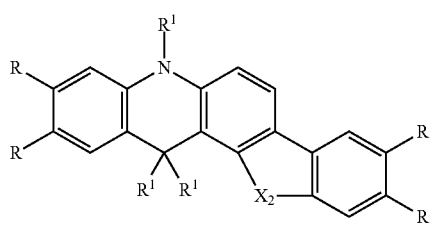
formula (1g)

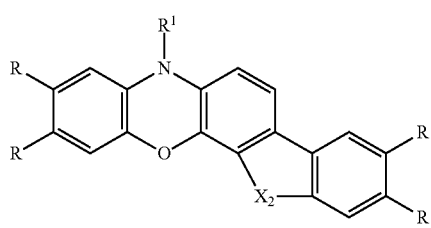
formula (1h)

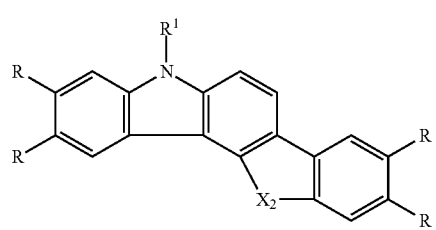
formula (1i)

where the symbols and indices have the meanings indicated above and where $X^2$ is preferably selected from $C(R^1)_2$, $N(R^1)$, O and S. Two radicals $R^1$ here which are bonded to the same C atom may also, together with the atom to which they are bonded, form an aliphatic, aromatic or heteroaromatic ring system, for example a fluorene.

In the formulae (1b) to (1i), $X^2$ particularly preferably stands for $NR^1$ or $C(R^1)_2$, very particularly preferably for $C(R^1)_2$.

As described above, the compound according to the invention contains at least one group R or $R^1$ of the formula (5). In a preferred embodiment of the invention, at least one group $X^1$ and/or $X^2$ stands for $NR^1$, where the group $R^1$ stands for a group of the formula (5). In a further preferred embodiment of the invention, at least one group R stands for a group of the formula (5).

In a further preferred embodiment of the invention, the compound of the formula (1), formula (2), formula (3) or formula (4) contains one, two or three groups of the formula (5), particularly preferably one or two groups of the formula (5), very particularly preferably precisely one group of the formula (5).

In a further preferred embodiment of the compounds according to the invention, the group of the formula (5) is a group of the following formula (5a),

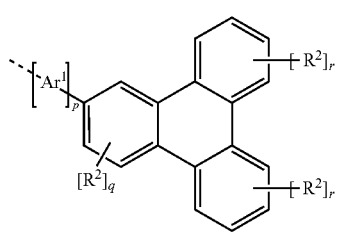
formula (5a)

where the symbols and indices used have the meanings given above, i.e. the triphenylene unit is bonded via the 2-position.

In a preferred embodiment of the formula (5a), the index q=0 and the index r is, identically or differently on each occurrence, 0 or 1, particularly preferably 0.

Preferred embodiments of the formula (5a) are therefore the structures of the following formula (5b) and particularly preferred embodiments are the structures of the following formula (5c),

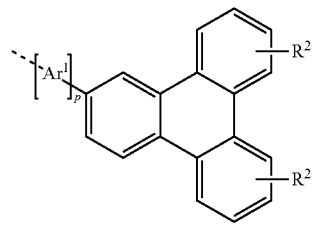
formula (5b)

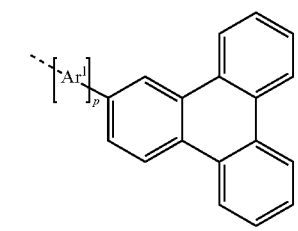
formula (5c)

where the symbols and indices used have the meanings given above.

In the groups of the formula (5) or (5a) to (5c), $Ar^1$ preferably stands for a divalent aromatic or heteroaromatic ring system having 6 to 24 aromatic ring atoms, which preferably contains no condensed aryl or heteroaryl group having more than two six-membered rings condensed directly onto one another. Preferred groups $Ar^1$ are selected from the group consisting of ortho-, meta- or para-phenylene, ortho-, meta- or para-biphenyl, ortho-, meta- or para-terphenyl, ortho-, meta- or para-quaterphenyl, furan, benzofuran, dibenzofuran, pyrrole, indole, carbazole or dibenzothiophene.

The above-mentioned embodiments of the invention can be combined with one another as desired. In particular, the general formulae (1), (2), (3) and (4) shown above or the preferred embodiments can be combined as desired with the formulae (5a) and (5b) and (5c) and with the above-mentioned preferred embodiments of the other symbols and indices. In a preferred embodiment of the invention, a plurality or all of the preferences given above occur simultaneously.

If one or more radicals R which are not equal to H or D and which do not stand for a group of the formula (4) are present in the compound of the general formula (1) to (4), these radicals are preferably selected from the group consisting of $N(Ar)_2$, preferably diphenylamino, a substituted or unsubstituted arylamine, a straight-chain alkyl group having 1 to 20 C atoms, preferably 1 to 10 C atoms, a branched alkyl group having 3 to 20 C atoms, preferably 1 to 10 C atoms, or an aromatic or heteroaromatic ring system having 5 to 40 ring atoms, which may be substituted by one or more radicals $R^2$. Ar or the aromatic or heteroaromatic ring system here is preferably selected from substituted or unsubstituted phenyl, naphthyl, pyridine, triazine, pyrimidine, benzimidazole, thiophene, triphenylamine or combinations of these groups, each of which may be substituted by one or more radicals $R^2$.

Examples of compounds of the formula (1), formula (2), formula (3) and formula (4) according to the invention are the structures shown below.

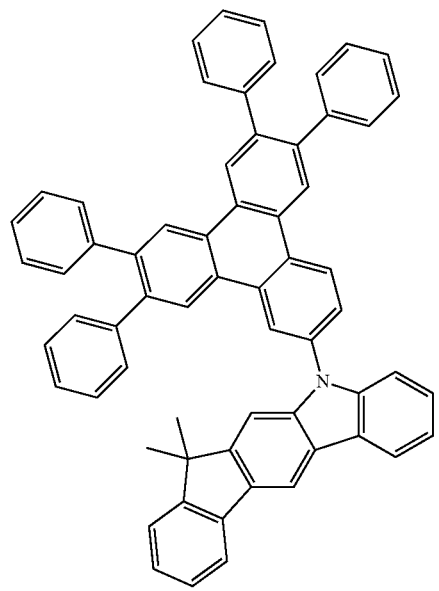 (1)
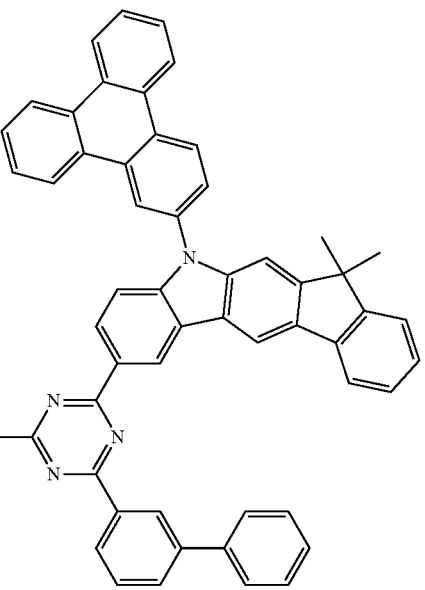 (2)
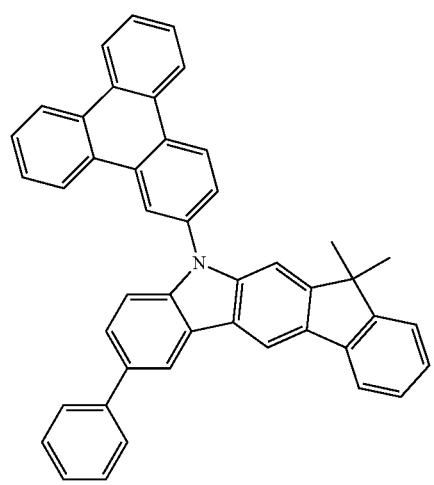 (3)
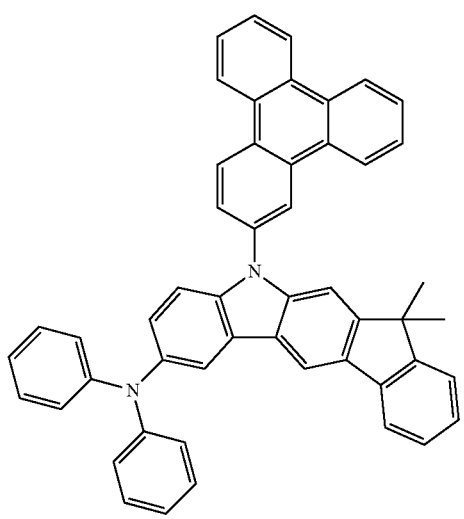 (4)
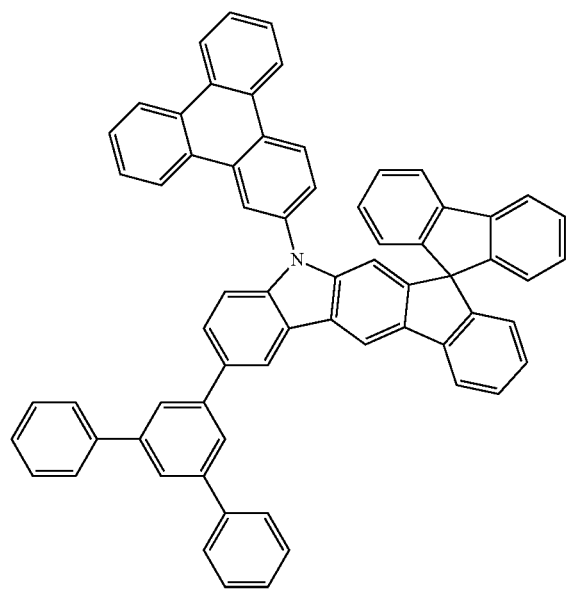 (5)
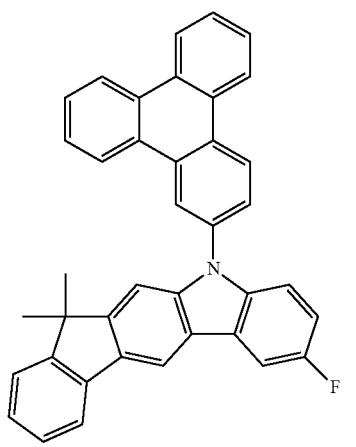 (6)

-continued
(7)
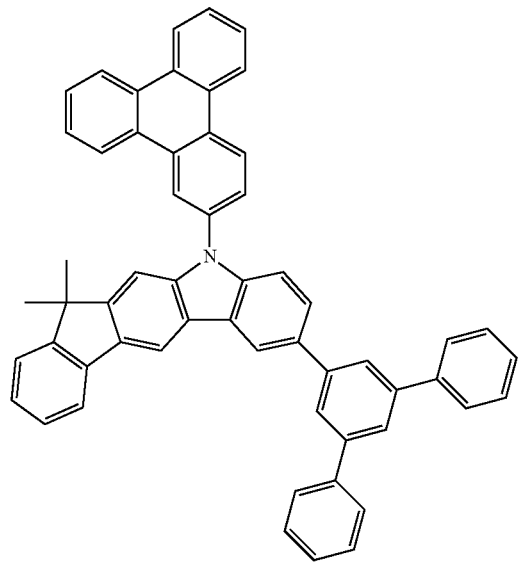
(8)
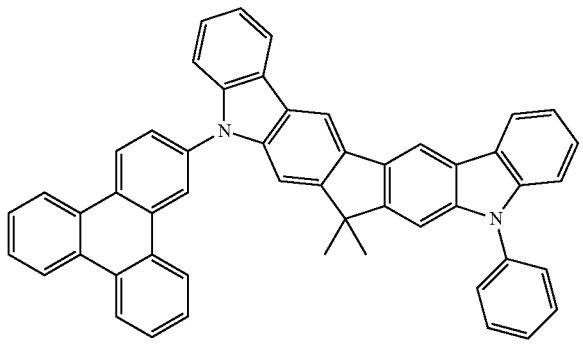
(9)
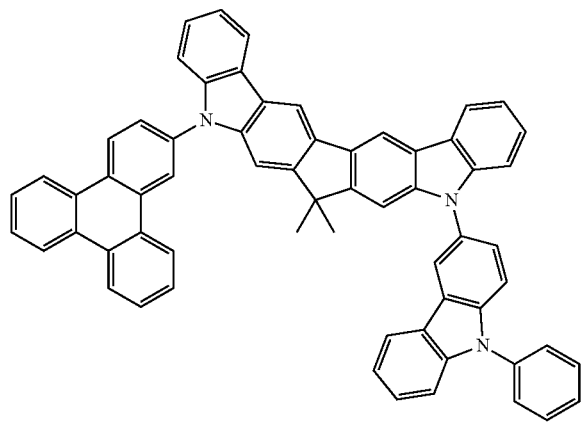
(10)
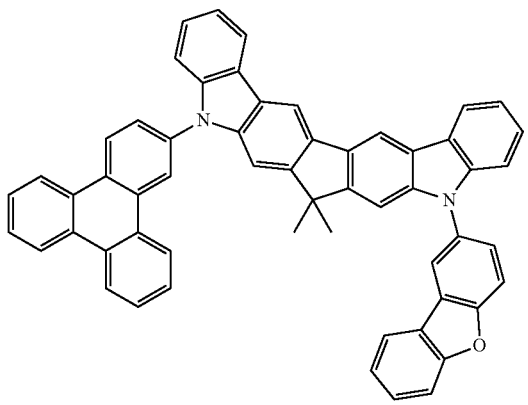
(11)
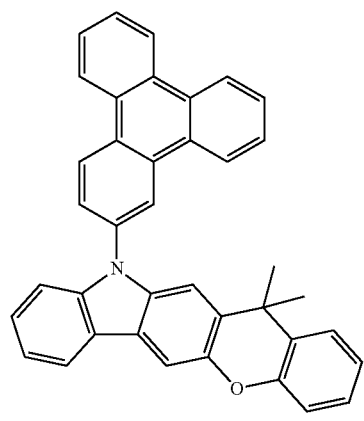
(12)
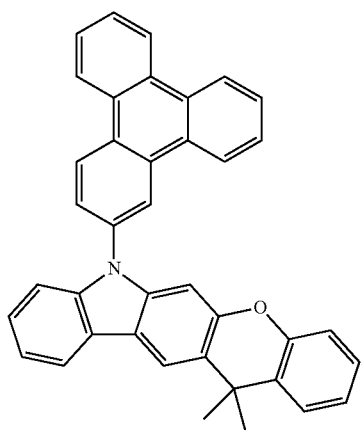

-continued
(13)
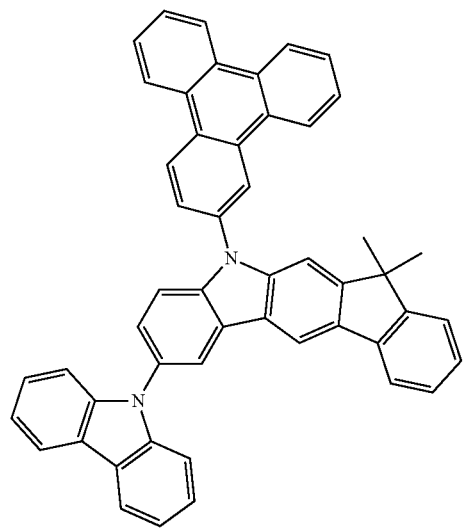
(14)
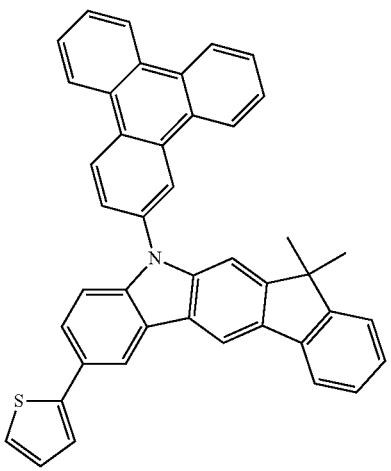
(15)
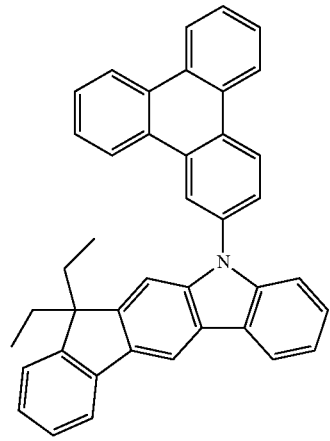
(16)
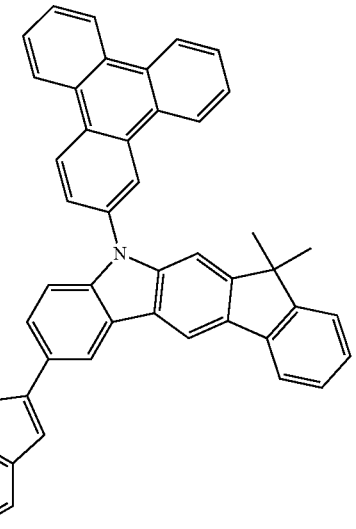
(17)
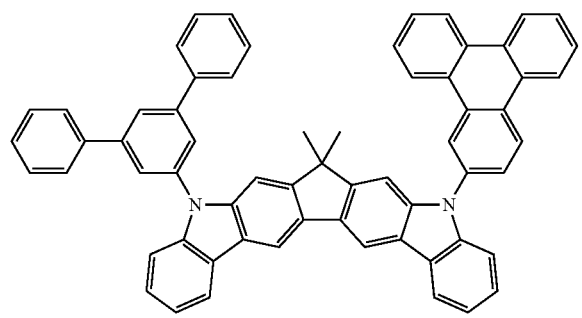
(18)
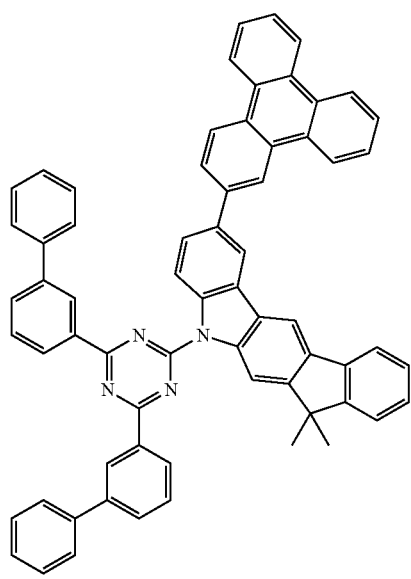

-continued
(19)
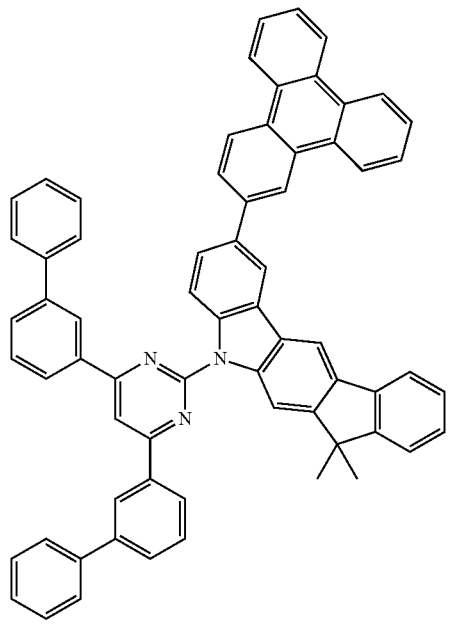
(20)
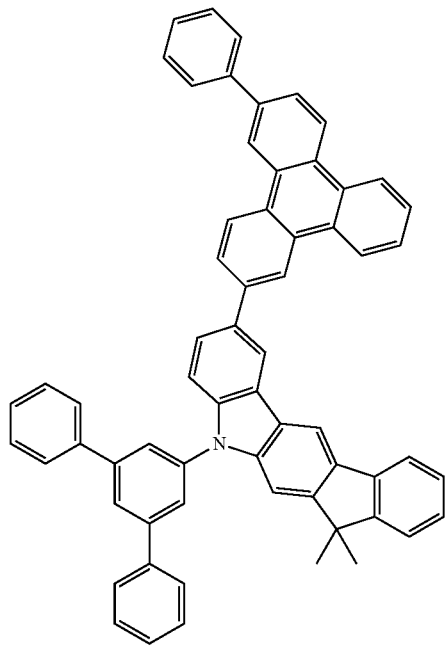
(21)
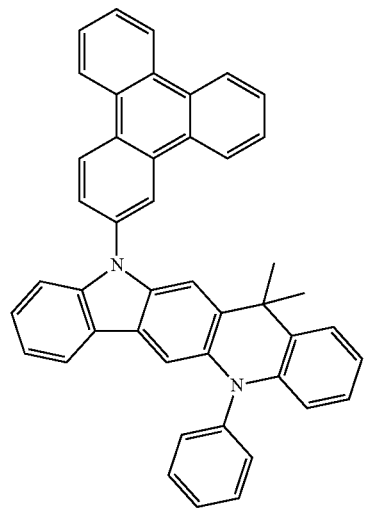
(22)
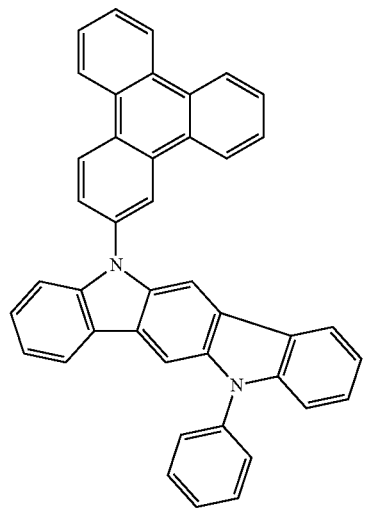
(23)
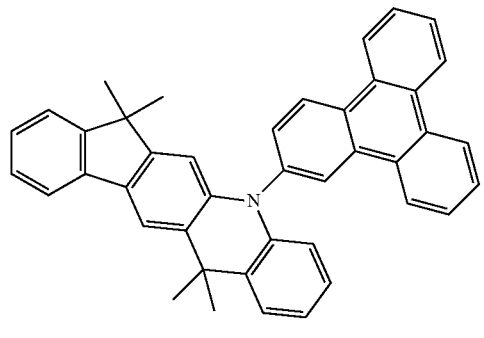
(24)
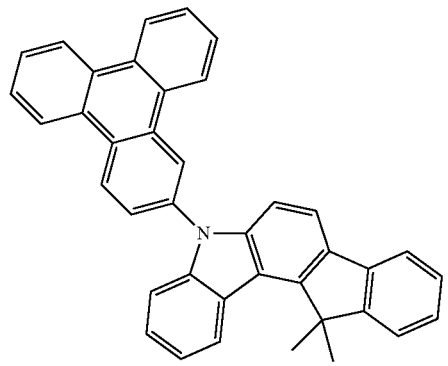

-continued
(25)
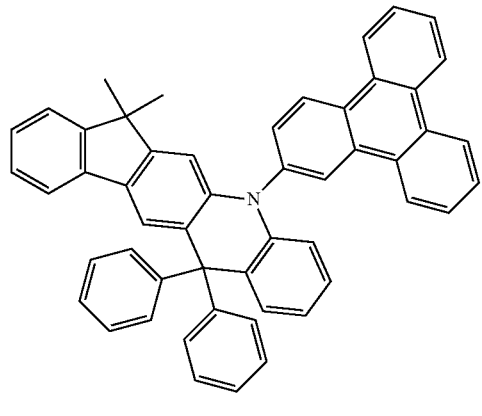
(26)
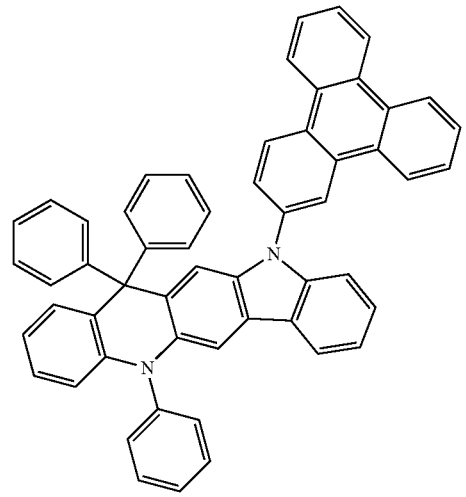
(27)
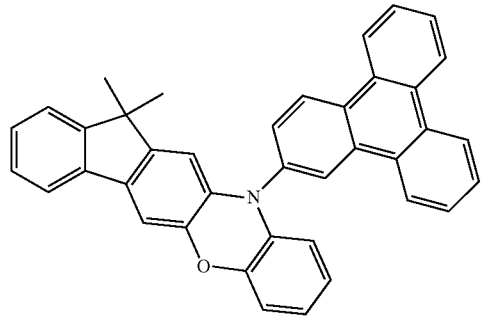
(28)
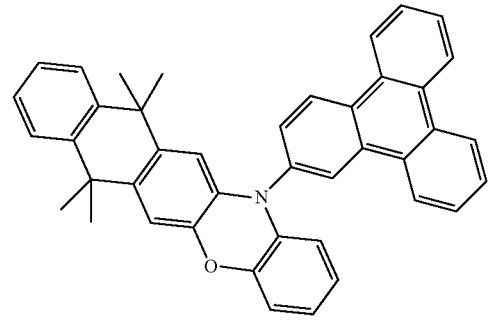
(29)
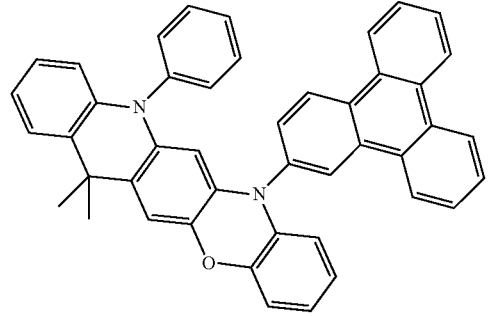
(30)
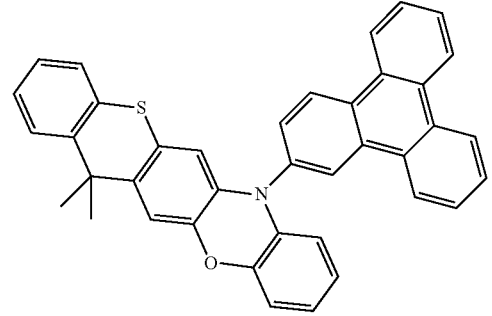
(31)
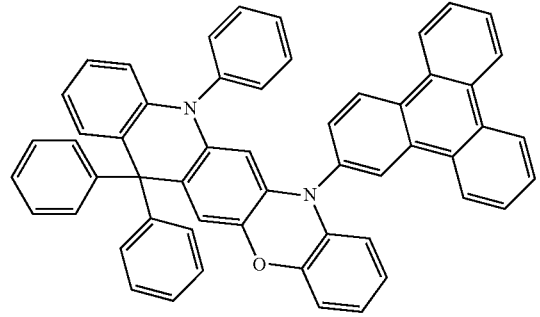
(32)
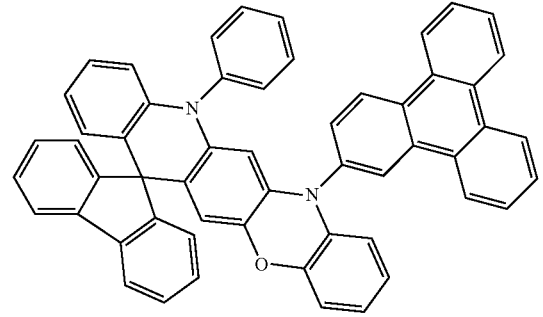

-continued
(33)
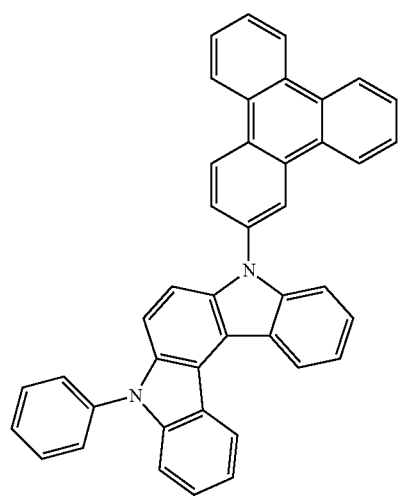
(34)
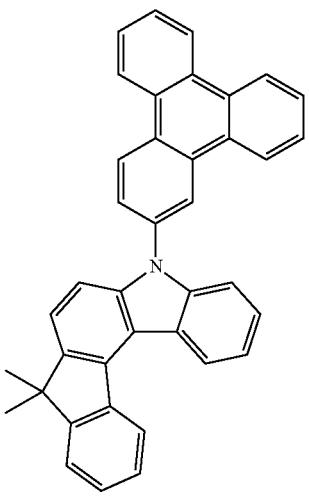
(35)
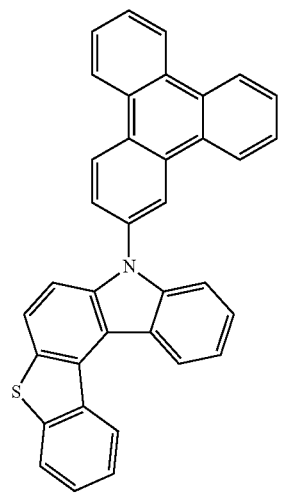
(36)
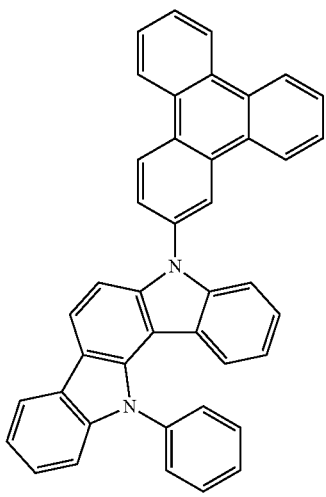
(37)
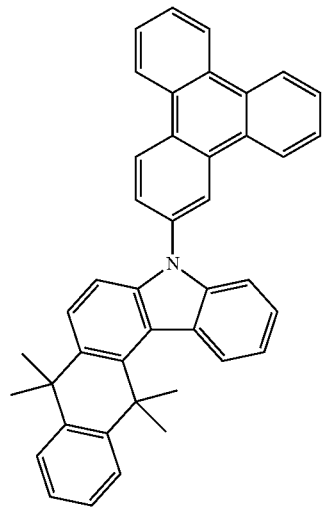
(38)
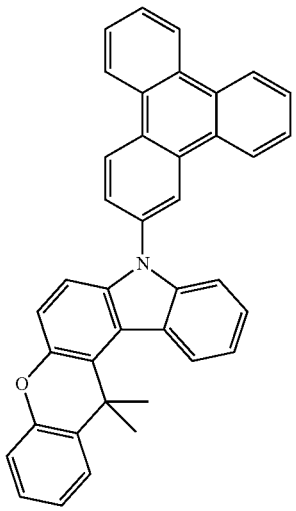

-continued
(39)
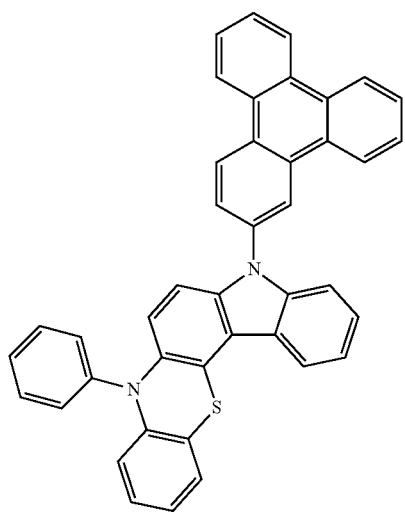
(40)
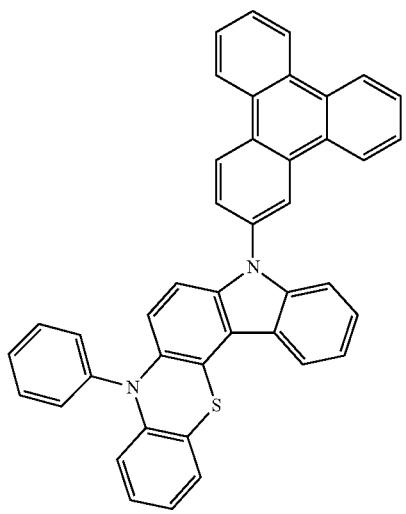
(41)
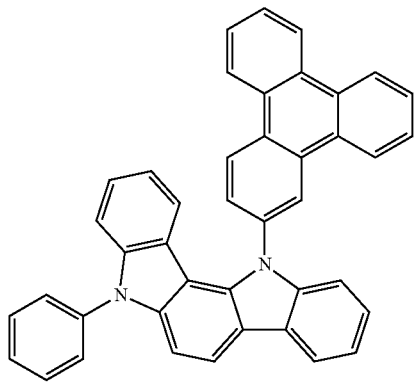
(42)
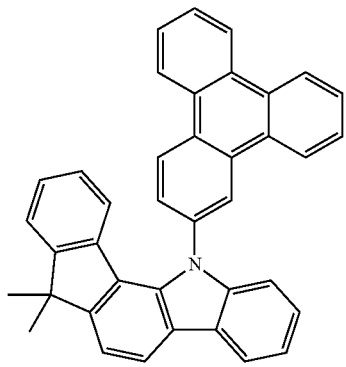
(43)
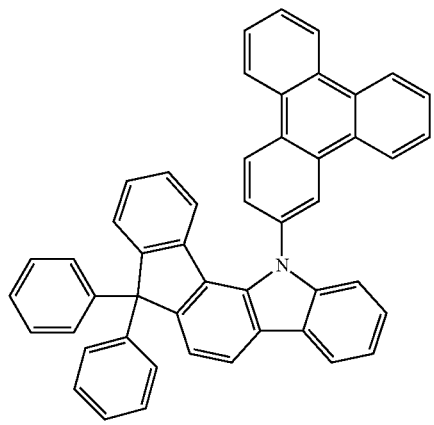
(44)
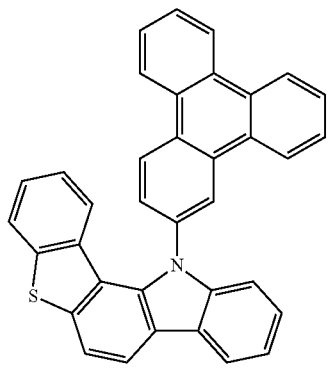

(45)
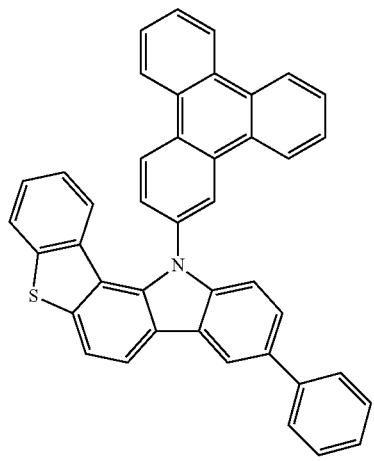
(46)
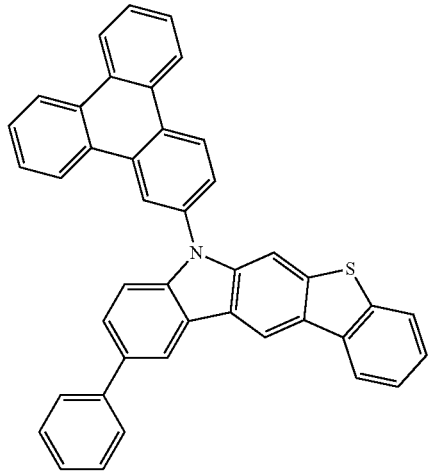
(47)
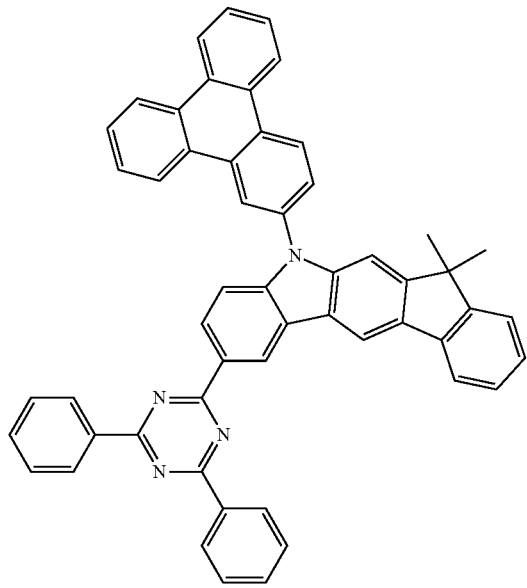
(48)
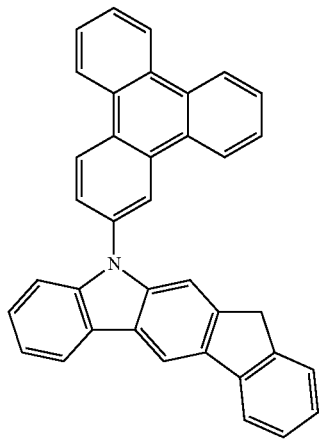
(49)
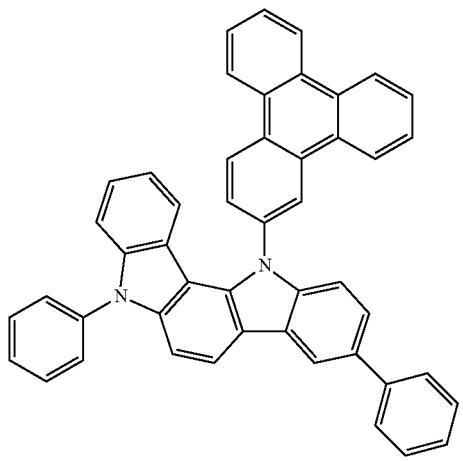
(50)
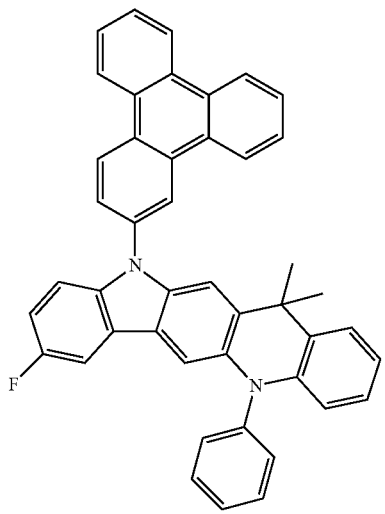

-continued
(51) 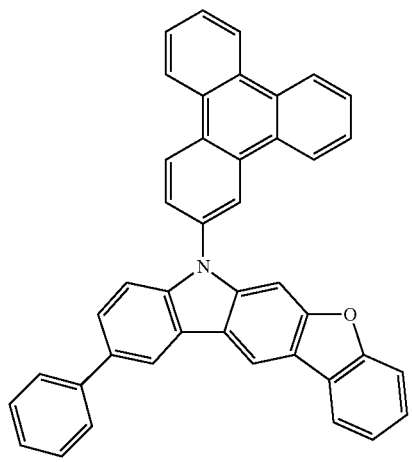
(52) 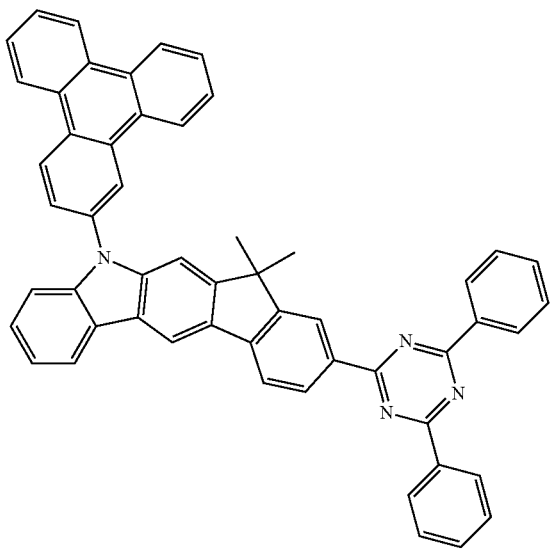
(53) 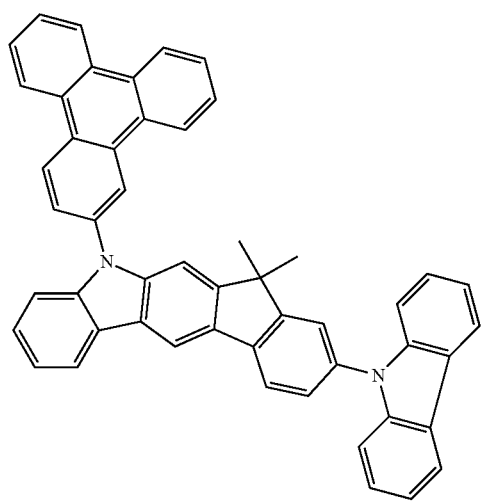
(54) 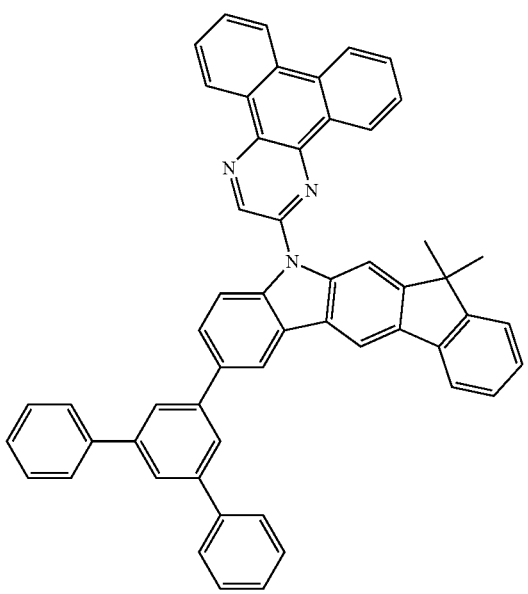
(55) 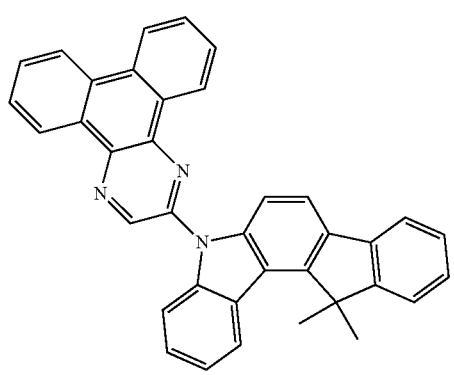
(56) 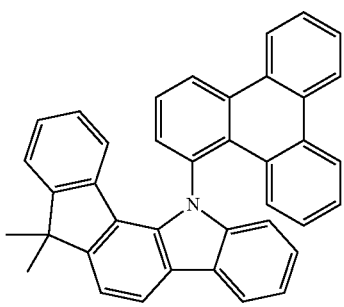

-continued
(57) 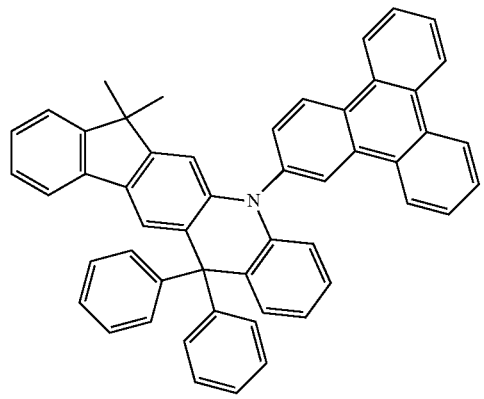
(58) 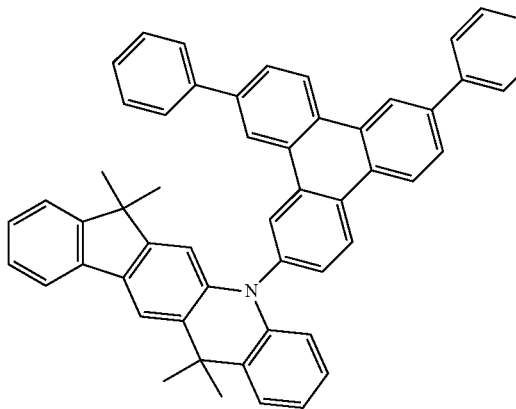
(59) 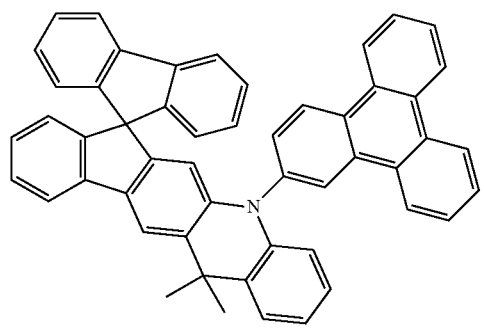
(60) 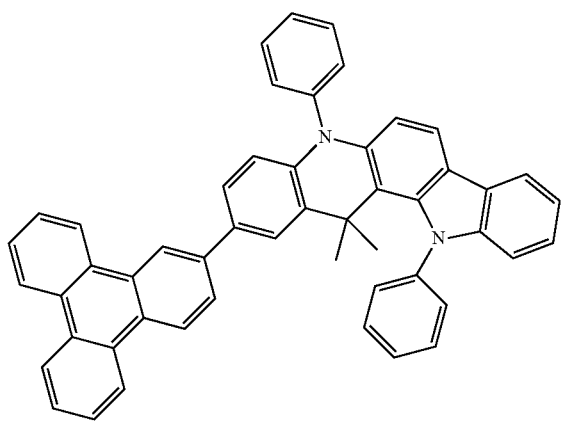
(61) 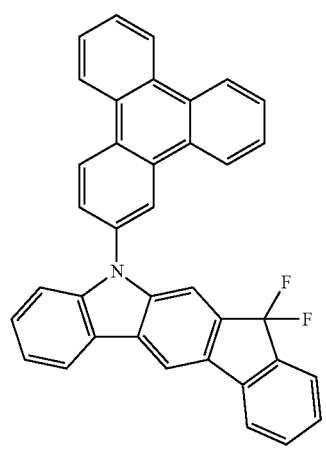
(62) 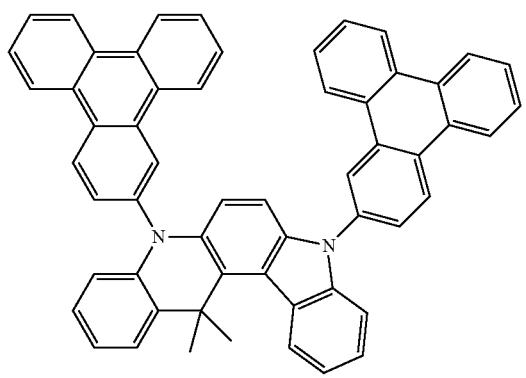

-continued
(63)
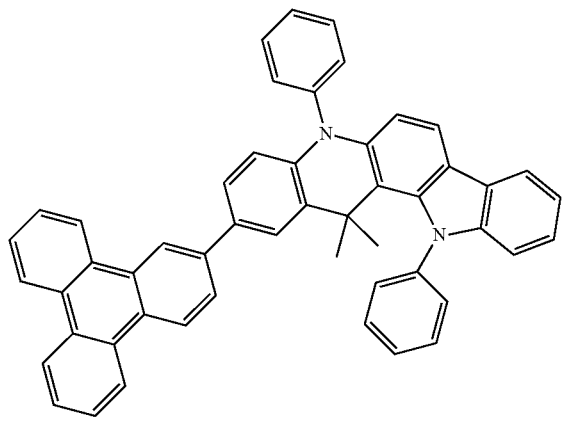
(64)
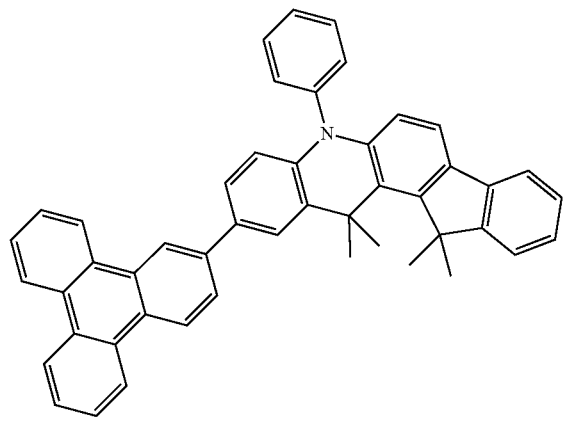
(65)
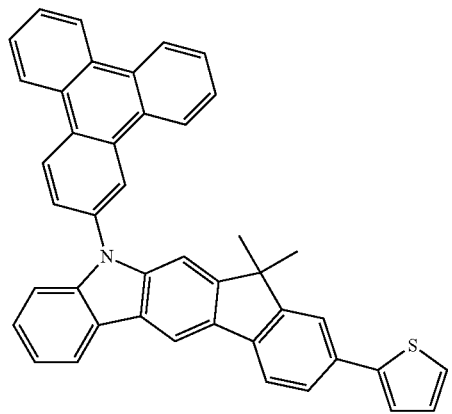
(66)
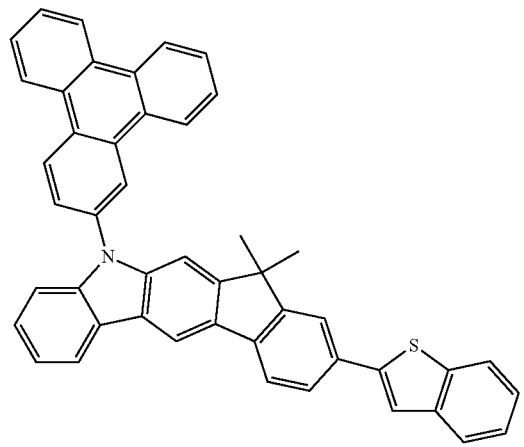
(67)
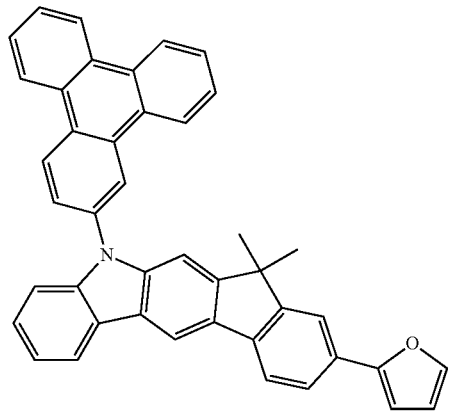
(68)
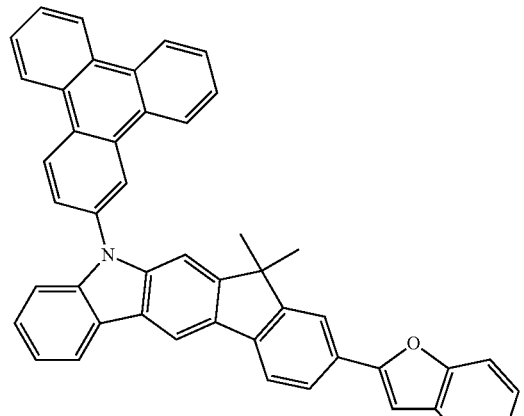

-continued
(69)
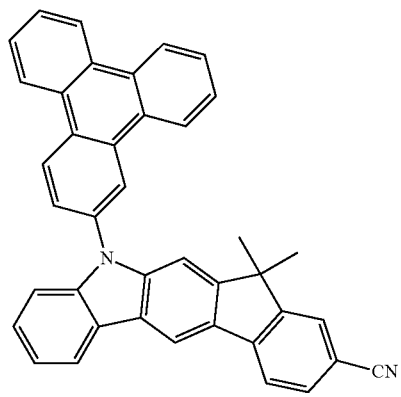
(70)
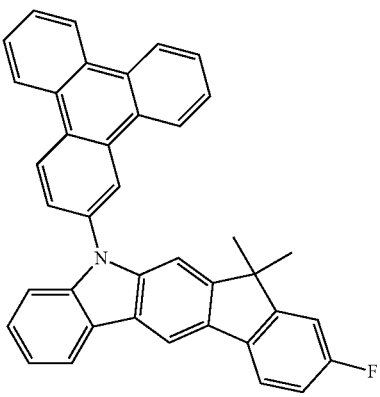
(71)
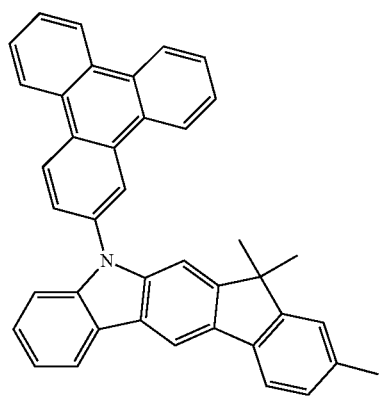
(72)
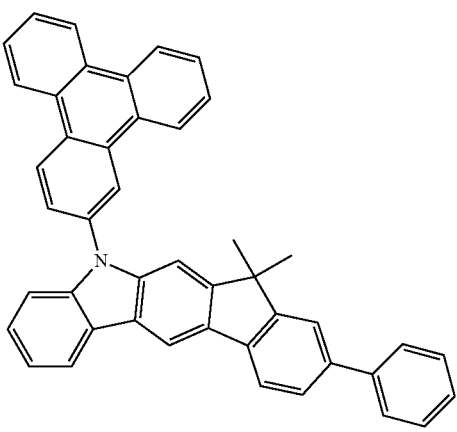
(73)
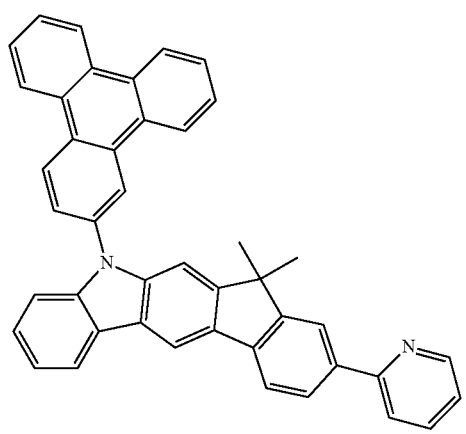
(74)
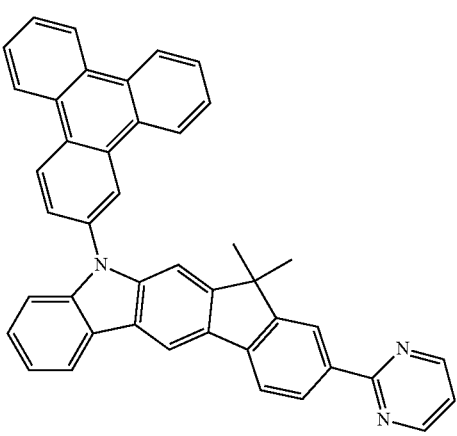

(75)
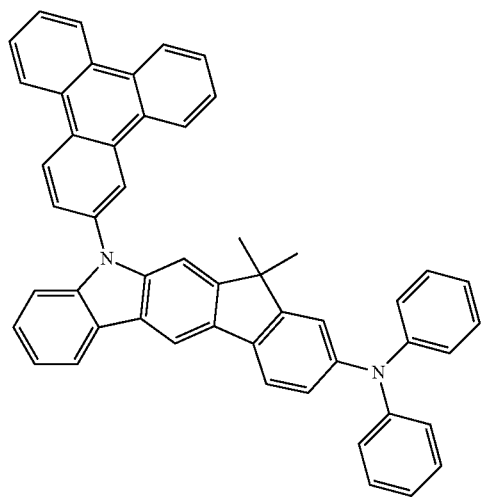
(76)
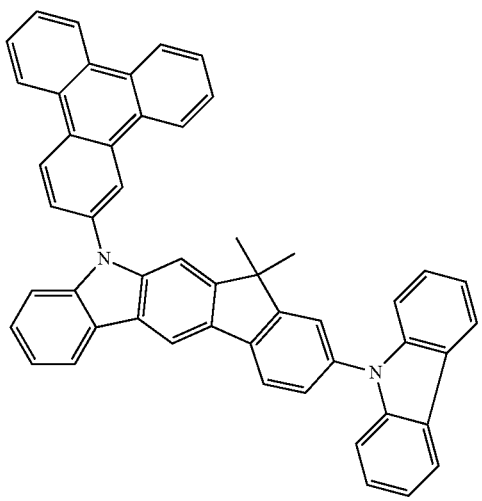
(77)
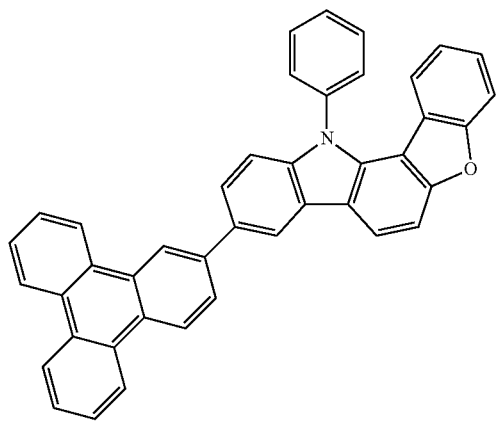
(78)
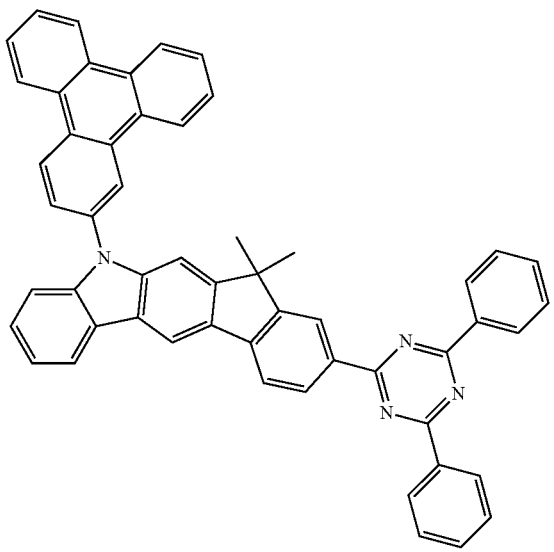
(79)
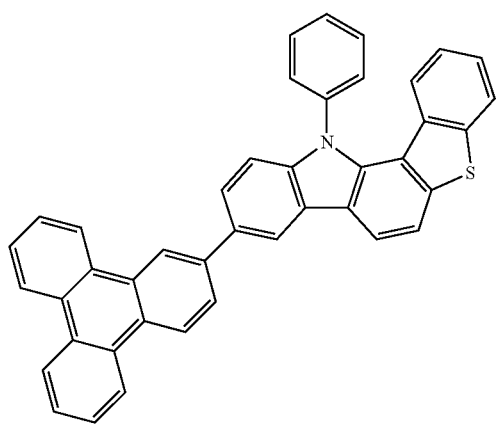
(80)
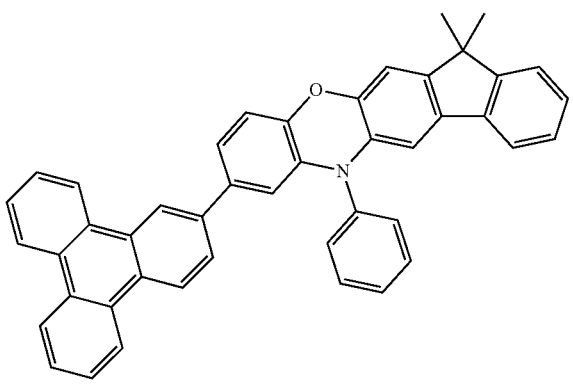

-continued
(81)
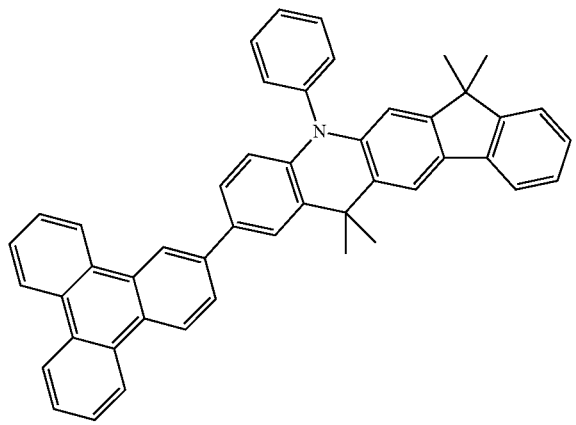
(82)
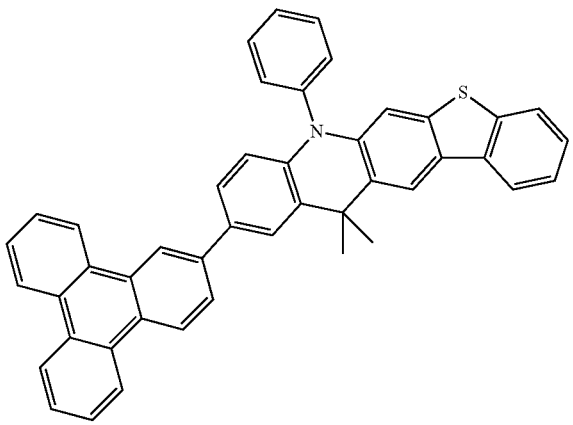
(83)
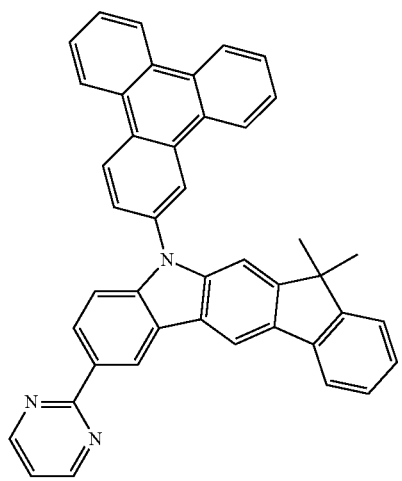
(84)
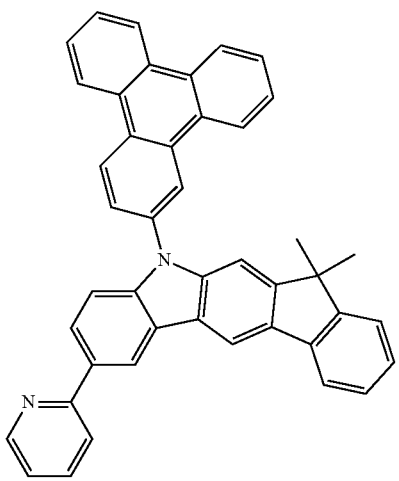
(85)
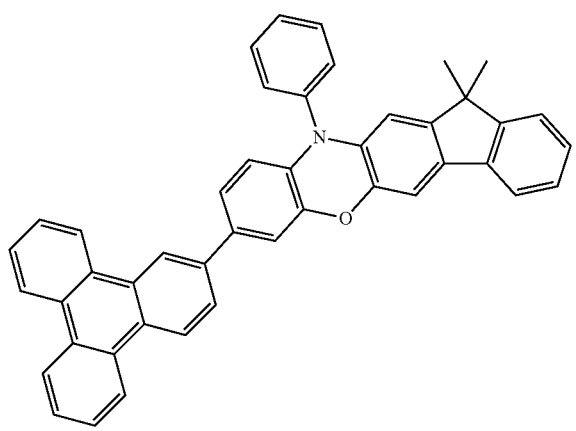
(86)
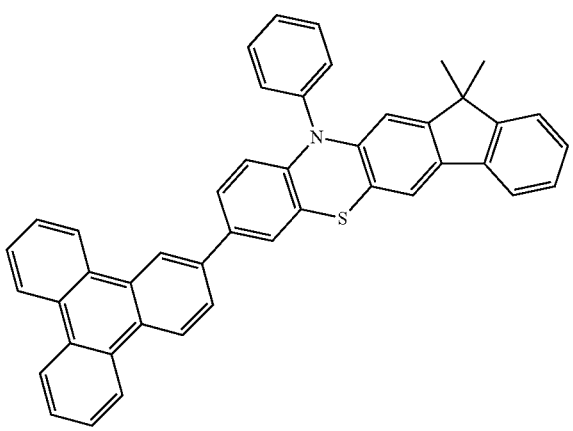

-continued
(87)
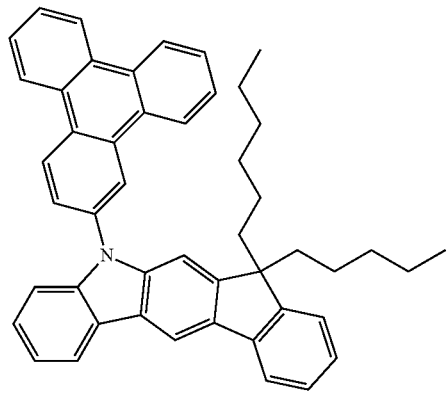
(88)
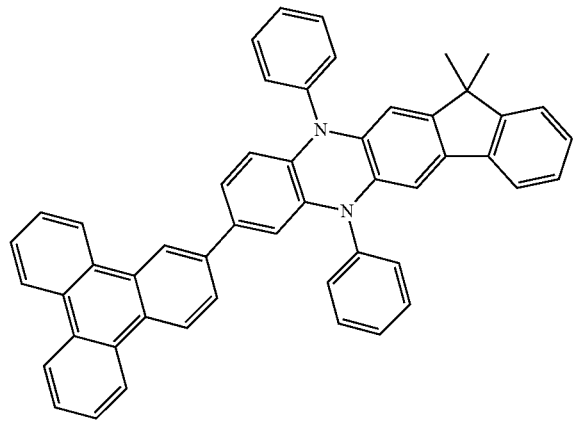
(89)
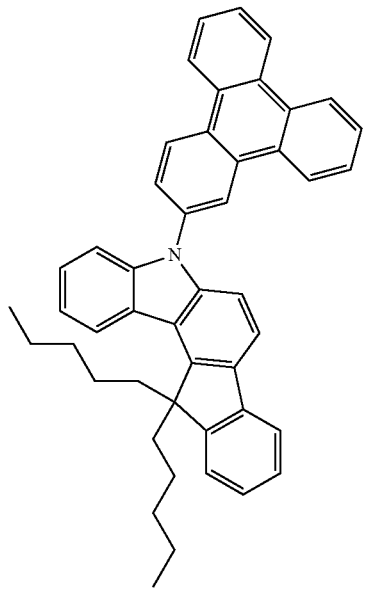
(90)
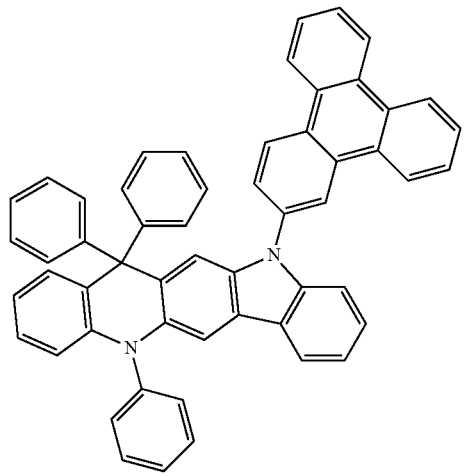
(91)
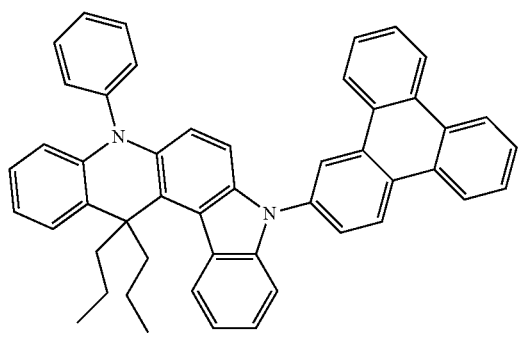
(92)
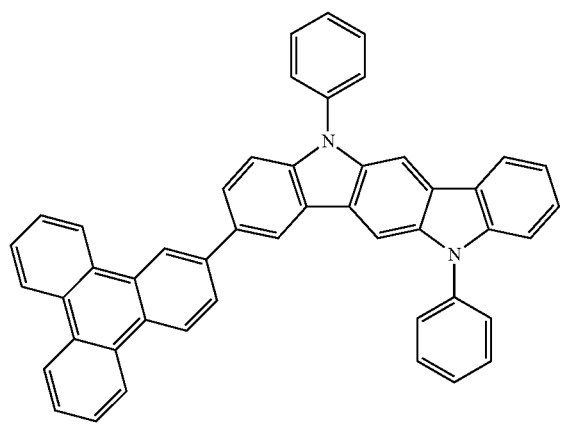

-continued
(93)
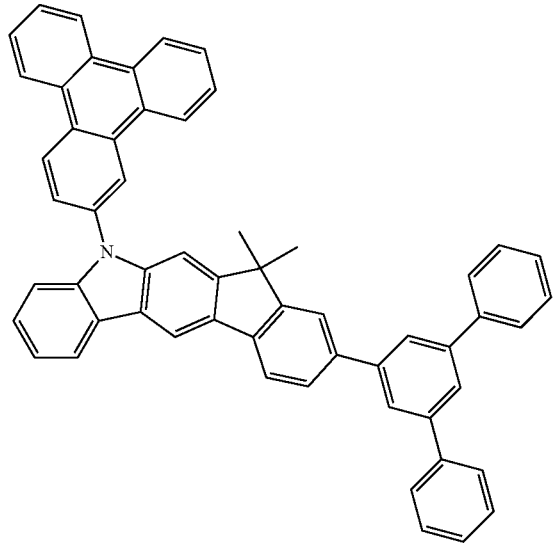
(94)
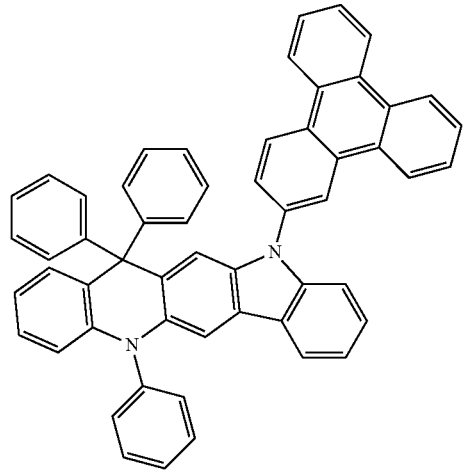
(95)
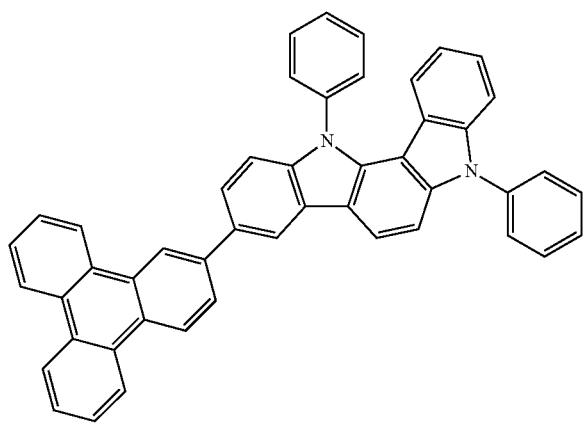
(96)
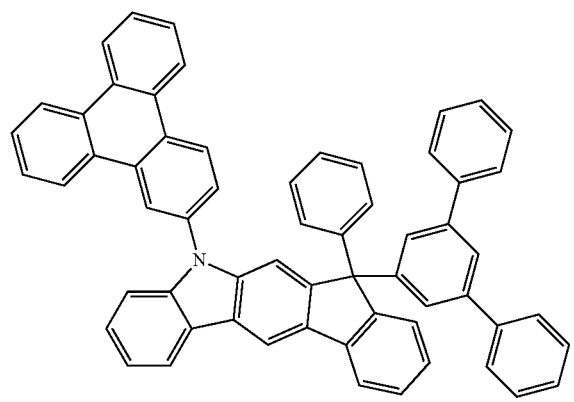
(97)
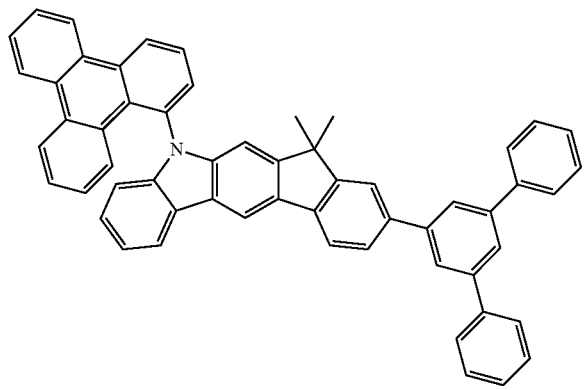
(98)
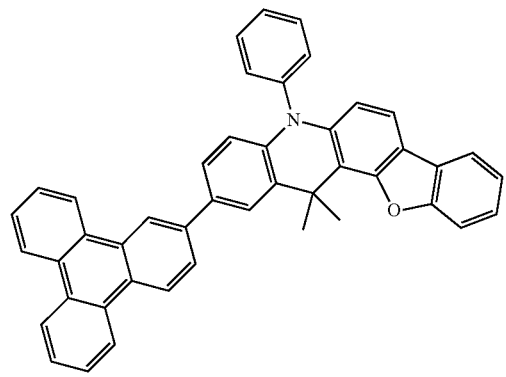

-continued
(99)
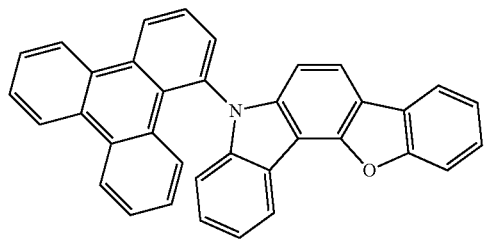
(100)
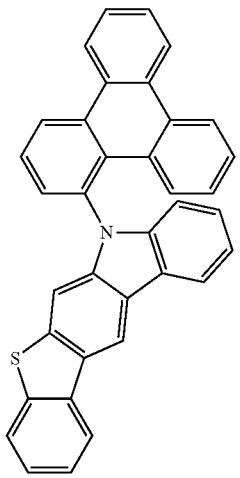
(101)
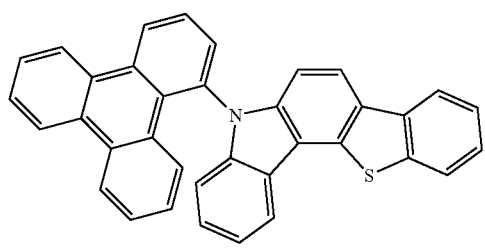
(102)
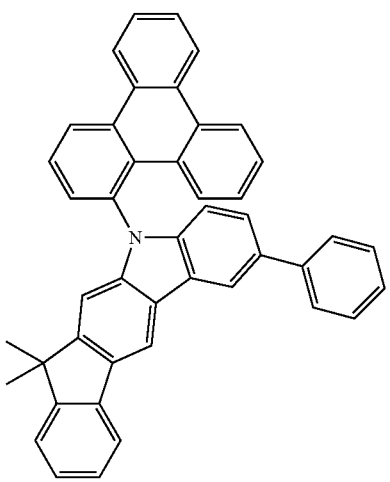
(103)
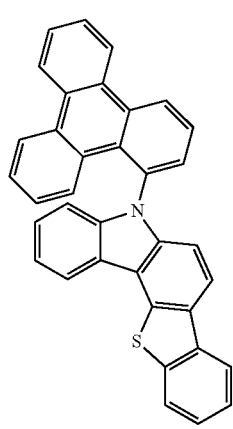
(104)
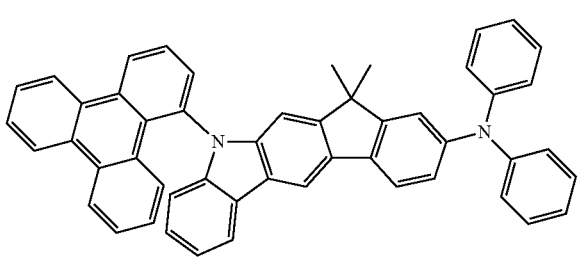

-continued
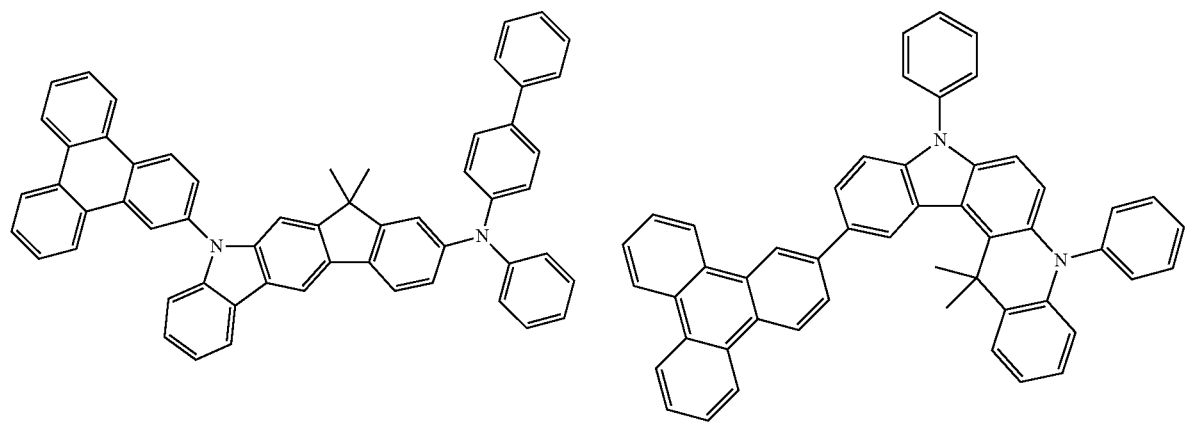
(105)
(104)
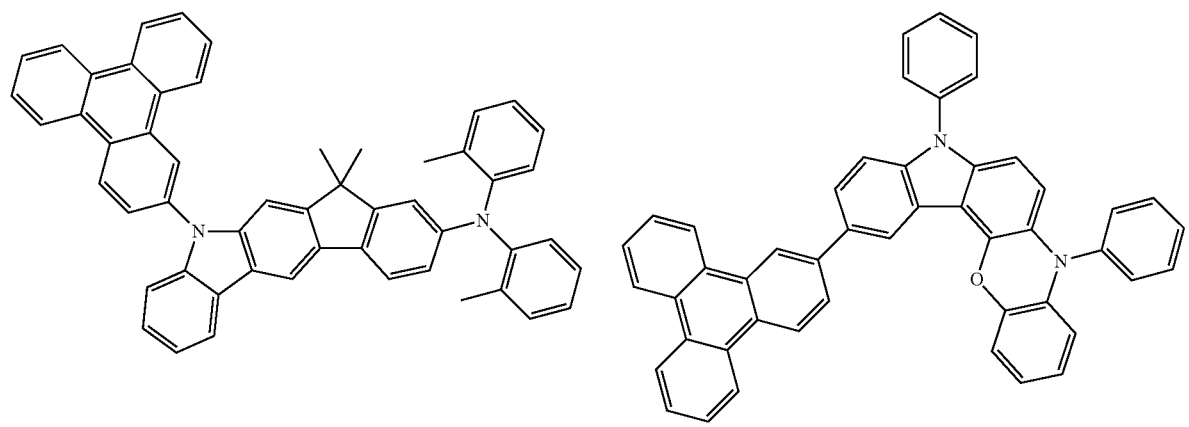
(105)
(106)
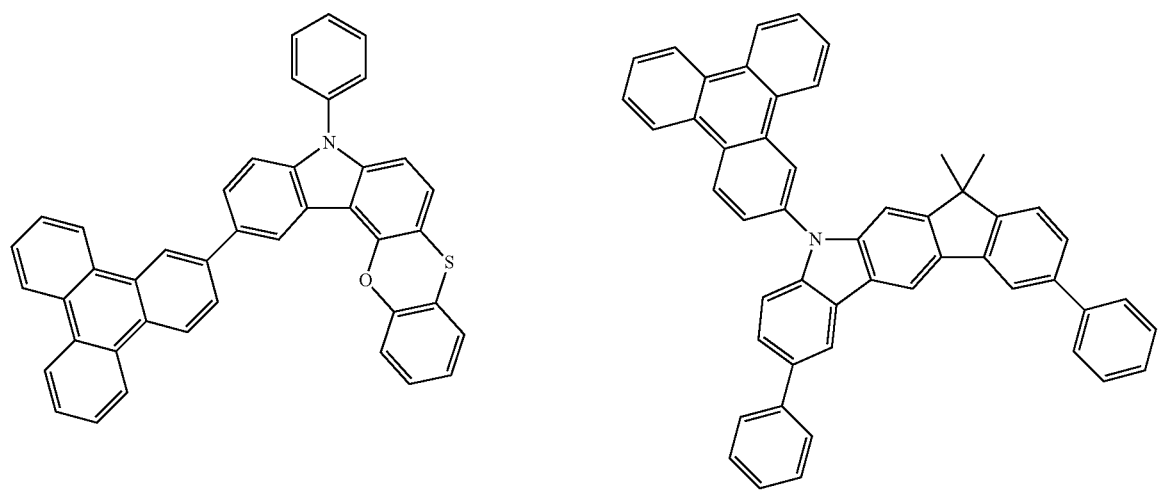
(107)
(108)

-continued
(109)
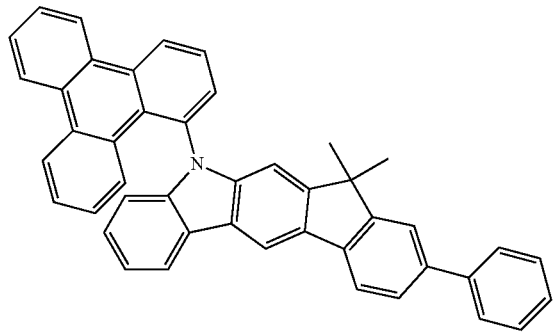
(110)
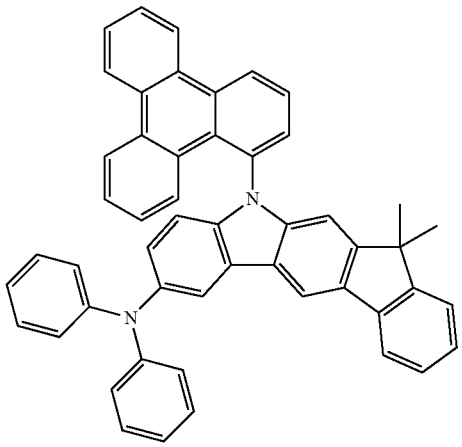
(111)
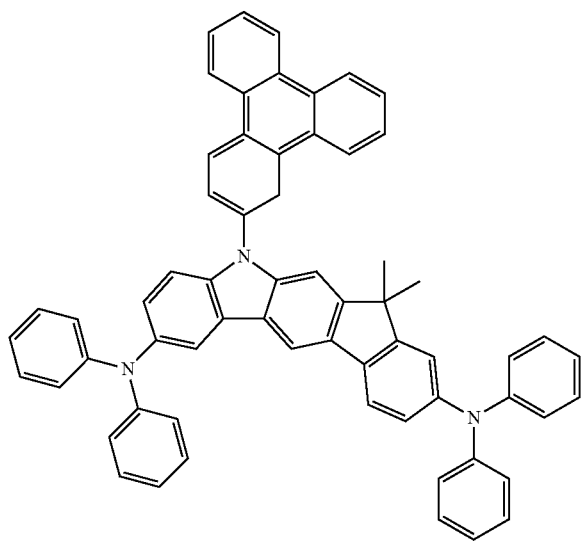
(112)
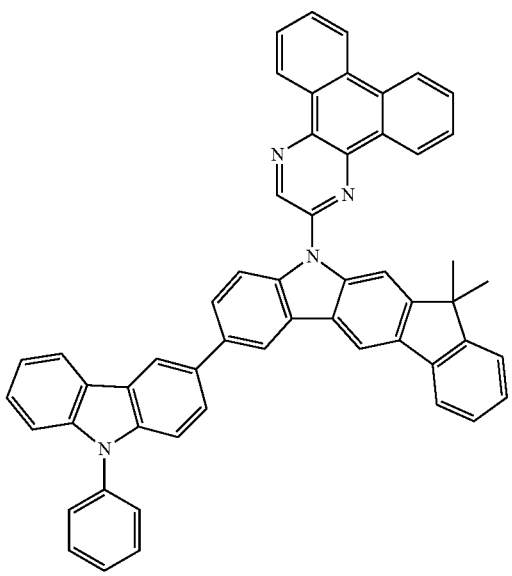
(113)
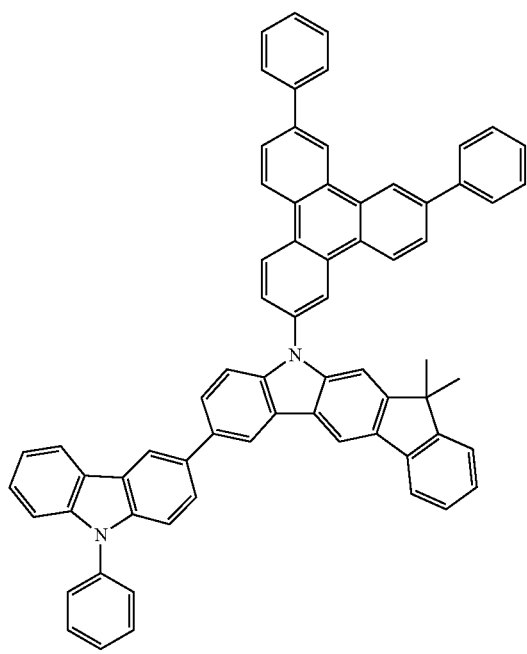
(114)
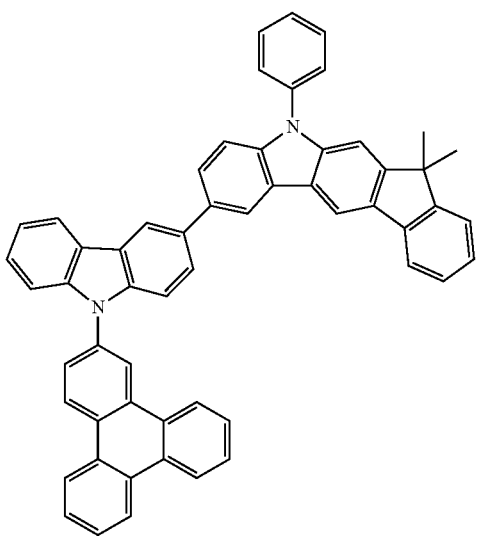

(115) 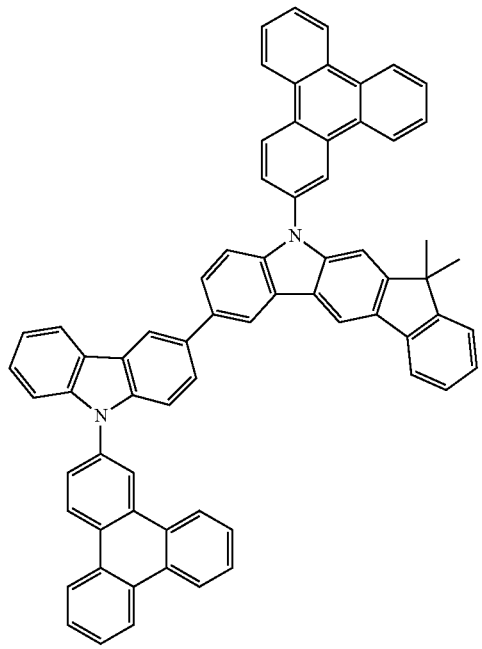
(116) 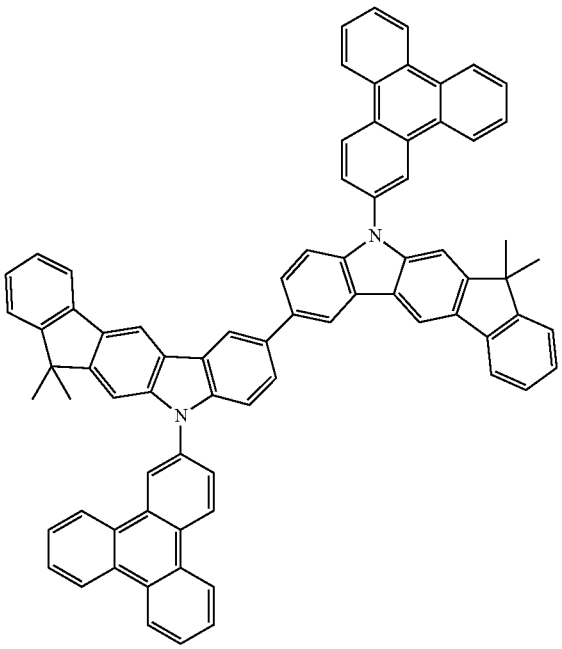
(117) 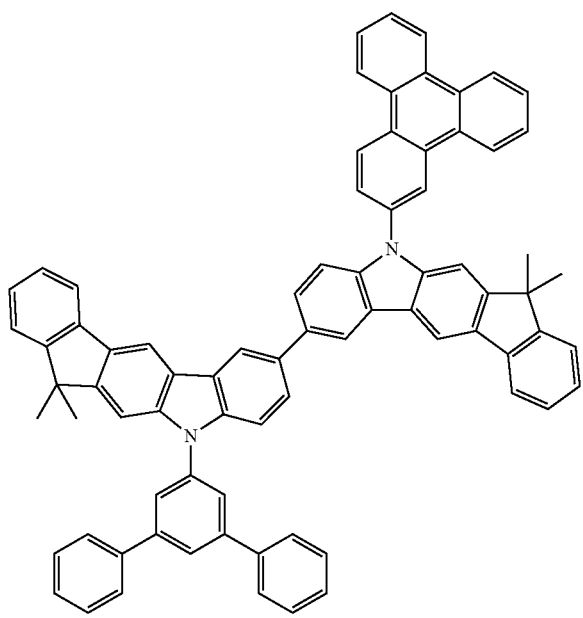
(118) 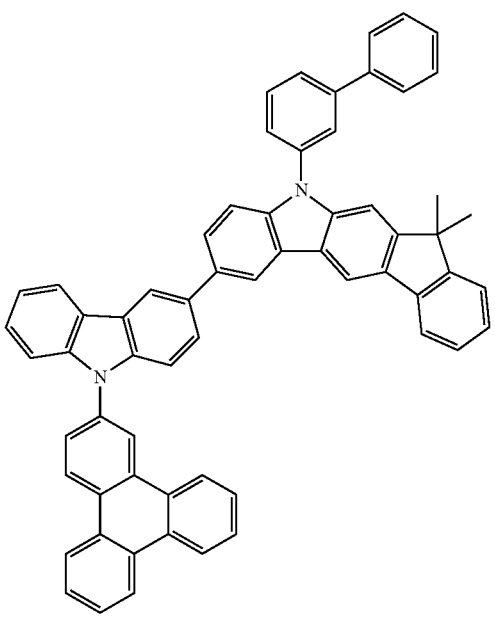

(119)
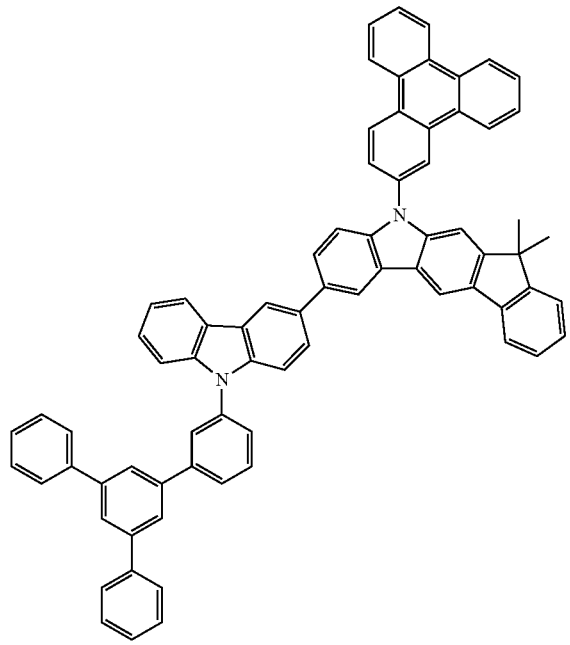
(120)
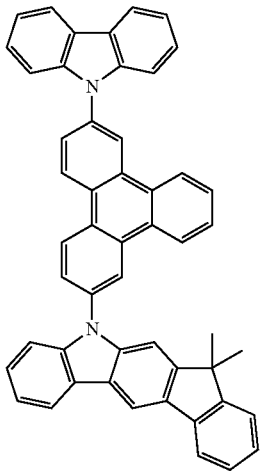
(121)
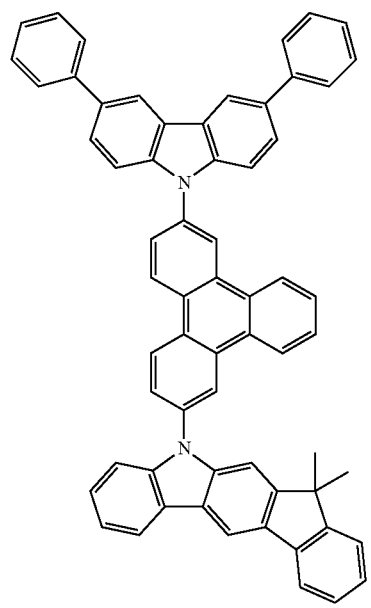
(122)
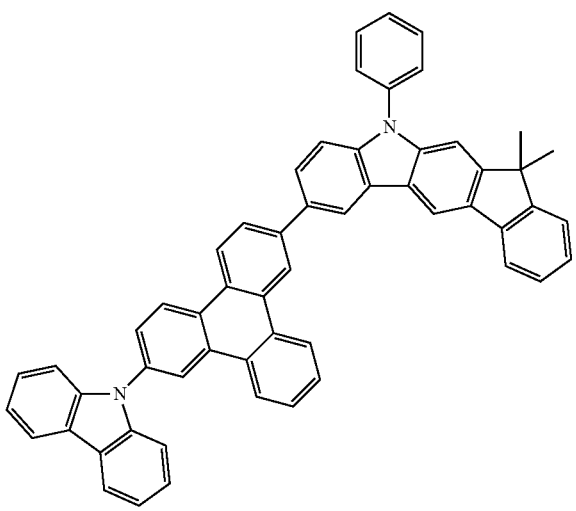

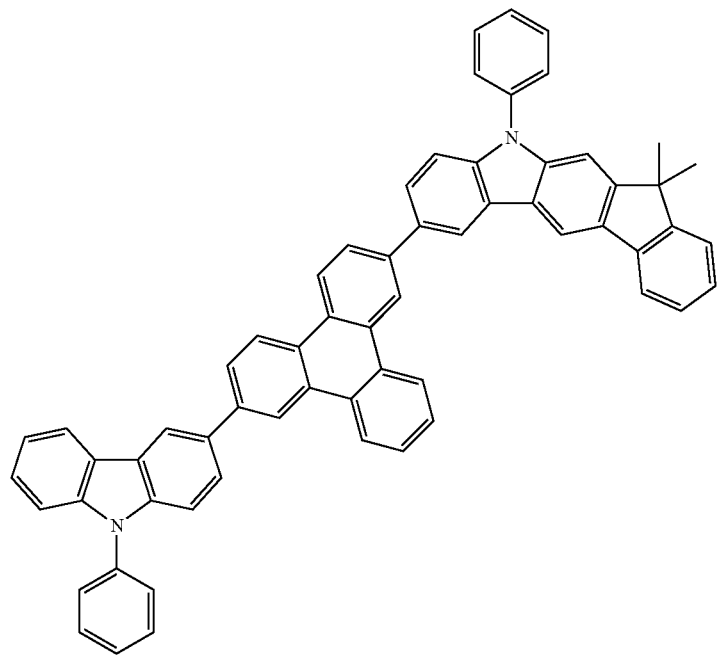
(123)
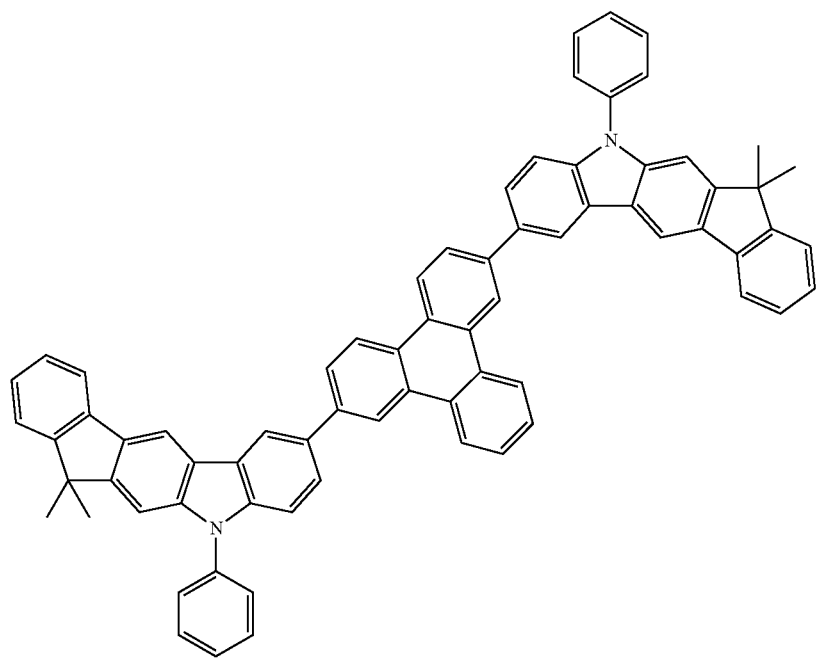
(124)

-continued
(125)
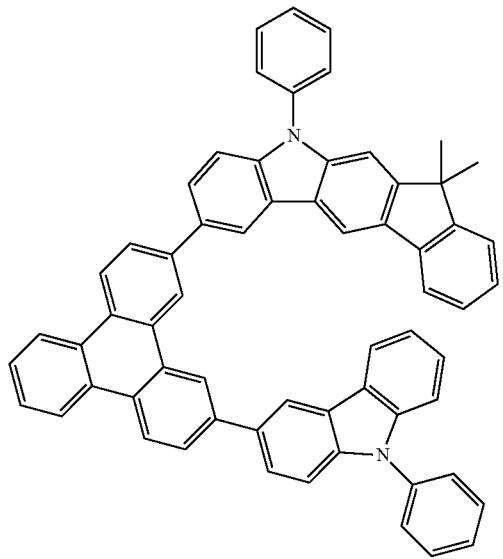
(126)
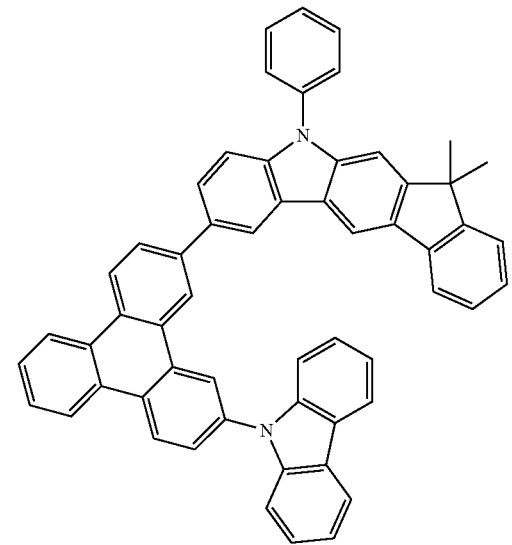
(127)
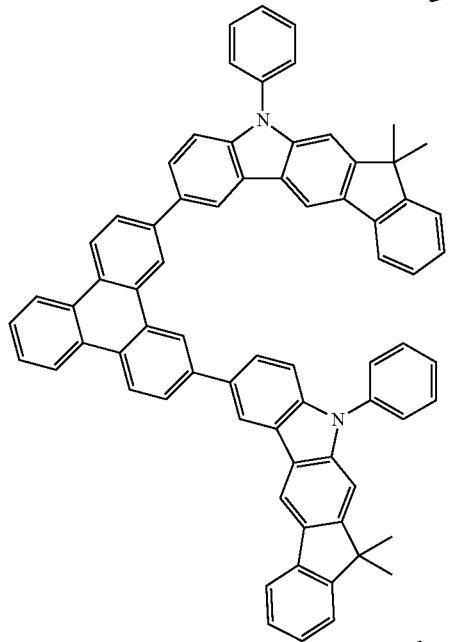
(128)
(129)
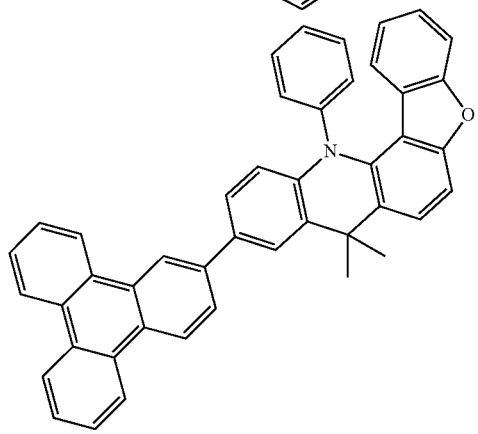
(130)
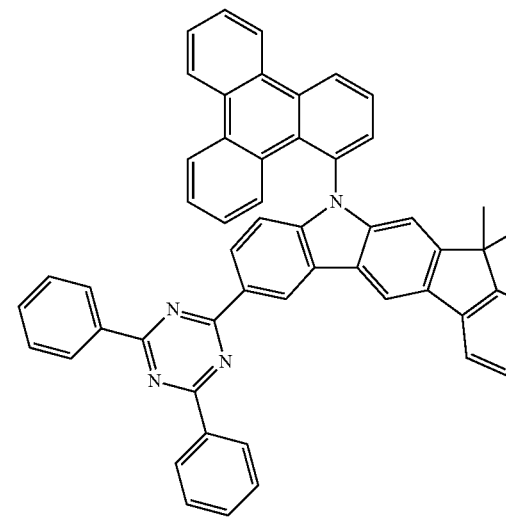

-continued
(131)
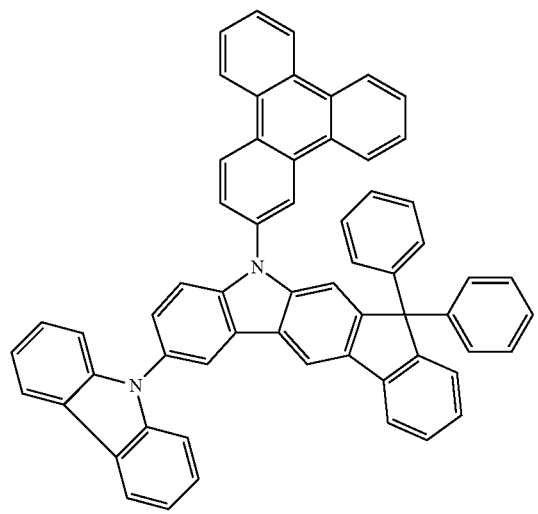
(132)
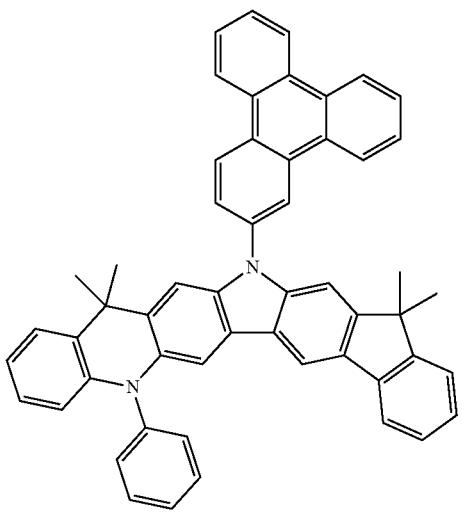
(133)
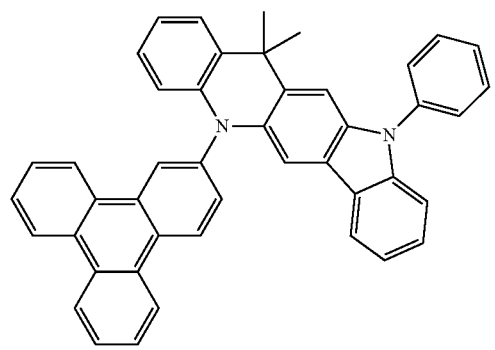
(134)
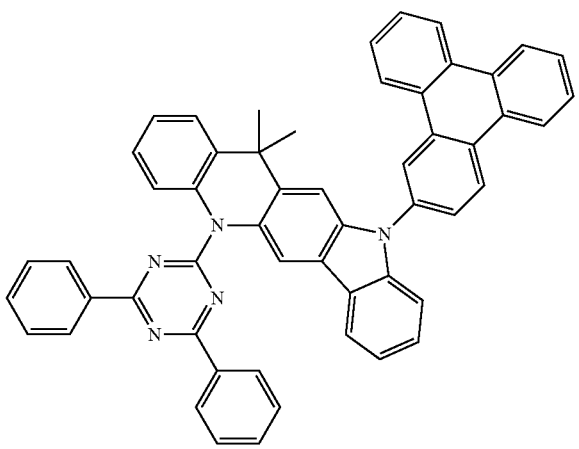
(135)
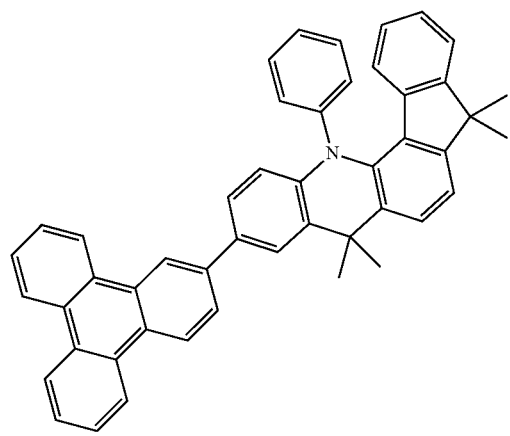
(136)
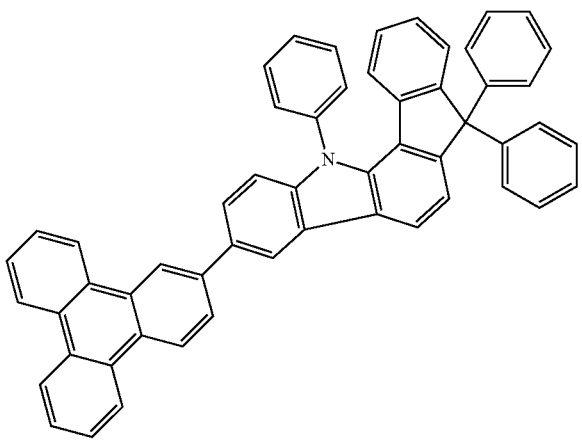

-continued
(137)
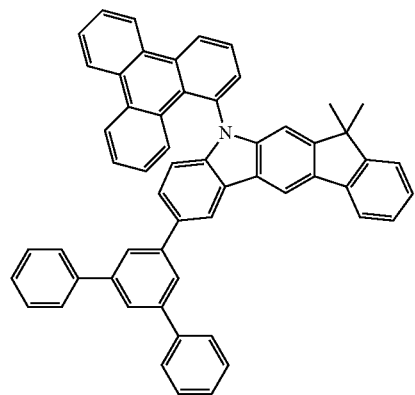
(138)
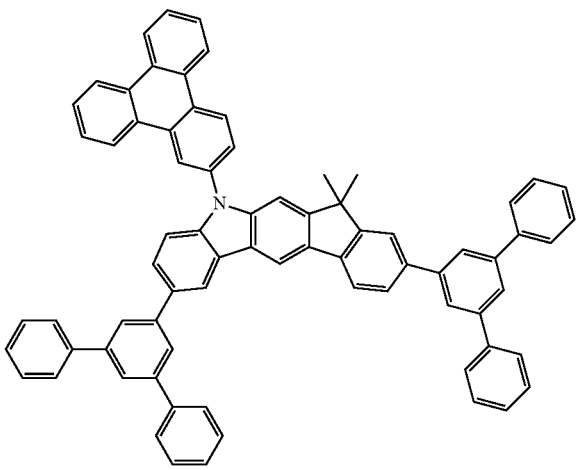
(139)
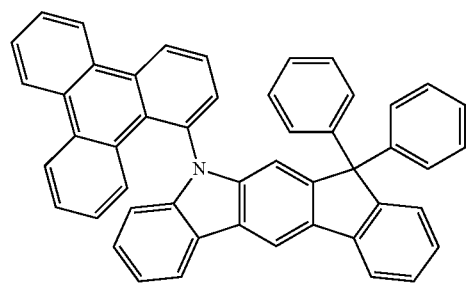
(140)
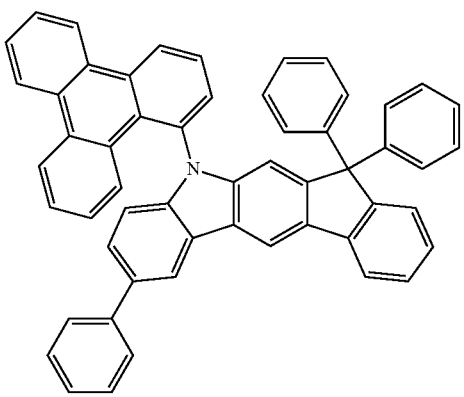
(141)
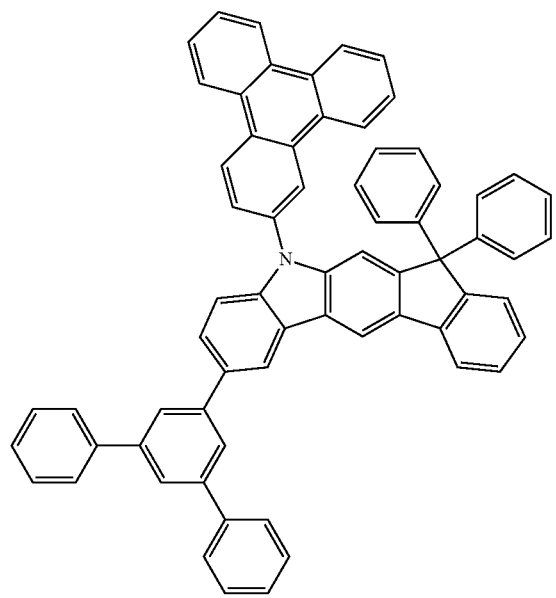
(142)
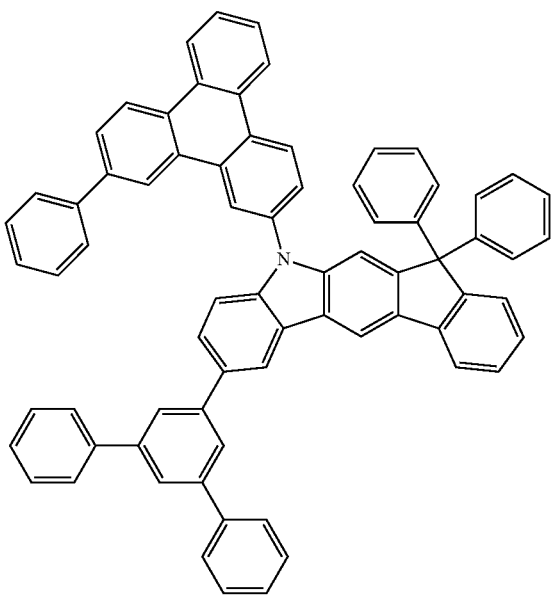

-continued
(143)
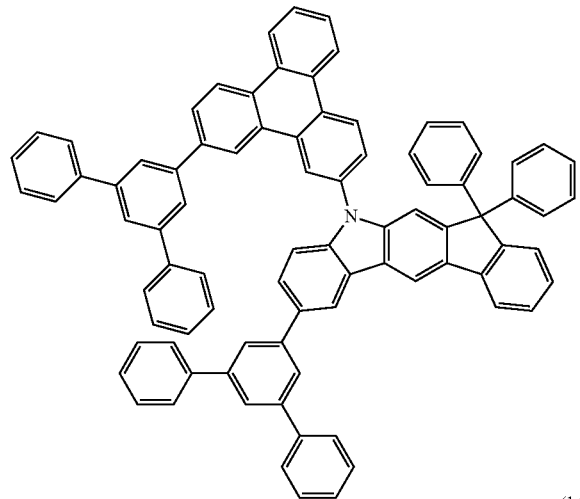
(144)
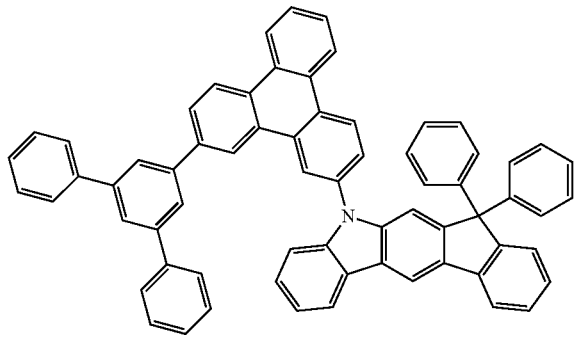
(145)
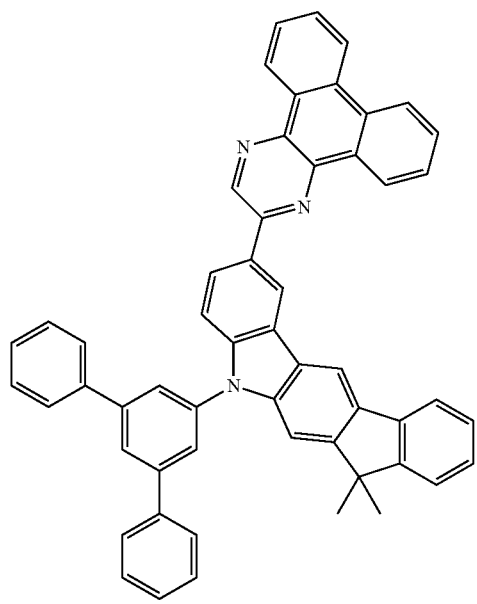
(146)
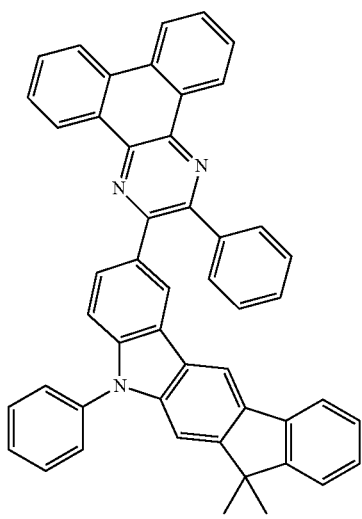
(147)
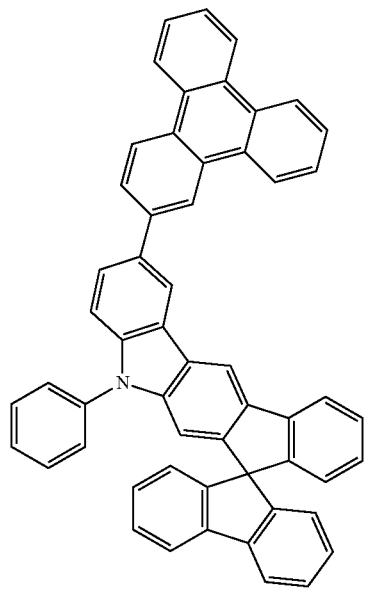
(148)
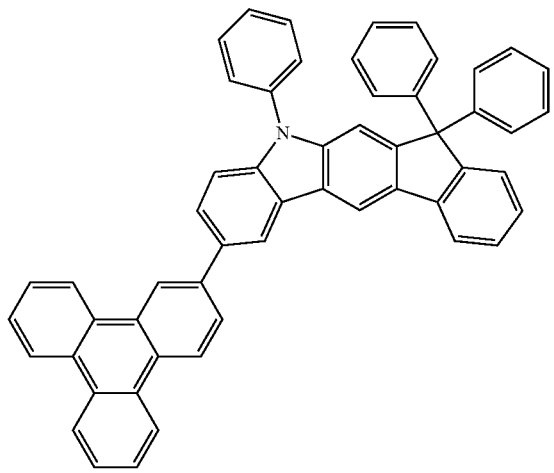

-continued
(149)
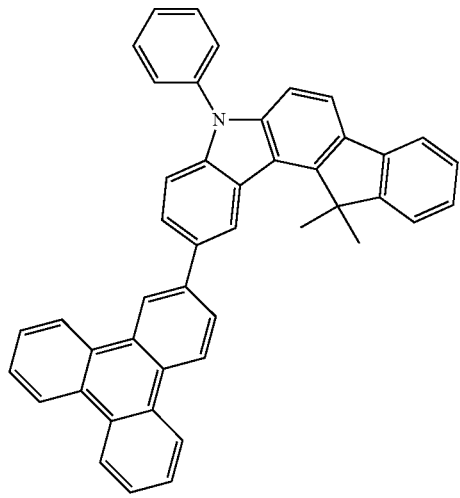
(150)
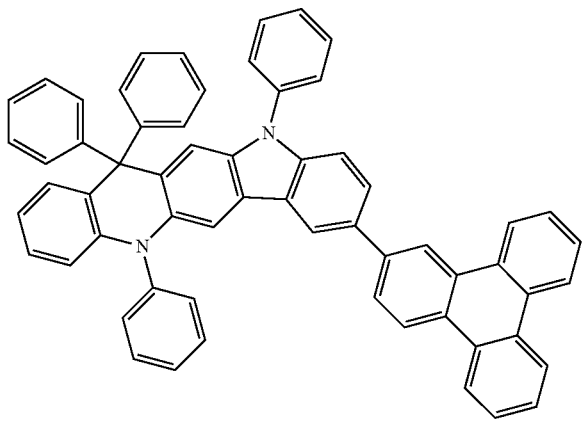
(151)
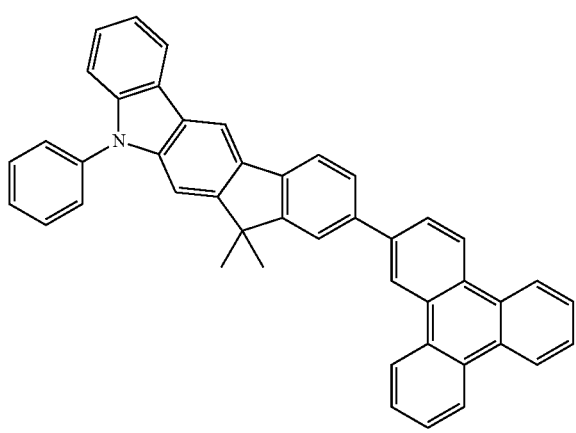
(152)
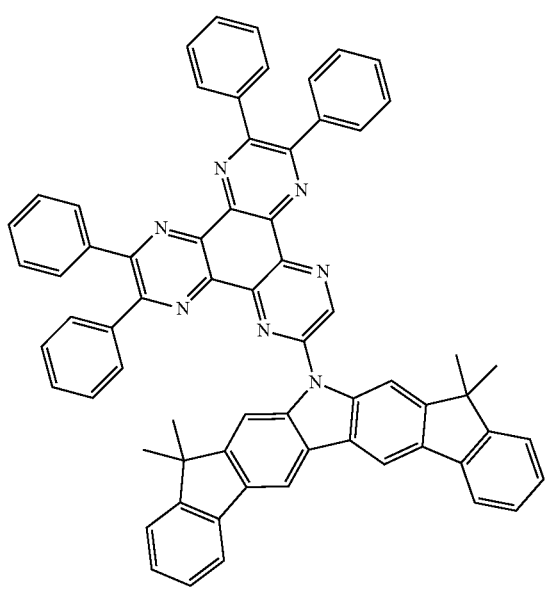

(153)
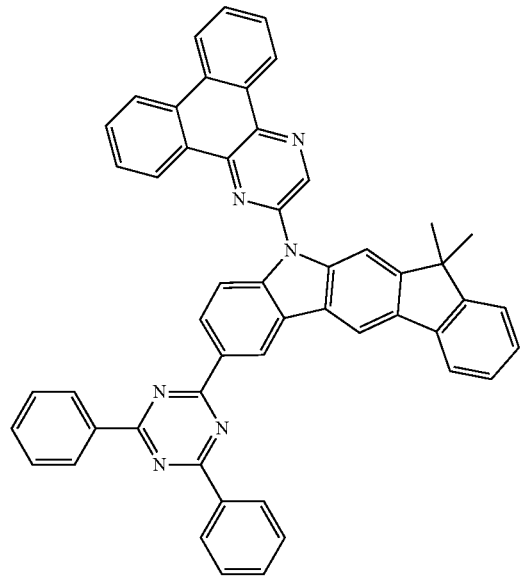
(154)
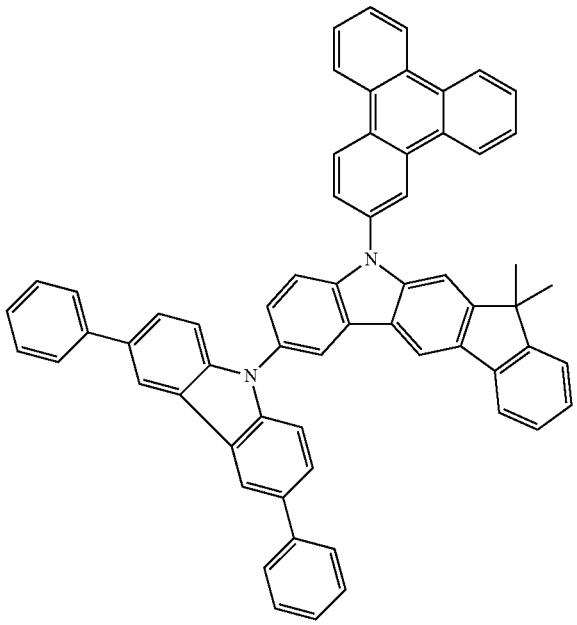
(155)
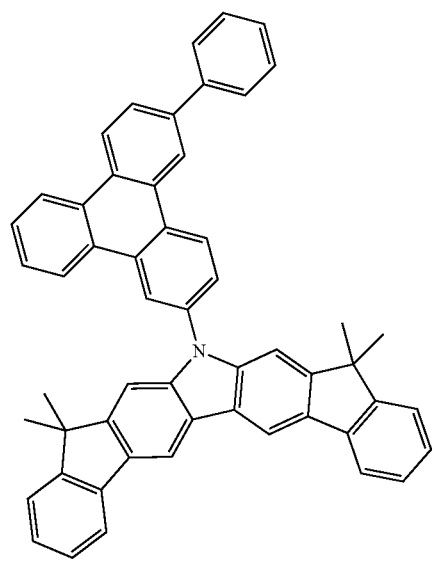
(156)
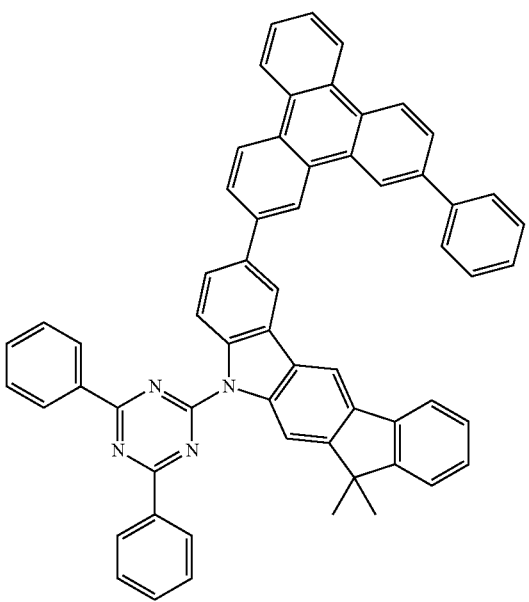

-continued
(157)
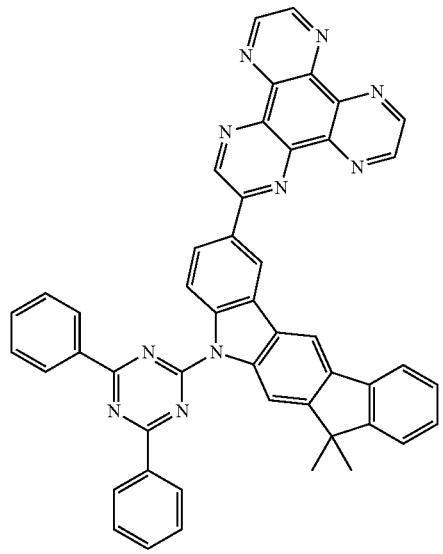
(158)
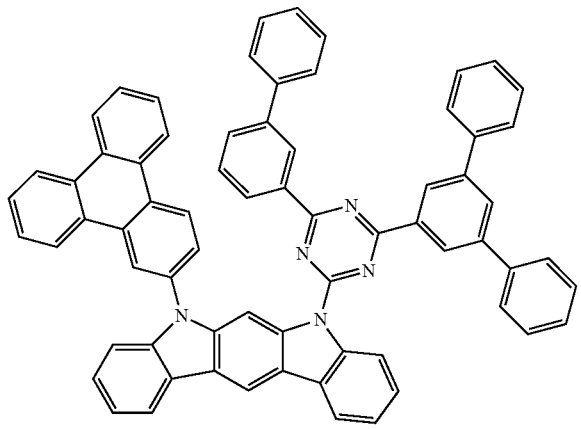
(159)
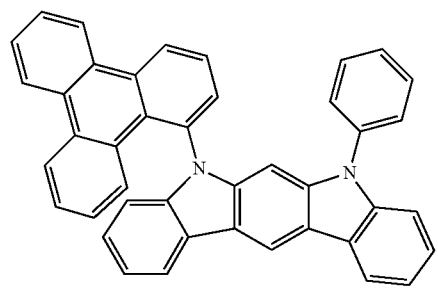
(160)
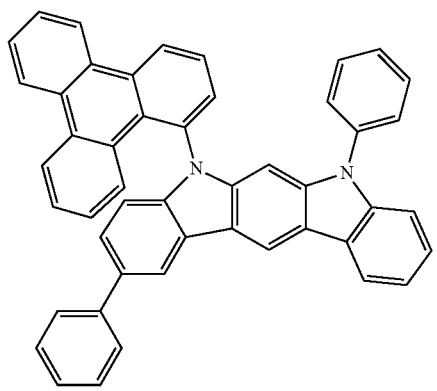
(161)
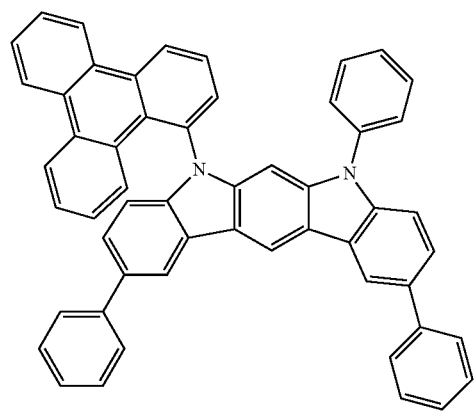
(162)
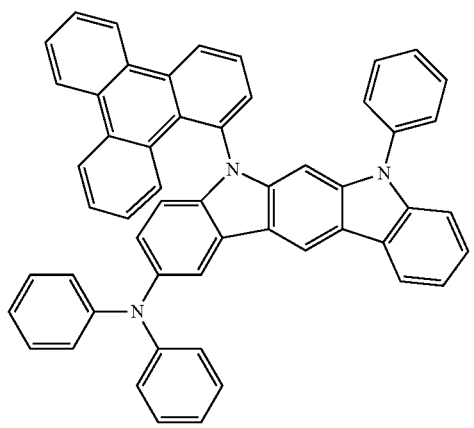

-continued
(163)
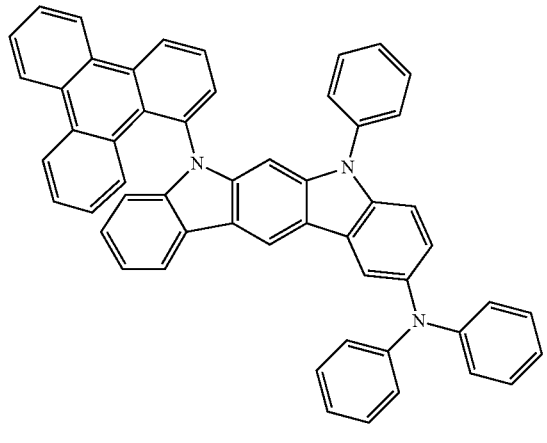
(164)
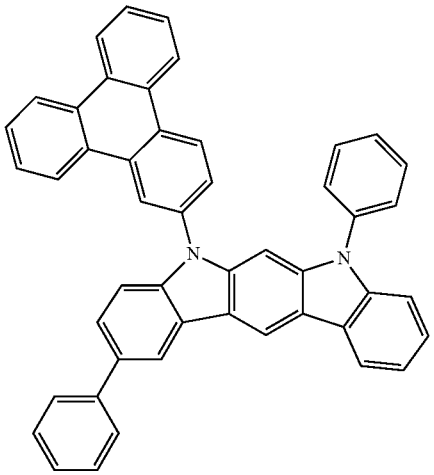
(165)
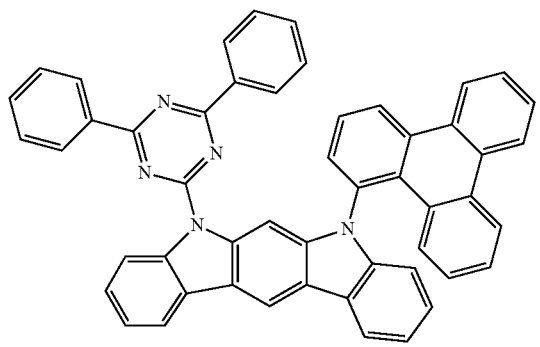
(166)
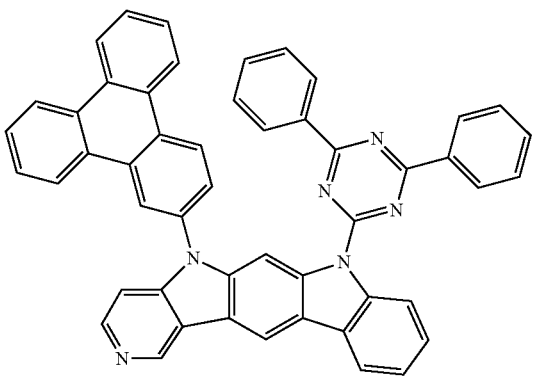
(167)
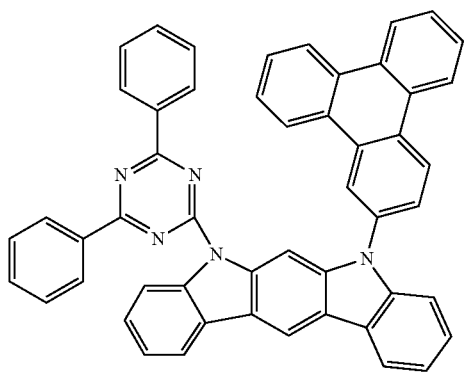
(168)
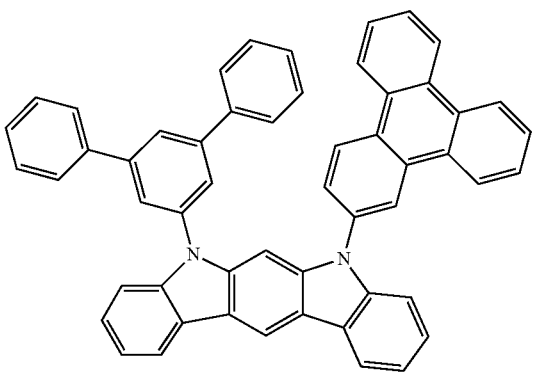

-continued
(169)
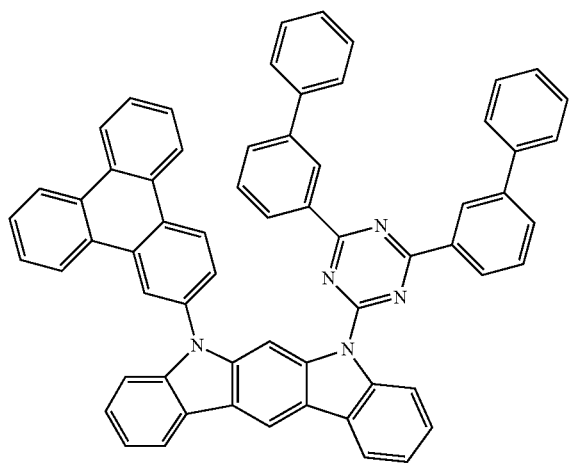
(170)
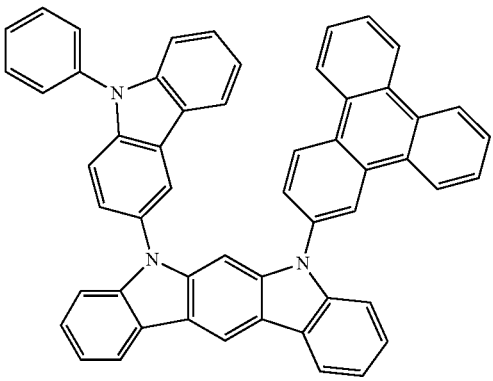
(171)
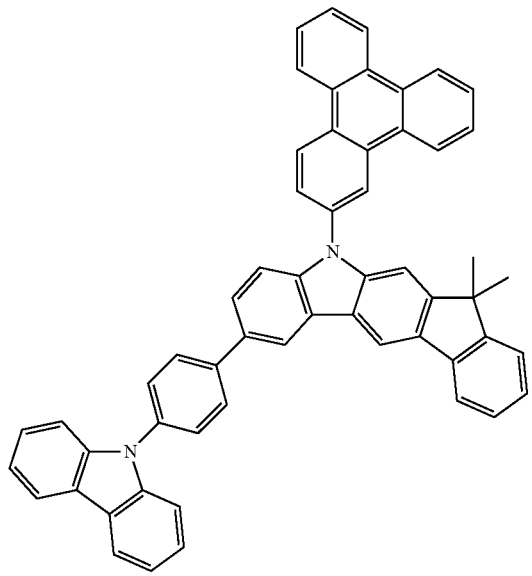
(172)
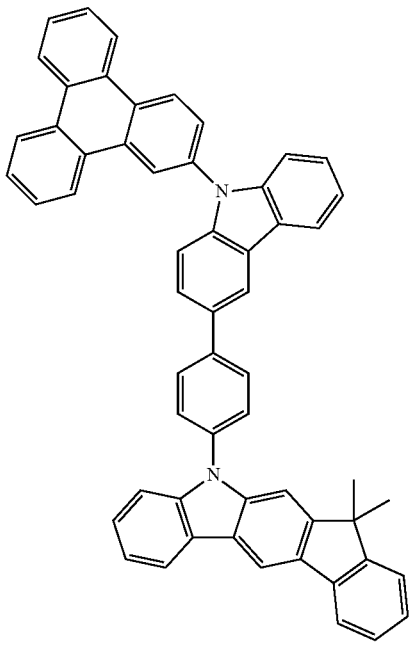
(173)
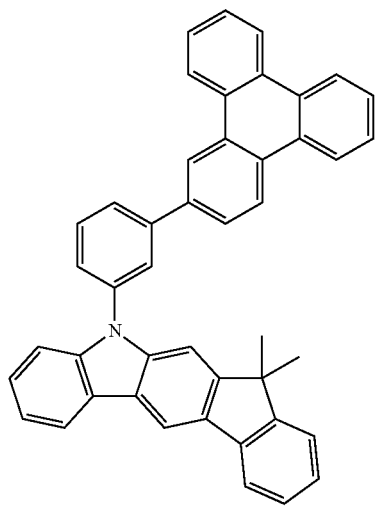
(174)
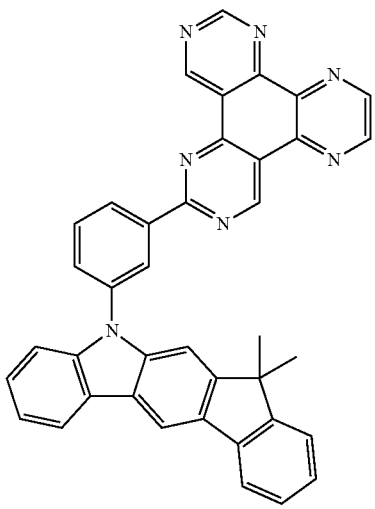

-continued
(175)
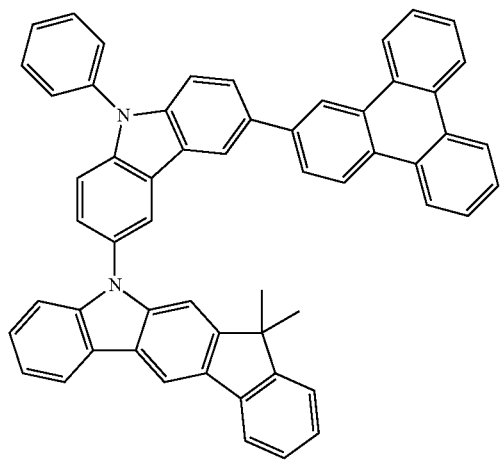
(176)
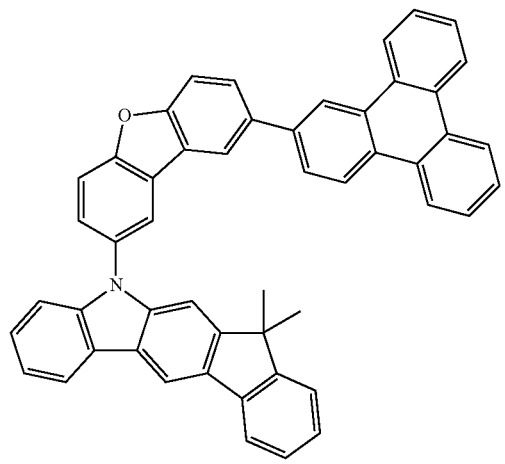
(177)
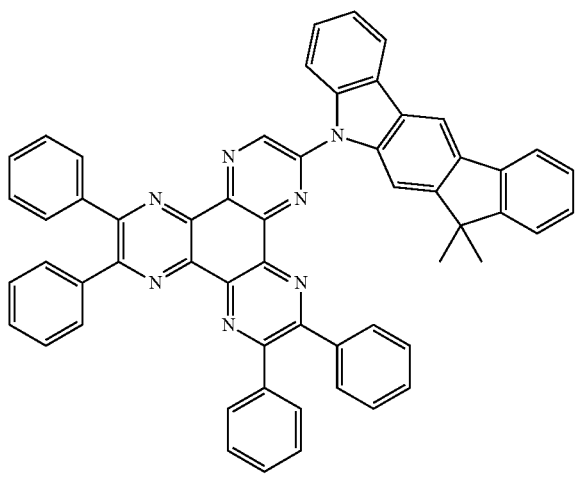
(178)
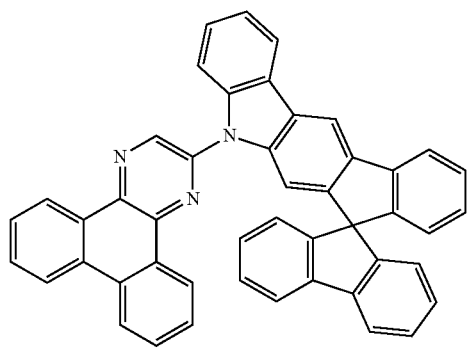
(179)
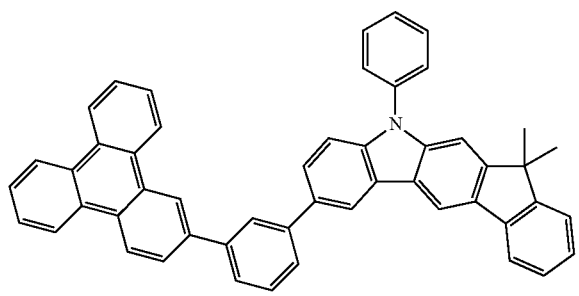
(180)
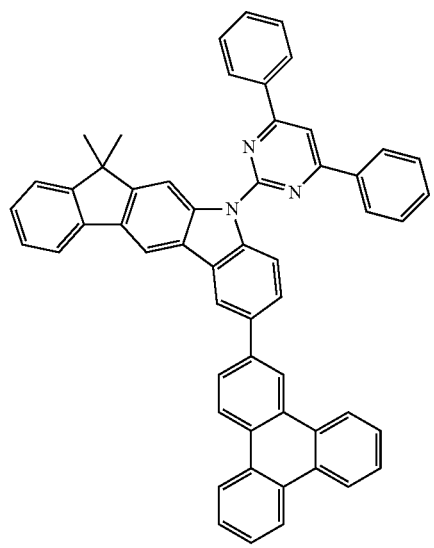

(181)
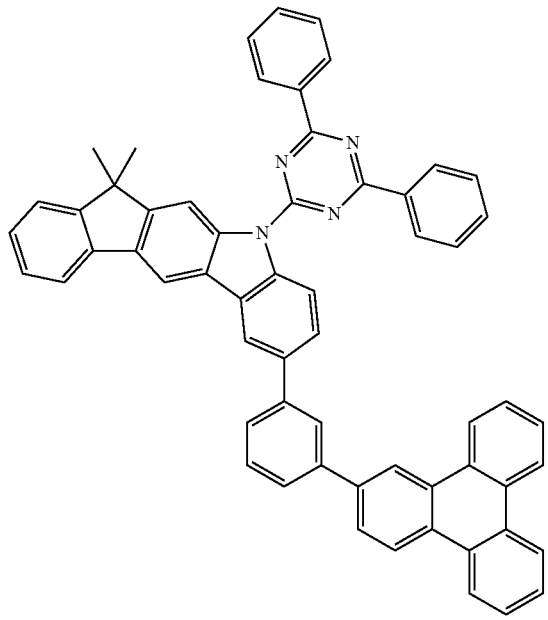
(182)
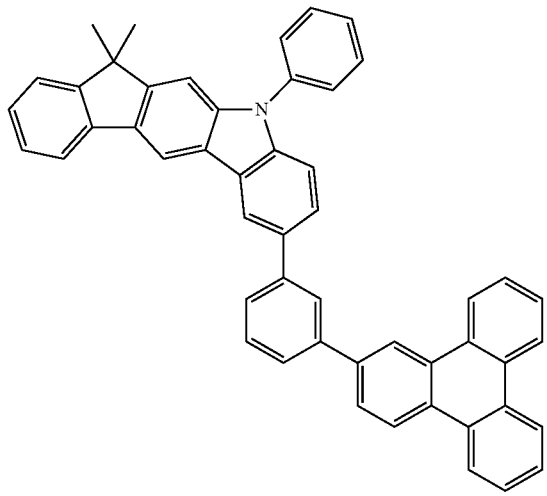
(183)
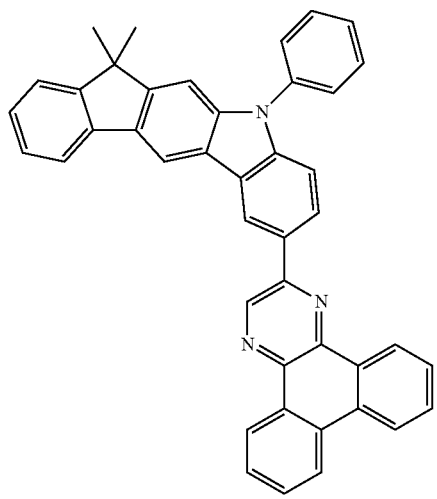
(184)
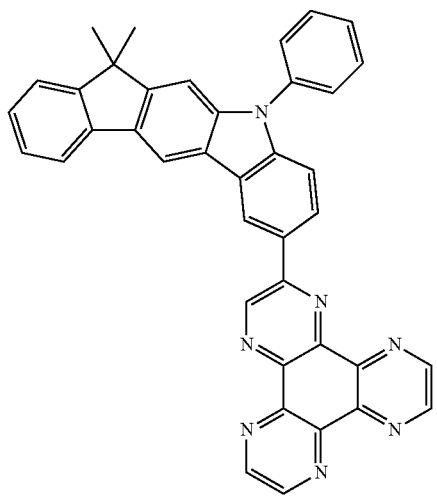

(185)
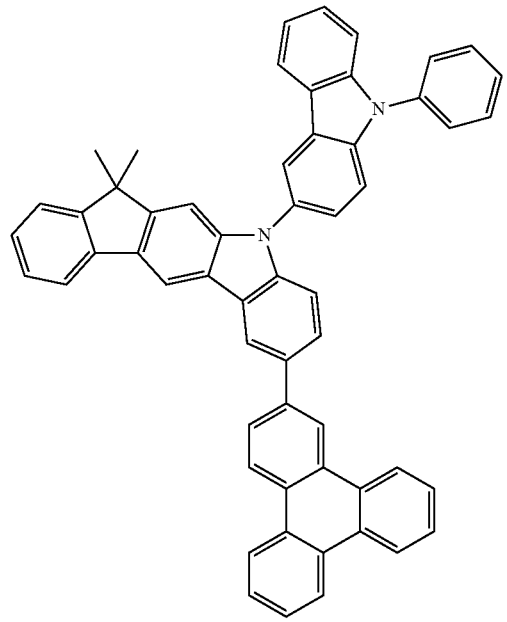
(186)
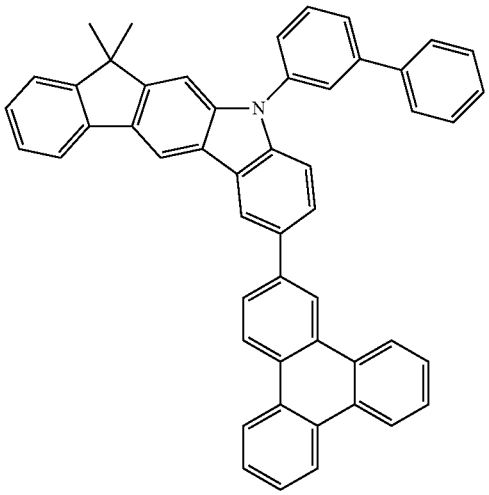
(187)
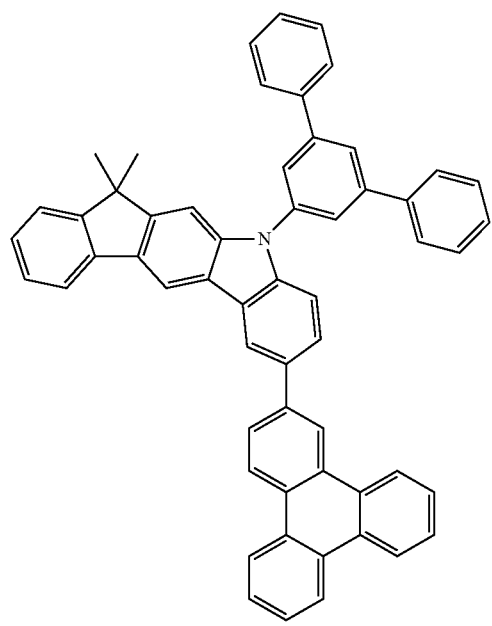
(188)
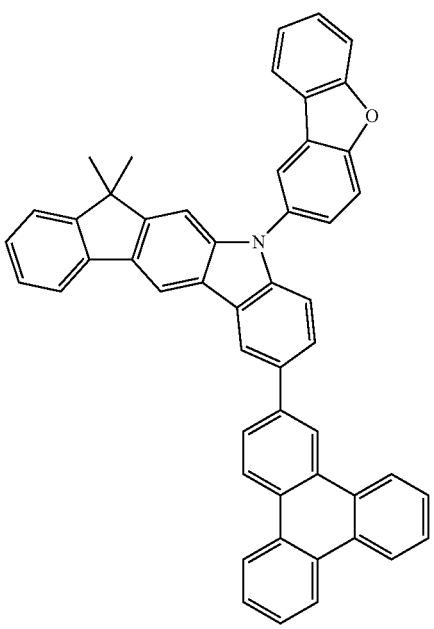

-continued (189)
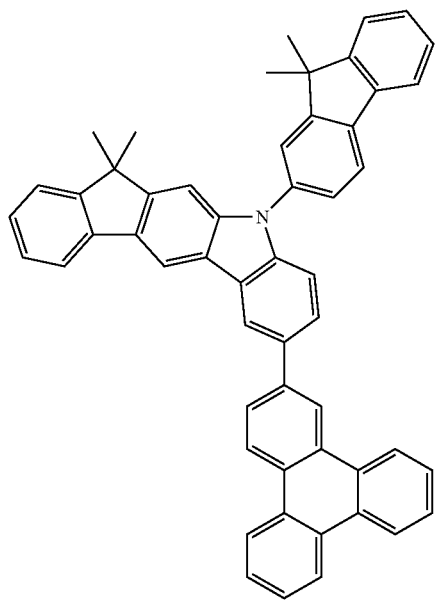

(190)
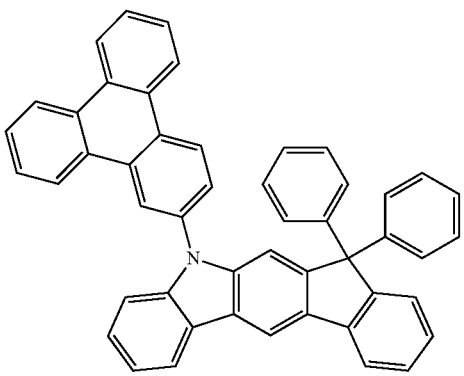

(191)
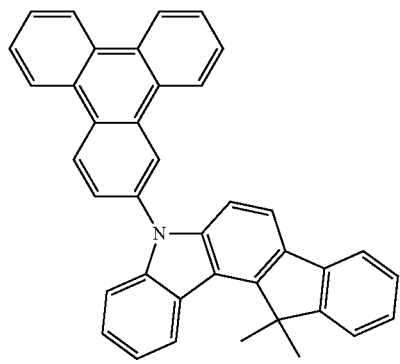

(192)
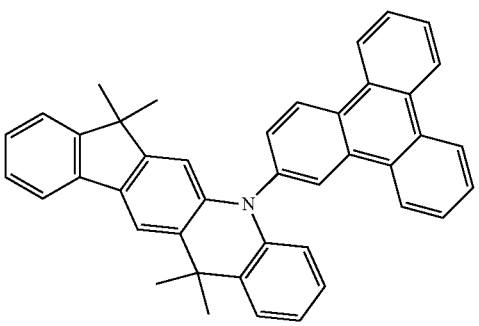

(193)
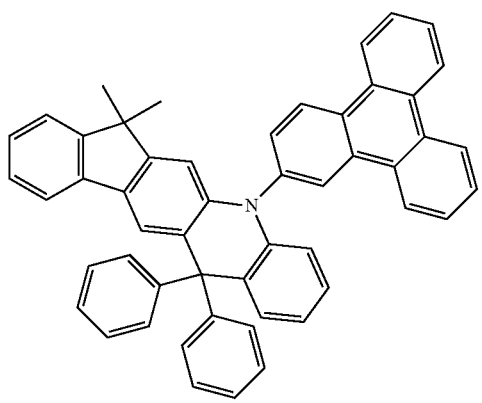

The compounds according to the invention can be prepared by synthesis steps known to the person skilled in the art, such as, for example, bromination, Suzuki coupling, Hartwig-Buchwald coupling, etc. The synthesis of a compound of the formula (1), formula (2), formula (3) or formula (4) in which the group of the formula (5) is bonded to the nitrogen atom is shown diagrammatically in Scheme 1, where the introduction of the triphenylene group preferably takes place via a Hartwig-Buchwald coupling with palladium catalysis.

Scheme 1:

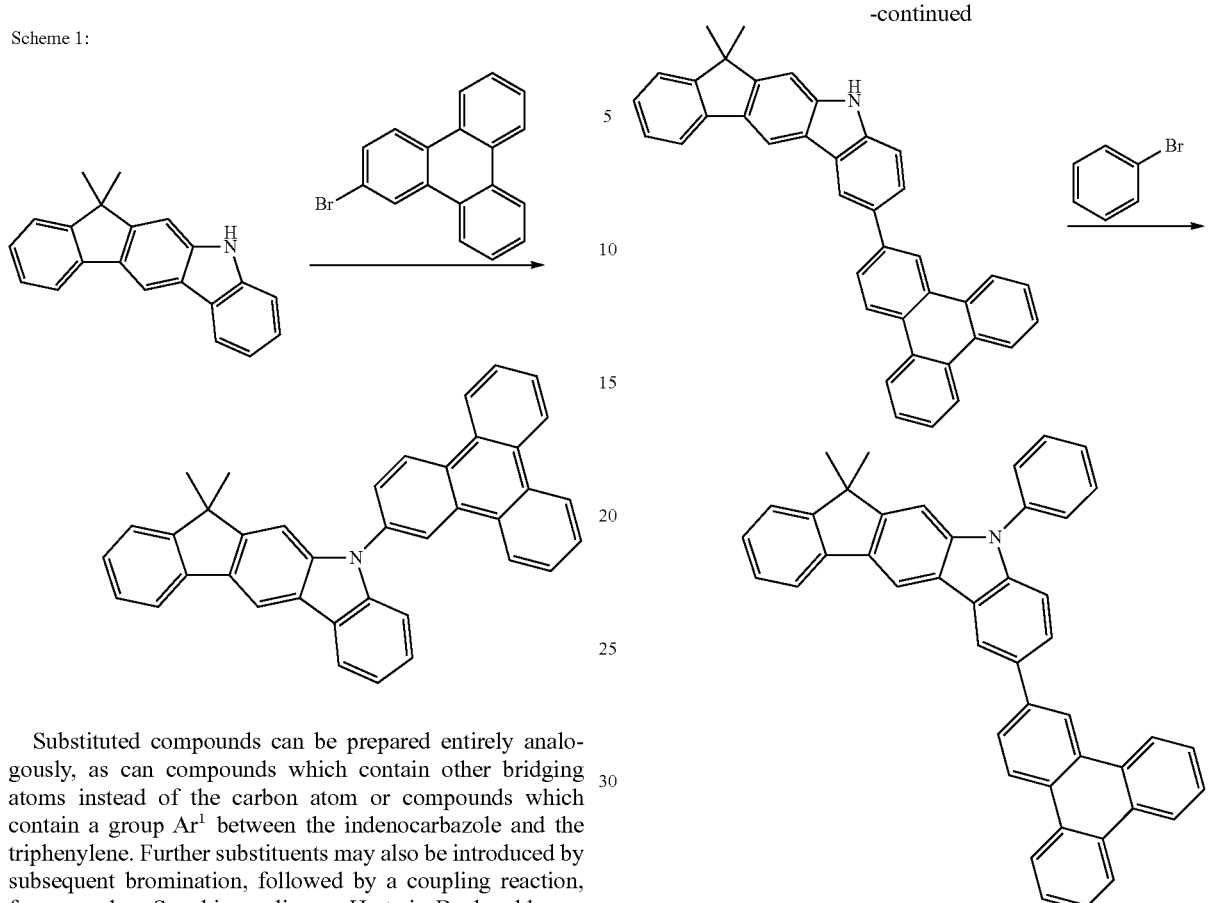

Substituted compounds can be prepared entirely analogously, as can compounds which contain other bridging atoms instead of the carbon atom or compounds which contain a group Ar¹ between the indenocarbazole and the triphenylene. Further substituents may also be introduced by subsequent bromination, followed by a coupling reaction, for example a Suzuki coupling or Hartwig-Buchwald coupling.

If the group of the formula (5) is not bonded to the nitrogen atom, but instead to the indenocarbazole skeleton, a Suzuki coupling, for example, is suitable for the introduction of this group, as shown in Scheme 2.

Scheme 2:

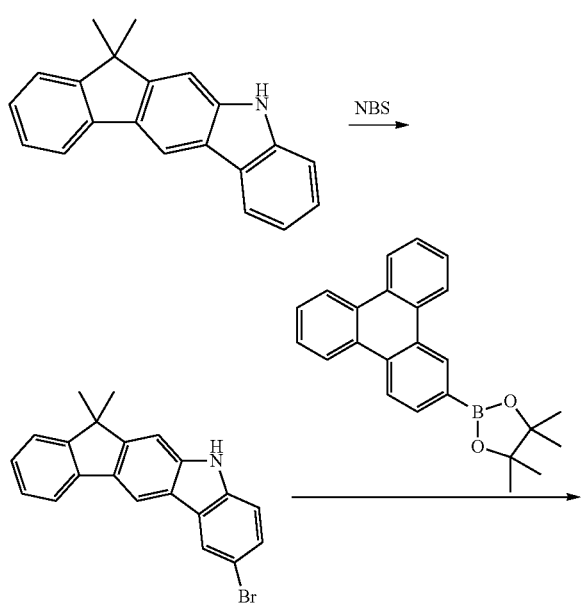

Substituted compounds can be prepared entirely analogously, as can compounds which contain other bridging atoms instead of the carbon atom or nitrogen atom or compounds which contain a group Ar¹ between the indenocarbazole and the triphenylene.

The invention furthermore relates to a process for the preparation of a compound according to the invention, characterised by the steps:
a) synthesis of the skeleton of the formula (1), (2), (3) or (4) which does not yet contain a group of the formula (5); and
b) introduction of the group of the formula (5) by a metal-catalysed coupling reaction.

Suitable as metal-catalysed coupling reaction are, for example, Hartwig-Buchwald, Suzuki, Negishi, Kumada, Stille couplings and other coupling reactions.

The present invention furthermore relates to mixtures comprising at least one compound according to the invention and at least one further compound. The further compound can be, for example, a fluorescent or phosphorescent dopant if the compound according to the invention is used as matrix material, in particular a phosphorescent dopant. Suitable dopants are indicated below in connection with the organic electroluminescent devices and are also preferred for the mixtures according to the invention.

For processing from solution or from the liquid phase, for example by spin coating or by printing processes, solutions or formulations of the compounds or mixtures according to the invention are necessary. It may be preferred to use mixtures of two or more solvents. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents.

The present invention therefore furthermore relates to a formulation, in particular a solution, a suspension or a mini-emulsion, comprising at least one compound or mixture according to the invention and one or more solvents, in particular organic solvents. The way in which solutions of this type can be prepared is known to the person skilled in the art and described, for example, in WO 2002/072714, WO 2003/019694 and the literature cited therein.

The compounds and mixtures according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds or mixtures according to the invention in an electronic device, in particular in an organic electroluminescent device.

The present invention still furthermore relates to an electronic device comprising at least one of the compounds or mixtures according to the invention mentioned above. The preferences stated above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells, organic optical detectors, organic photoreceptors, organic field-quench devices (O-FQDs), light-emitting electrochemical cells (LECs), organic laser diodes (O-lasers) and "organic plasmon emitting devices" (D. M. Koller et al., *Nature Photonics* 2008, 1-4), preferably organic electroluminescent devices (OLEDs, PLEDs), in particular phosphorescent OLEDs.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer, or it may comprise a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). These can be fluorescent or phosphorescent emission layers or hybrid systems, in which fluorescent and phosphorescent emission layers are combined with one another.

The compound according to the invention in accordance with the embodiments indicated above can be employed in various layers, depending on the precise structure. Preference is given to an organic electroluminescent device comprising a compound of the formula (1), formula (2), formula (3), formula (4) or in accordance with the preferred embodiments as matrix material for fluorescent or phosphorescent emitters, in particular for phosphorescent emitters, and/or in a hole-blocking layer and/or in an electron-transport layer and/or in an electron-blocking or exciton-blocking layer and/or in a hole-transport layer, depending on the precise substitution. The preferred embodiments indicated above also apply to the use of the materials in organic electronic devices.

In a preferred embodiment of the invention, the compound of the formula (1), formula (2), formula (3), formula (4) or in accordance with the preferred embodiments is employed as matrix material for a fluorescent or phosphorescent compound, in particular for a phosphorescent compound, in an emitting layer. The organic electroluminescent device here may comprise one emitting layer, or it may comprise a plurality of emitting layers, where at least one emitting layer comprises at least one compound according to the invention as matrix material.

If the compound of the formula (1), formula (2), formula (3), formula (4) or in accordance with the preferred embodiments is employed as matrix material for an emitting compound in an emitting layer, it is preferably employed in combination with one or more phosphorescent materials (triplet emitters). Phosphorescence in the sense of this invention is taken to mean the luminescence from an excited state having relatively high spin multiplicity, i.e. a spin state>1, in particular from an excited triplet state. For the purposes of this application, all luminescent transition-metal complexes and luminescent lanthanide complexes, in particular all iridium, platinum and copper complexes, are to be regarded as phosphorescent compounds.

The mixture comprising the compound of the formula (1), formula (2), formula (3), formula (4) or in accordance with the preferred embodiments and the emitting compound comprises between 99 and 1% by vol., preferably between 98 and 10% by vol., particularly preferably between 97 and 60% by vol., in particular between 95 and 80% by vol., of the compound of the formula (1), formula (2), formula (3), formula (4) or in accordance with the preferred embodiments, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound of the formula (1), formula (2), formula (3), formula (4) or in accordance with the preferred embodiments as matrix material for a phosphorescent emitter in combination with a further matrix material. Particularly suitable matrix materials which can be employed in combination with the compounds of the formula (1), formula (2), formula (3), formula (4) or in accordance with the preferred embodiments are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 and WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or in accordance with the unpublished application EP 11003232.3, triphenylene derivatives, for example in accordance with the unpublished DE 102010048608.6, or lactams, for example in accordance with WO 2011/116865 and the unpublished application DE 102010019306.2. A further phosphorescent emitter which emits at shorter wavelength than the actual emitter may likewise be present in the mixture as co-host.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum. For the purposes of the present invention, all luminescent compounds which contain the above-mentioned metals are regarded as phosphorescent compounds.

Examples of the emitters described above are revealed by the applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626 and WO 2011/066898. Furthermore suitable are the complexes in accordance with the unpublished applications EP 10006208.2 and DE 102010027317.1. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

In a further preferred embodiment of the invention, the compound of the formula (1), formula (2), formula (3), formula (4) or in accordance with the preferred embodiments is employed as electron-transport material in an electron-transport or electron-injection layer.

In still a further preferred embodiment of the invention, the compound of the formula (1), formula (2), formula (3), formula (4) or in accordance with the preferred embodiments is employed in a hole-blocking layer.

It is furthermore possible to use the compound of the formula (1), formula (2), formula (3), formula (4) or in accordance with the preferred embodiments both in a hole-blocking layer or electron-transport layer and also as matrix in an emitting layer.

In the further layers of the organic electroluminescent device according to the invention, it is possible to use all materials as usually employed in accordance with the prior art. The person skilled in the art can therefore, without inventive step, all materials known for organic electroluminescent devices in combination with the compounds of the formula (1), formula (2), formula (3), formula (4) or in accordance with the preferred embodiments.

Preference is furthermore given to an organic electroluminescent device, characterised in that one or more layers are coated by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower or higher, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, ink-jet printing, LITI (light induced thermal imaging, thermal transfer printing), screen printing, flexographic printing, offset printing or nozzle printing. Soluble compounds, which are obtained, for example, by suitable substitution, are necessary for this purpose. These processes are also particularly suitable for oligomers, dendrimers and polymers.

Also possible are hybrid processes, in which, for example, one or more layers are applied from solution and one or more further layers are applied by vapour deposition. Thus, it is possible, for example, to apply the emitting layer from solution and to apply the electron-transport layer by vapour deposition.

These processes are generally known to the person skilled in the art and can be applied by him without inventive step to organic electroluminescent devices comprising the compounds according to the invention.

The compounds according to the invention have the following surprising advantages over the prior art on use in organic electroluminescent devices:
1. The power efficiency of corresponding devices increases compared with systems in accordance with the prior art.
2. The stability of corresponding devices increases compared with systems in accordance with the prior art, which is evident, in particular, in a significantly longer lifetime.
3. At the same time, the organic electroluminescent devices according to the invention have a reduced operating voltage.
4. The organic electroluminescent devices according to the invention have very high efficiency. The improved efficiency is possibly attributable to improved electron injection from the electron-transport layer into the emitting layer.

The invention is now explained in greater detail by the following examples, without wishing to restrict it thereby.

EXAMPLES

The following syntheses are carried out, unless indicated otherwise, in dried solvents under a protective-gas atmosphere. The solvents and reagents can be purchased, for example, from Sigma-ALDRICH or ABCR. The corresponding CAS numbers are also indicated for each of the compounds known from the literature.

Example 1

Synthesis of Compound B1

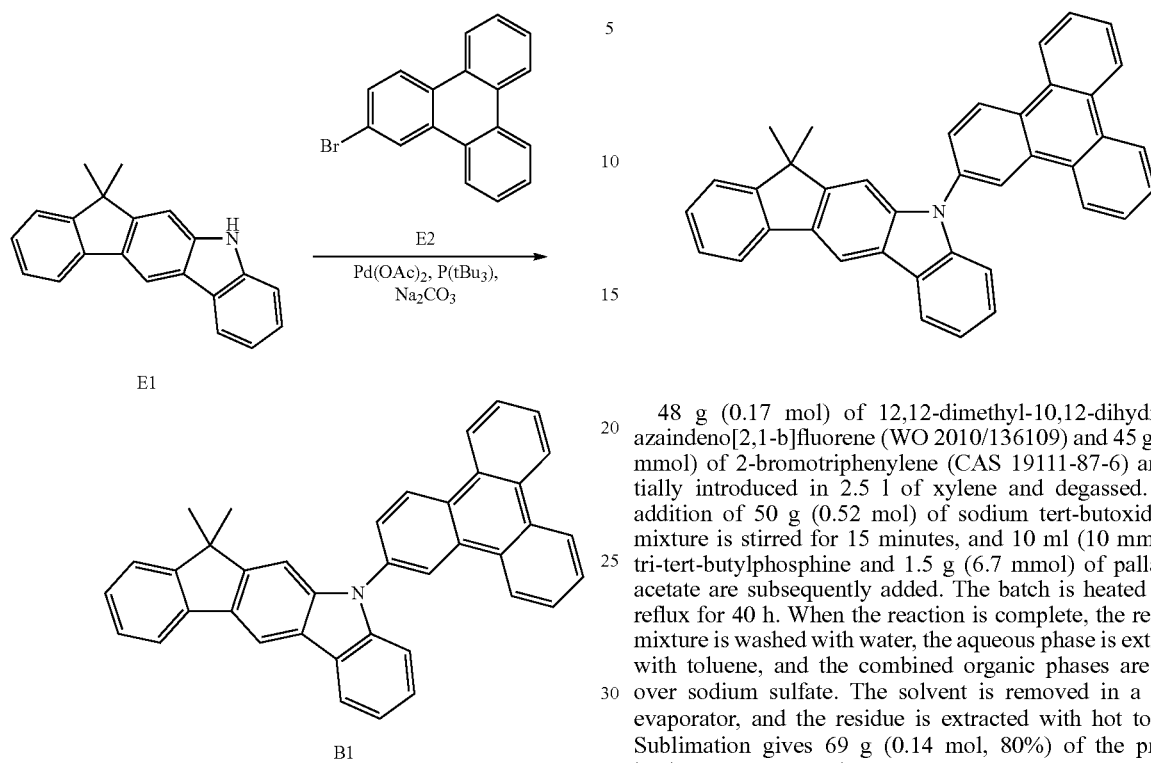

B1: 12,12-Dimethyl-10-triphenylen-2-yl-10,12-di-hydro-10-azaindeno-[2,1-b]fluorene 48 g (0.17 mol) of 12,12-dimethyl-10,12-dihydro-10-azaindeno[2,1-b]fluorene (WO 2010/136109) and 45 g (0.16 mmol) of 2-bromotriphenylene (CAS 19111-87-6) are initially introduced in 2.5 l of xylene and degassed. After addition of 50 g (0.52 mol) of sodium tert-butoxide, the mixture is stirred for 15 minutes, and 10 ml (10 mmol) of tri-tert-butylphosphine and 1.5 g (6.7 mmol) of palladium acetate are subsequently added. The batch is heated under reflux for 40 h. When the reaction is complete, the reaction mixture is washed with water, the aqueous phase is extracted with toluene, and the combined organic phases are dried over sodium sulfate. The solvent is removed in a rotary evaporator, and the residue is extracted with hot toluene. Sublimation gives 69 g (0.14 mol, 80%) of the product having an HPLC purity>99.9%.

The following compounds are prepared analogously:

| Ex. | Starting materials | Starting material 2 | Product | Yield |
|---|---|---|---|---|
| B2 | WO 2010/136109 | CAS 19111-87-6 | | 76% |
| B3 | WO 2010/136109 | 0.5 equivalents: CAS 888041-37-0 | | 71% |

-continued

| Ex. | Starting materials | Starting material 2 | Product | Yield |
|---|---|---|---|---|
| B4 | WO 2010/136109 | CAS 24253-52-9 | | 85% |
| B5 | WO 2010/136109 | 0.5 equivalents: CAS 24253-51-8 | | 78% |
| B6 | WO 2010/136109 | CAS 19111-87-6 | | 91% |
| B7 | CAS 1246308-83-7 | CAS 19111-87-6 | | 85% |

| Ex. | Starting materials | Starting material 2 | Product | Yield |
|---|---|---|---|---|
| B8 | 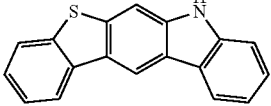<br>CAS 1255309-04-6 | 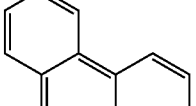<br>CAS 19111-87-6 | 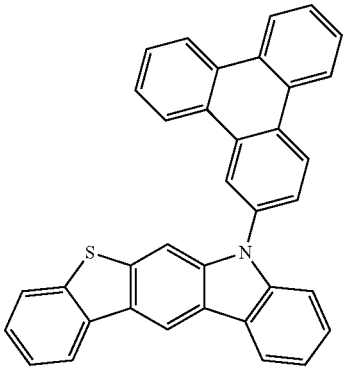 [SMILES: c1ccc2c(c1)sc1cc3c(cc12)c1ccccc1n3-c1ccc2c3ccccc3c3ccccc3c2c1] | 87% |
| B9 | 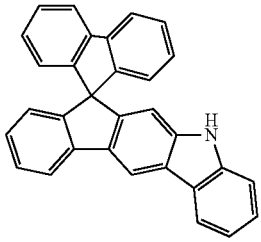<br>WO 2010/136109 | 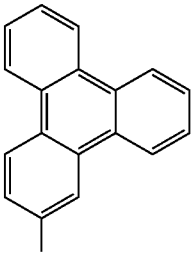<br>CAS 19111-87-6 | 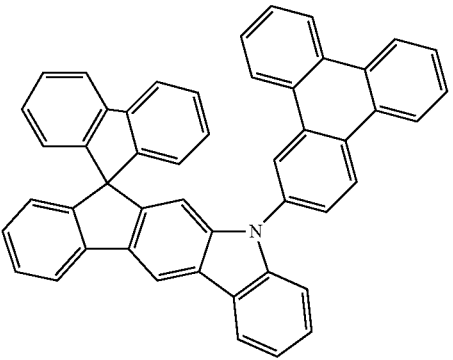 [SMILES: c1ccc2c(c1)-c1ccccc1C21c2ccccc2-c2cc3c4ccccc4n(-c4ccc5c6ccccc6c6ccccc6c5c4)c3cc21] | 75% |
| B10 | 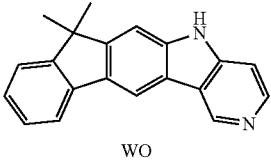<br>WO 2010/136109 | 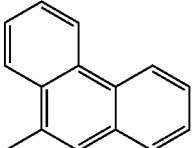<br>CAS 19111-87-6 | 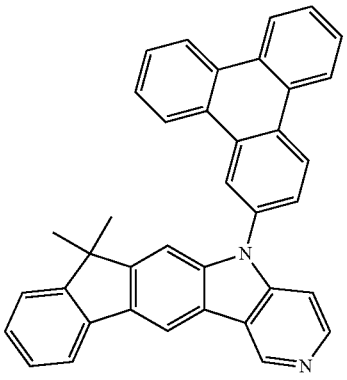 [SMILES: CC1(C)c2ccccc2-c2cc3c4cnccc4n(-c4ccc5c6ccccc6c6ccccc6c5c4)c3cc21] | 88% |
| B11 | 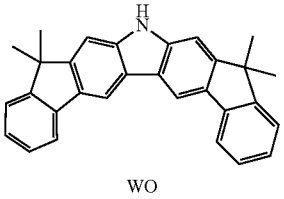<br>WO 2010/136109 | 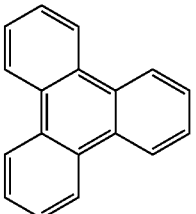<br>CAS 19111-87-6 | 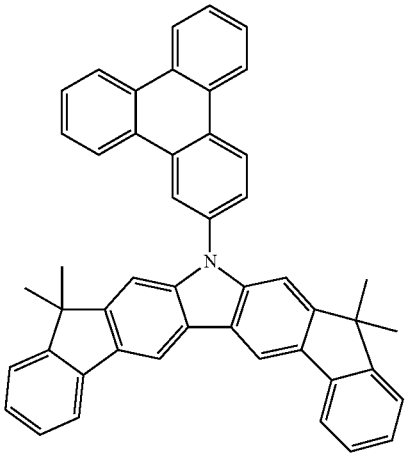 [SMILES: CC1(C)c2ccccc2-c2cc3c4cc5c(cc4n(-c4ccc6c7ccccc7c7ccccc7c6c4)c3cc21)C(C)(C)c1ccccc1-5] | 92% |

| Ex. | Starting materials | Starting material 2 | Product | Yield |
|---|---|---|---|---|
| B12 | WO 2010/136109 | 2 equivalents:<br>CAS 19111-87-6 | | 73% |
| B13 | WO 2010/136109 | CAS 1202564-31-5 | | 84% |
| B14 | WO 2010/136109 | CAS 1182724-82-8 | | 89% |
Example 15
Synthesis of Compound B15
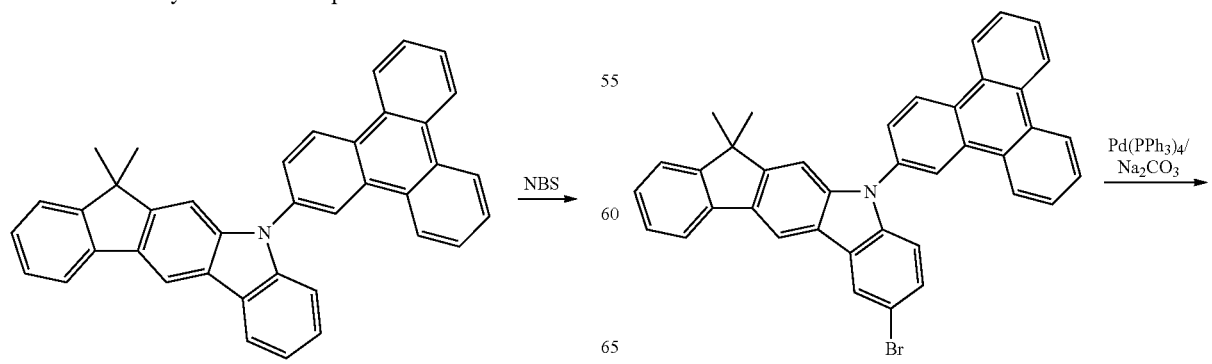

-continued

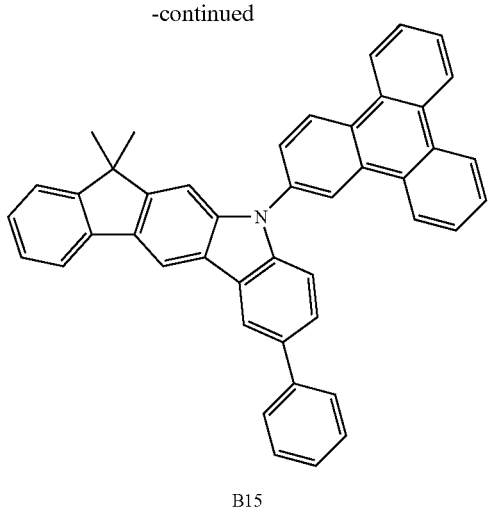

B15

Step 1: 7-Bromo-12,12-dimethyl-10-triphenylen-2-yl-10,12-dihydro-10-azaindeno[2,1-b]fluorene

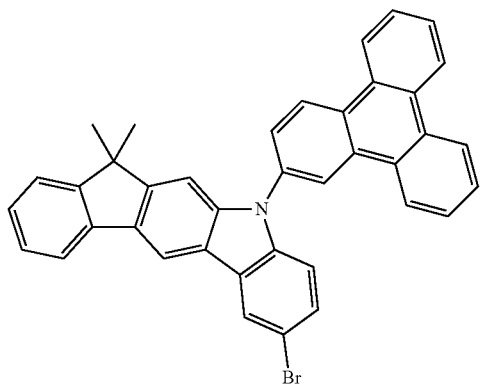 [SMILES: CC1(C)c2ccccc2-c2cc3c4cc(Br)ccc4n(-c4ccc5c6ccccc6c6ccccc6c5c4)c3cc21]

67.0 g (114 mmol) of 12,12-dimethyl-10-triphenylen-2-yl-10,12-dihydro-10-azaindeno[2,1-b]fluorene are initially introduced in 500 ml of acetonitrile. A solution of 20.3 g (114 mmol) of NBS in 250 ml of CH₃CN is subsequently added dropwise at −15° C. with exclusion of light, the mixture is allowed to come to room temperature and is stirred at this temperature for a further 4 h. 75 ml of water are subsequently added to the mixture, which is then extracted with CH₂Cl₂. The organic phase is dried over MgSO₄, and the solvents are removed in vacuo. The product is washed by stirring with hot hexane and filtered off with suction. Yield: 38.7 g (66.1 mmol, 58%), purity according to ¹H-NMR about 96%.

Step 2: 12,12-Dimethyl-7-phenyl-10-triphenylen-2-yl-10,12-dihydro-10-azaindeno[2,1-b]fluorene (B15)

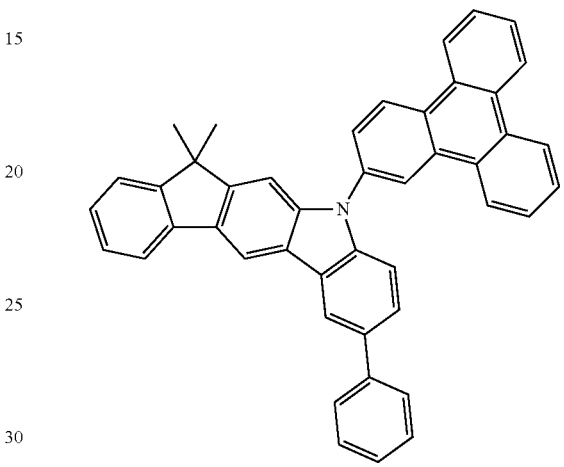

3.5 g (17 mmol) of 4,4,5,5-tetramethyl-2-phenyl-1,3,2-dioxaborolane, 10 g (17 mmol) of 7-bromo-12,12-dimethyl-10-triphenylen-2-yl-10,12-dihydro-10-azaindeno[2,1-b]fluorene and 2.7 g of sodium carbonate are suspended in 200 ml of dioxane, 200 ml of toluene and 100 ml of water. 0.98 g (0.84 mmol) of Pd(PPh₃)₄ are added to this suspension. The reaction mixture is heated under reflux for 5 h. After cooling, the precipitated solid is filtered off with suction, washed with water and ethanol and dried. The residue is extracted with hot toluene and recrystallised from toluene/heptane. Sublimation gives 7.8 g (13 mmol, 79%) of the product having an HPLC purity>99.9%.

The following compounds are prepared analogously:

| Ex. | Starting material | Product | Yield |
|---|---|---|---|
| B15 | HO-B-OH pyridin-2-yl<br>CAS 197958-29-5 | [structure] | 83% |

| Ex. | Starting material | Product | Yield |
|---|---|---|---|
| B16 | 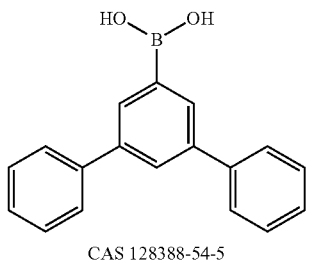 [SMILES: OB(O)c1cc(-c2ccccc2)cc(-c2ccccc2)c1]CAS 128388-54-5 | 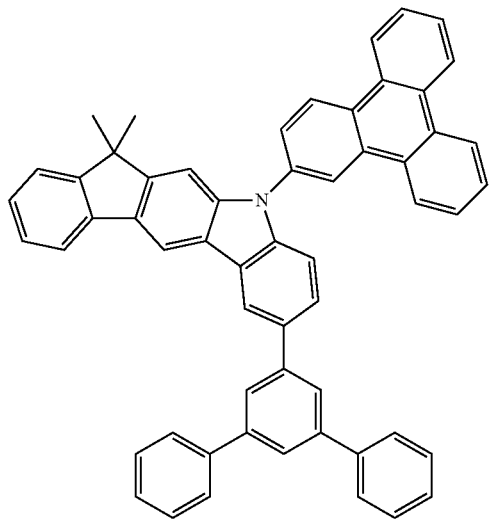 | 88% |
| B17 | 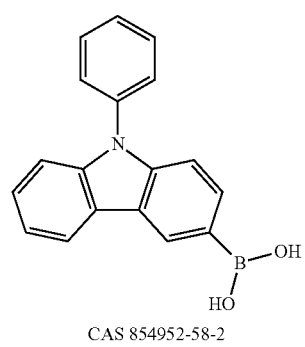 [SMILES: OB(O)c1ccc2c(c1)c1ccccc1n2-c1ccccc1]CAS 854952-58-2 | 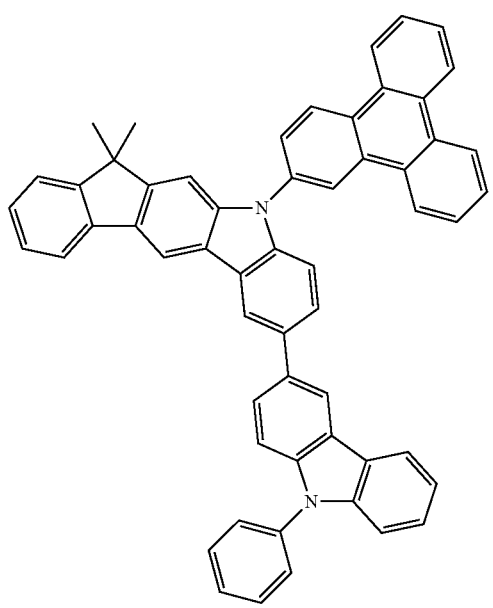 [SMILES: CC1(C)c2ccccc2-c2cc3c4cc(-c5ccc6c(c5)c5ccccc5n6-c5ccccc5)ccc4n(-c4ccc5c6ccccc6c6ccccc6c5c4)c3cc21] | 90% |

| Ex. | Starting material | Product | Yield |
|---|---|---|---|
| B18 | 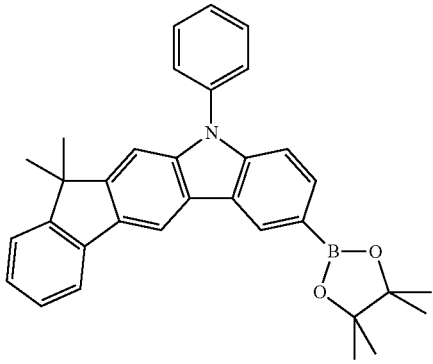 S1 | 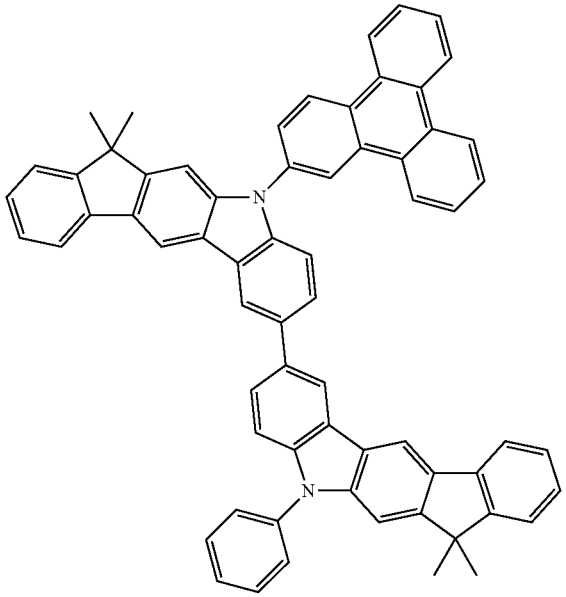 [SMILES: CC1(C)c2ccccc2-c2cc3c4cc(-c5ccc6c(c5)c5cc7c(cc5n6-c5ccc6c8ccccc8c8ccccc8c6c5)C(C)(C)c5ccccc5-7)ccc4n(-c4ccccc4)c3cc21] | 78% |
| B19 | 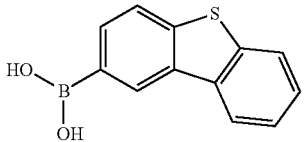 CAS 668983-97-9 | 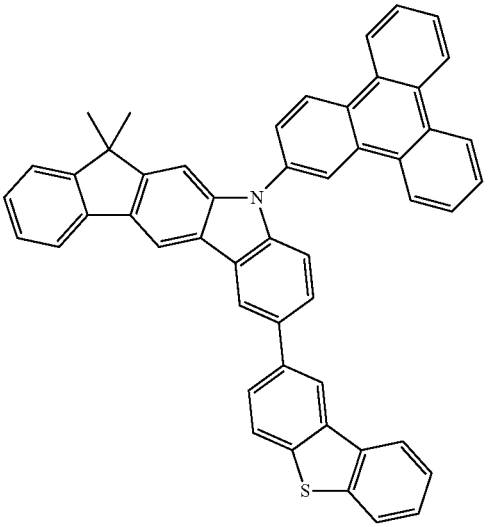 [SMILES: CC1(C)c2ccccc2-c2cc3c4cc(-c5ccc6sc7ccccc7c6c5)ccc4n(-c4ccc5c6ccccc6c6ccccc6c5c4)c3cc21] | 91% |

Preparation of synthone S1 for B18: 12,12-Dimethyl-10-phenyl-7-(4,4,5,5-tetramethyl-1,3,2-dioxaborolan-2-yl)-10,12-di hydro-10-azaindeno[2,1-b]fluorene

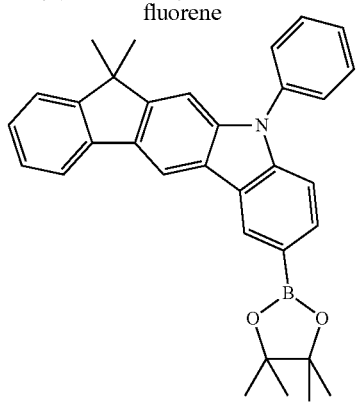

24 g (55 mmol) of 7-bromo-12,12-dimethyl-10-phenyl-10,12-dihydro-10-azaindeno[2,1-b]fluorene (WO2010136109), 15.5 g (60 mmol) of bis(pinacolato)diborane and 16 g (160 mmol) of potassium acetate are suspended in 200 ml of dioxane. 1.3 g (1.7 mmol) of 1,1-bis(diphenylphosphino)-ferrocenepalladium(II) dichloride complex with dichloromethane are added to this suspension. The reaction mixture is heated under reflux for 7 h. After cooling, the organic phase is separated off, washed three times with 100 ml of water each time and subsequently evaporated to dryness. The residue is recrystallised from toluene (22 g, 45 mmol, 82%).

B20: 7-Carbazol-9-yl-12,12-dimethyl-10-triphenylen-2-yl-10,12-dihydro-10-azaindeno[2,1-b]fluorene

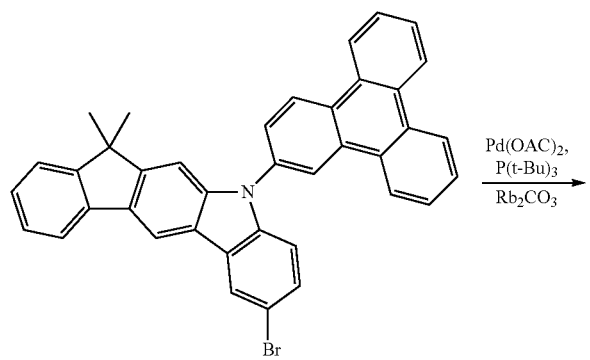

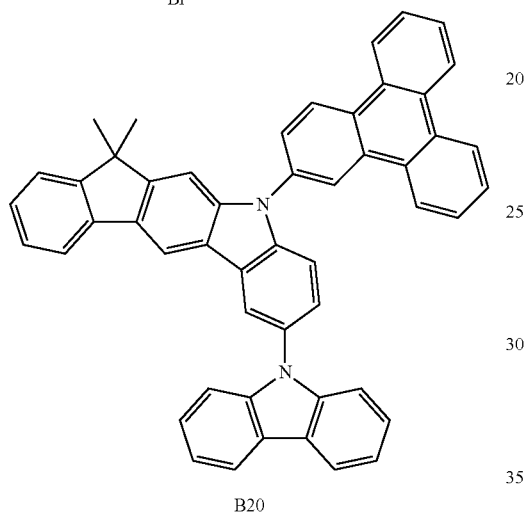

B20

10 g (17 mmol) of 7-bromo-12,12-dimethyl-10-triphenylen-2-yl-10,12-dihydro-10-azaindeno[2,1-b]fluorene (synthesis: see above), 9.2 g (19 mmol) of carbazole and 11.8 g of $Rb_2CO_3$ are suspended in 125 ml of p-xylene. 0.38 g (1.7 mmol) of $Pd(OAc)_2$ and 5.1 ml of a 1M tri-tert-butylphosphine solution are added to this suspension. The reaction mixture is heated under reflux for 16 h. After cooling, the organic phase is separated off, washed three times with 75 ml of water and subsequently evaporated to dryness. The residue is extracted with hot toluene, recrystallised from toluene/heptane. Sublimation gives 9.4 g (14 mmol, 82%) of the product having an HPLC purity>99.9%.

The following compounds are prepared analogously:

| Ex. | Starting material | Product | Yield |
|---|---|---|---|
| B21 | 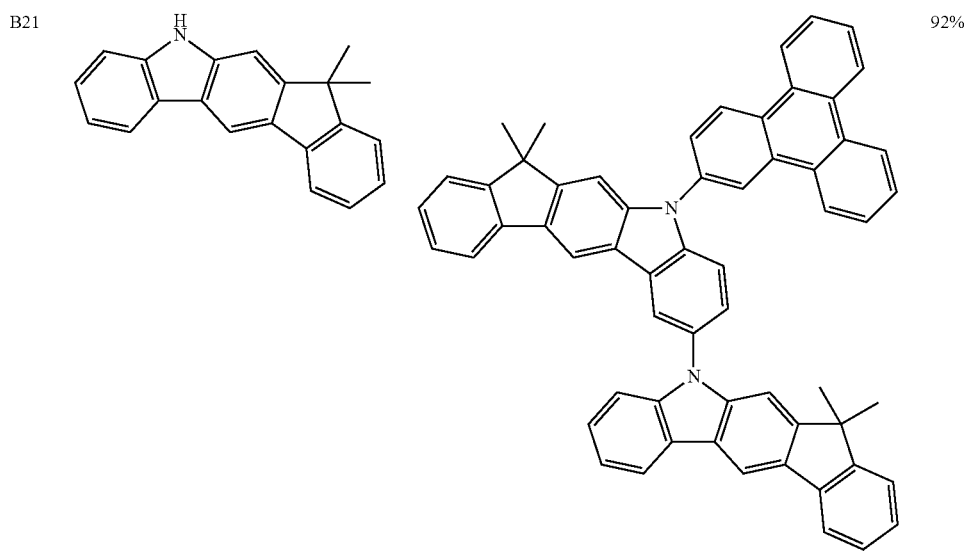 | | 92% |

| Ex. | Starting material | Product | Yield |
|---|---|---|---|
| B22 | | | 87% |
| B23 | | | 74% |
Synthesis of B24
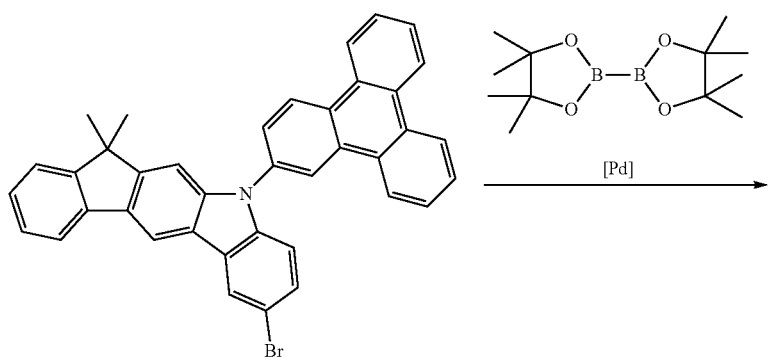

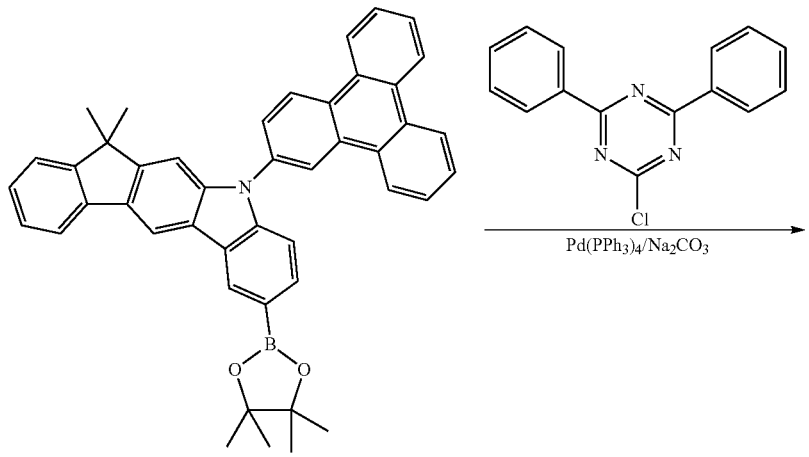

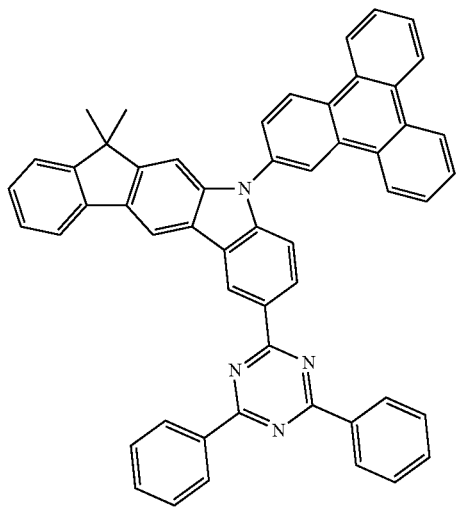

B24

Step 1: 12,12-Dimethyl-7-(4,4,5,5-tetramethyl-1,3,2-dioxaborolan-2-yl)-10-triphenylen-2-yl-10,12-dihydro-10-azaindeno[2,1-b]fluorene 13 g (22 mmol) of 7-bromo-12,12-dimethyl-10-triphenylen-2-yl-10,12-dihydro-10-azaindeno[2,1-b]fluorene, 6.2 g (24 mmol) of bis(pinacolato)-diborane and 6.3 g (64 mmol) of potassium acetate are suspended in 75 ml of dioxane. 0.53 g (0.66 mmol) of 1,1-bis(diphenylphosphino)-ferrocenepalladium(II) dichloride complex with DCM are added to this suspension. The reaction mixture is heated under reflux for 16 h. After cooling, the organic phase is separated off, washed three times with 50 ml of water and subsequently evaporated to dryness. The residue is recrystallised from toluene (10.6 g, 17 mmol, 76%).

B24: 7-(4,6-Diphenyl-1,3,5-triazin-2-yl)-12,12-dimethyl-10-triphenylen-2-yl-10,12-dihydro-10-azaindeno[2,1-b]fluorene 8.5 g (13.4 mmol) of 12,12-dimethyl-7-(4,4,5,5-tetramethyl-1,3,2-dioxaborolan-2-yl)-10-triphenylen-2-yl-10,12-dihydro-10-azaindeno[2,1-b]fluorene, 3.6 g (13.4 mmol) of 2-chloro-4,6-diphenyl-1,3,5-triazine and 2.2 g of sodium carbonate are suspended in 150 ml of dioxane, 150 ml of toluene and 75 ml of water. 0.76 g (0.66 mmol) of Pd(PPh$_3$)$_4$ are added to this suspension. The reaction mixture is heated under reflux for 5 h. After cooling, the precipitated solid is filtered off with suction, washed with water and ethanol and dried. The residue is extracted with hot toluene and recrystallised from toluene/heptane. Sublimation gives 9.9 g (11 mmol, 82%) of the product having an HPLC purity>99.9%.

The following compounds are prepared analogously:
| Ex. | Starting material | Product | Yield |
|---|---|---|---|
| B25 | 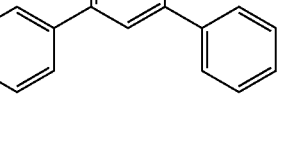 | 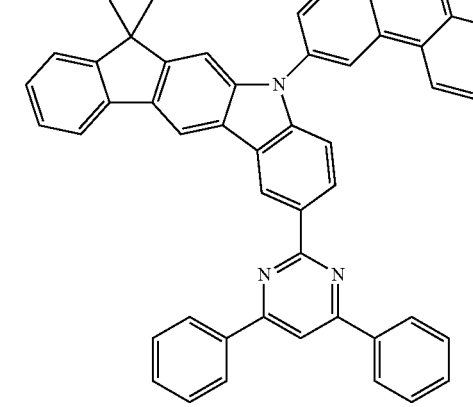 | 86% |
| B26 | 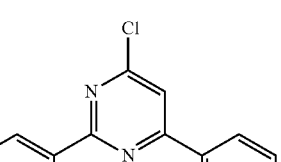 | 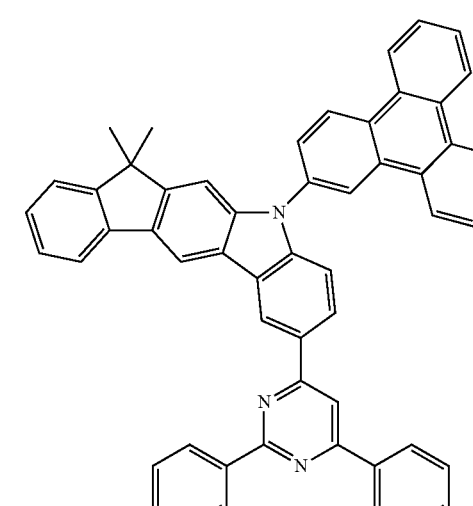 | 90% |
| B27 | 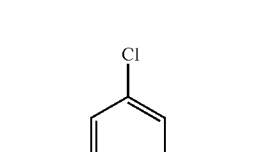 | 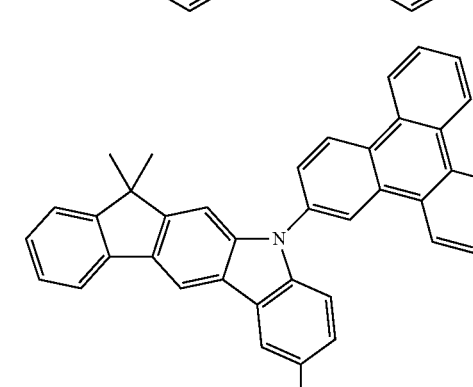 | 78% |

| Ex. | Starting material | Product | Yield |
|---|---|---|---|
| B28 | 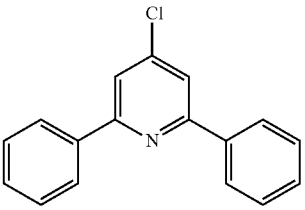 [SMILES: Clc1cc(-c2ccccc2)nc(-c2ccccc2)c1] | 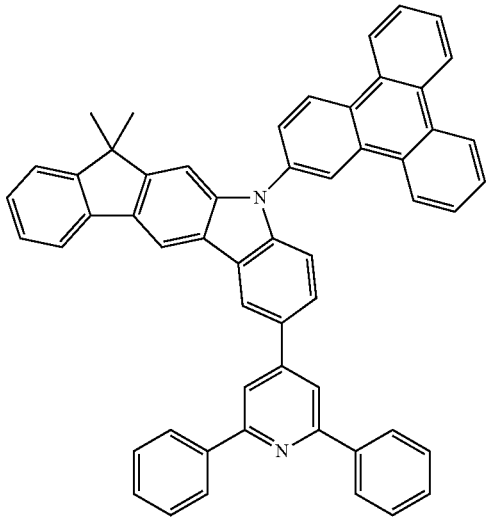 [SMILES: CC1(C)c2ccccc2-c2cc3c4cc(-c5cc(-c6ccccc6)nc(-c6ccccc6)c5)ccc4n(-c4ccc5c6ccccc6c6ccccc6c5c4)c3cc21] | 87% |

Synthesis of B29

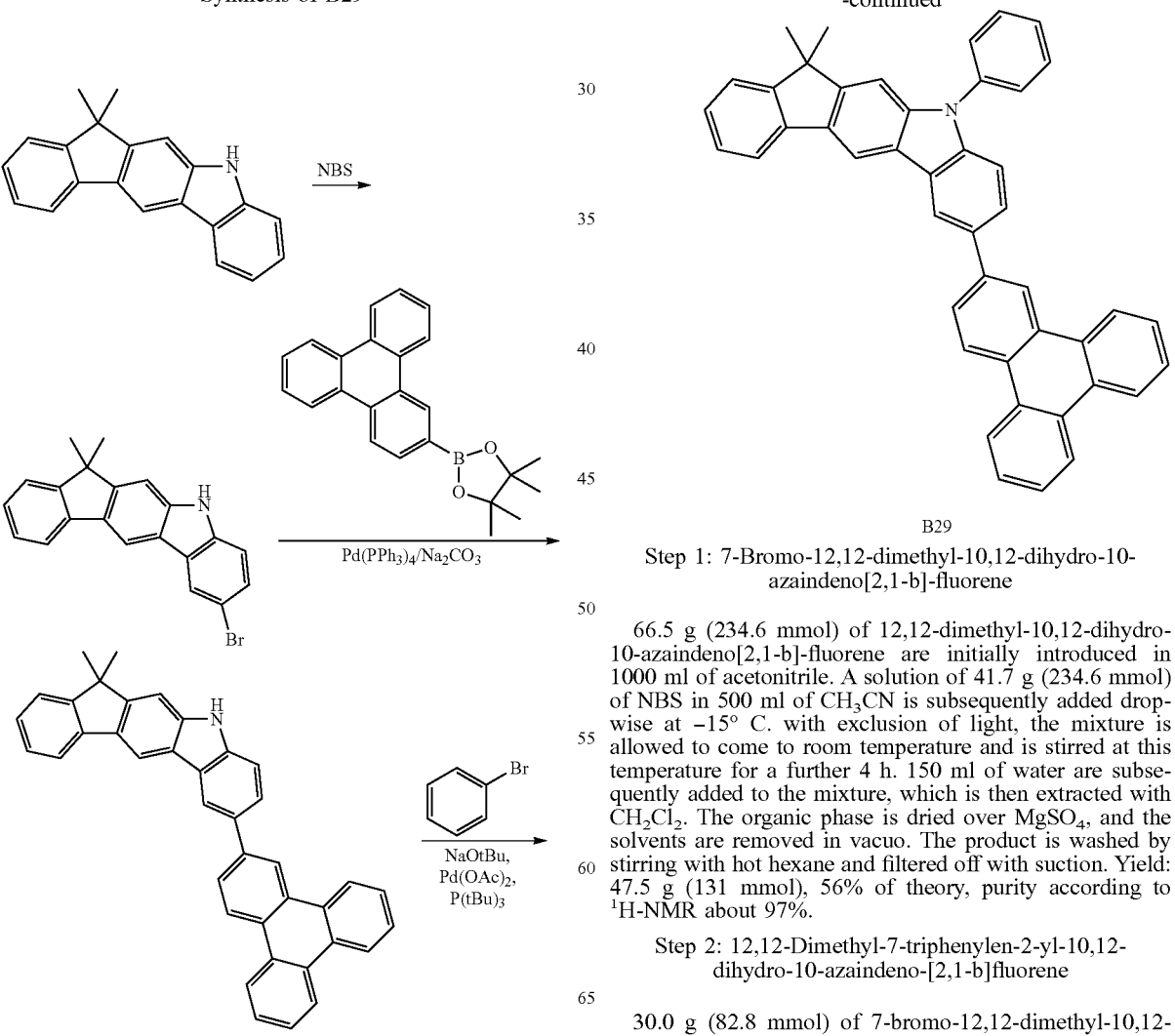

B29

Step 1: 7-Bromo-12,12-dimethyl-10,12-dihydro-10-azaindeno[2,1-b]-fluorene 66.5 g (234.6 mmol) of 12,12-dimethyl-10,12-dihydro-10-azaindeno[2,1-b]-fluorene are initially introduced in 1000 ml of acetonitrile. A solution of 41.7 g (234.6 mmol) of NBS in 500 ml of $CH_3CN$ is subsequently added dropwise at −15° C. with exclusion of light, the mixture is allowed to come to room temperature and is stirred at this temperature for a further 4 h. 150 ml of water are subsequently added to the mixture, which is then extracted with $CH_2Cl_2$. The organic phase is dried over $MgSO_4$, and the solvents are removed in vacuo. The product is washed by stirring with hot hexane and filtered off with suction. Yield: 47.5 g (131 mmol), 56% of theory, purity according to $^1$H-NMR about 97%.

Step 2: 12,12-Dimethyl-7-triphenylen-2-yl-10,12-dihydro-10-azaindeno-[2,1-b]fluorene 30.0 g (82.8 mmol) of 7-bromo-12,12-dimethyl-10,12-dihydro-10-azaindeno[2,1-b]fluorene, 29.3 g (82.8 mmol) of 4,4,5,5-tetramethyl-2-triphenylen-2-yl-1,3,2-dioxaborolane and 13.6 g of sodium carbonate are suspended in 500 ml of dioxane, 500 ml of toluene and 250 ml of water. 4.7 g (4.1 mmol) of Pd(PPh$_3$)$_4$ are added to this suspension. The reaction mixture is heated under reflux for 13 h. After cooling, the precipitated solid is filtered off with suction, washed with water and ethanol and dried. The residue is extracted with hot toluene and recrystallised from toluene/heptane. Yield: 37.6 g (11 mmol, 89%).

Step 3: Synthesis of 12,12-dimethyl-10-phenyl-7-triphenylen-2-yl-10,12-dihydro-10-azaindeno[2,1-b]fluorene (B29)

10.0 g (19.6 mmol) of 12,12-dimethyl-7-triphenylen-2-yl-10,12-dihydro-10-azaindeno[2,1-b]fluorene and 4.6 g (29 mmol) of bromobenzene are initially introduced in 250 ml of xylene and degassed. After addition of 57.6 g (600 mmol) of sodium tert-butoxide, the mixture is stirred for 15 minutes, and 12 ml (12 mmol) of tri-tert-butylphosphine and 1.7 g (7.7 mmol) of palladium acetate are subsequently added. The batch is heated under reflux for 28 h. When the reaction is complete, the reaction mixture is washed with water, the aqueous phase is extracted with toluene, and the combined organic phases are dried over sodium sulfate. The solvent is removed in a rotary evaporator, and the residue is extracted with hot toluene, giving 10.7 g (18.3 mmol, 93%) of the product having an HPLC purity>99.9%.

The following compounds are prepared analogously:

| Ex. | Starting material | Product | Yield |
|---|---|---|---|
| B30 | (2-chloro-4,6-diphenyl-1,3,5-triazine) | (structure shown) | 84% |
| B31 | (2-bromotriphenylene) | (structure shown) | 88% |

-continued
| Ex. | Starting material | Product | Yield |
|---|---|---|---|
| B32 | 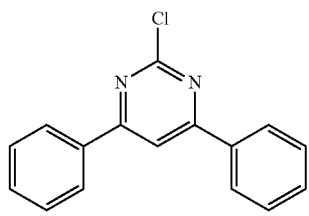 [SMILES: Clc1nc(-c2ccccc2)cc(-c2ccccc2)n1] | 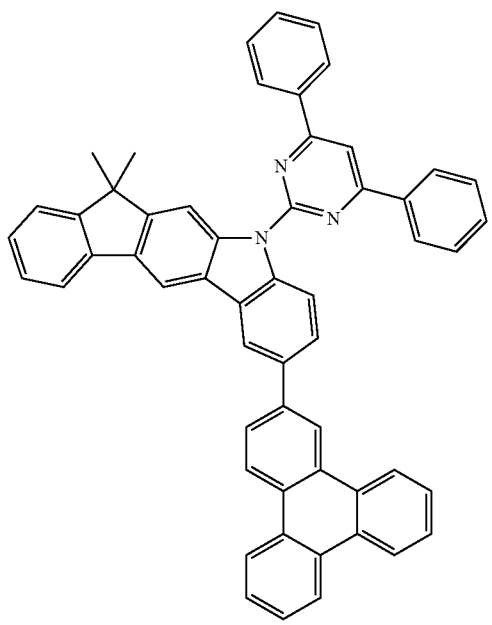 [SMILES: CC1(C)c2ccccc2-c2cc3c4cc(-c5ccc6c7ccccc7c7ccccc7c6c5)ccc4n(-c4nc(-c5ccccc5)cc(-c5ccccc5)n4)c3cc21] | 71% |
| B33 | 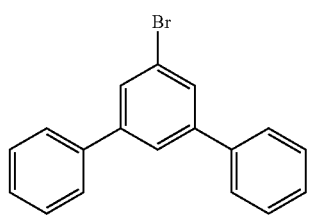 [SMILES: Brc1cc(-c2ccccc2)cc(-c2ccccc2)c1] | 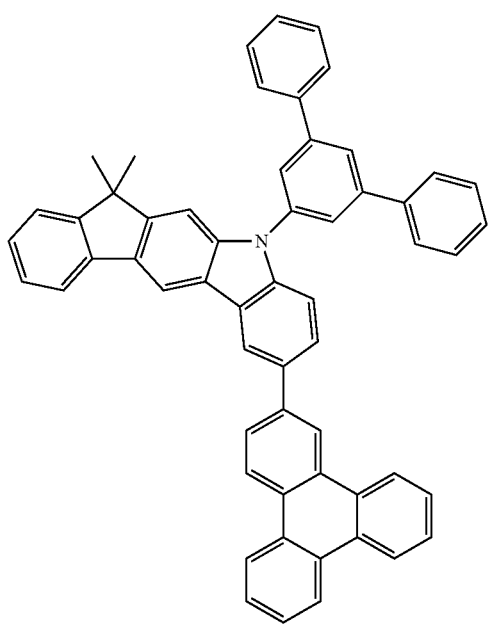 [SMILES: CC1(C)c2ccccc2-c2cc3c4cc(-c5ccc6c7ccccc7c7ccccc7c6c5)ccc4n(-c4cc(-c5ccccc5)cc(-c5ccccc5)c4)c3cc21] | 92% |

| Ex. | Starting material | Product | Yield |
|---|---|---|---|
| B34 | | | 92% |

Example

Production of OLEDs

OLEDs according to the invention and OLEDs in accordance with the prior art are produced by a general process in accordance with WO 2004/058911, which is adapted to the circumstances described here (layer-thickness variation, materials).

The data for various OLEDs are presented in Examples V1 to E24 below (see Tables 1 and 2). Glass plates coated with structured ITO (indium tin oxide) in a thickness of 50 nm are coated with 20 nm of PEDOT:PSS (poly(3,4-ethylenedioxythiophene)poly(styrenesulfonate), purchased as CLEVIOS™ P VP AI 4083 from Heraeus Precious Metals GmbH, Germany, applied by spin coating from aqueous solution) for improved processing. These coated glass plates form the substrates to which the OLEDs are applied. The OLEDs have in principle the following layer structure: substrate/hole-transport layer (HTL)/interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials required for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as IC1:IC3: TEG1 (70%:20%:10%) here means that material IC1 is present in the layer in a proportion by volume of 70%, IC3 is present in the layer in a proportion of 20% and TEG1 is present in the layer in a proportion of 10%.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931x and y colour coordinates are calculated therefrom. The term U1000 in Table 2 denotes the voltage required for a luminous density of 1000 cd/m$^2$. CE1000 and PE1000 denote the current efficiency and power efficiency achieved at 1000 cd/m$^2$. Finally, EQE1000 denotes the external quantum efficiency at an operating luminous density of 1000 cd/m$^2$. The lifetime LT is defined as the time after which the luminous density drops from the initial luminous density L0 to a certain proportion L1 on operation at constant current. An expression of L0=4000 cd/m$^2$ and L0=80% in Table X2 means that the lifetime indicated in column LT corresponds to the time after which the initial luminous density drops from 4000 cd/m$^2$ to 3200 cd/m$^2$.

The data for the various OLEDs are summarized in Table 2. Examples V1-V10 are comparative examples in accordance with the prior art, Examples E1-E24 show data of OLEDs comprising materials according to the invention.

Some of the examples are explained in greater detail below in order to illustrate the advantages of the compounds according to the invention. However, it should be pointed out that this only represents a selection of the data shown in Table 2. As can be seen in the table, significant improvements compared with the prior art are also achieved on use of the compounds according to the invention which are not described in greater detail, in some cases in all parameters, but in some cases only an improvement in efficiency or voltage or lifetime can be observed. However, even the improvement in one of the said parameters represents a significant advance, since different applications require optimisation with respect to different parameters.

Use of Compounds According to the Invention as Matrix Materials in Phosphorescent OLEDs If material TPCbz1 is compared with material B3 according to the invention on use as second matrix component in combination with ST1, it is apparent that replacement of carbazole by indenocarbazole causes a slight improvement in the power efficiency, but in particular a significant improvement in the lifetime by about 70% (Examples V7 and E6). On replacement of a biphenyl (material BIC2) by triphenylene (material B3) as connecting group between two indenocarbazoles, an improvement in the lifetime by about 50% arises (Examples V2 and E6).

Substitution by a triphenylene also has a positive influence on the lifetime on use of only one matrix material in phosphorescent OLEDs. Thus, for example, an increase by almost 25% is achieved with compound B34 (Examples V4 and E20).

TABLE 1

Structure of the OLEDs

| Ex. | HTL Thickness | IL Thickness | EBL Thickness | EML Thickness | HBL Thickness | ETL Thickness | EIL |
|---|---|---|---|---|---|---|---|
| V1 | SpA1 70 nm | HATCN 5 nm | SpMA1 90 nm | IC1:BIC1:TEG1 (60%:30%:10%) 30 nm | IC1 10 nm | ST1:LiQ (50%:50%) 30 nm | — |
| V2 | SpA1 70 nm | HATCN 5 nm | BPA1 90 nm | ST1:BIC2:TEG1 (30%:60%:10%) 30 nm | ST1 10 nm | ST1:LiQ (50%:50%) 30 nm | — |
| V3 | SpA1 70 nm | HATCN 5 nm | SpMA1 90 nm | IC1:IC3:TEG1 (70%:20%:10%) 30 nm | IC1 10 nm | ST1:LiQ (50%:50%) 30 nm | — |
| V4 | SpA1 90 nm | HATCN 5 nm | SpMA1 130 nm | IC5:TER1 (92%:8%) 40 nm | — | ST2:LiQ (50%:50%) 40 nm | — |
| V5 | SpA1 70 nm | HATCN 5 nm | SpMA1 90 nm | IC1:TEG1 (90%:10%) 30 nm | — | ST1:LiQ (50%:50%) 40 nm | — |
| V6 | SpA1 70 nm | HATCN 5 nm | SpMA1 90 nm | ST1:IC4:TEG1 (25%:60%:15%) 30 nm | IC1 10 nm | ST1:LiQ (50%:50%) 30 nm | — |
| V7 | SpA1 70 nm | HATCN 5 nm | SpMA1 90 nm | ST1:TPCbz1:TEG1 (25%:60%:15%) 30 nm | IC1 10 nm | ST1:LiQ (50%:50%) 30 nm | — |
| V8 | SpA1 70 nm | HATCN 5 nm | SpMA1 90 nm | IC2:TEG1 (90%:10%) 30 nm | — | ST1:LiQ (50%:50%) 40 nm | — |
| V9 | SpA1 70 nm | HATCN 5 nm | SpMA1 90 nm | IC5:TEG1 (90%:10%) 30 nm | — | ST1:LiQ (50%:50%) 40 nm | — |
| V10 | SpA1 70 nm | HATCN 5 nm | SpMA1 90 nm | IC6:TEG1 (90%:10%) 30 nm | — | ST1:LiQ (50%:50%) 40 nm | — |
| E1 | SpA1 70 nm | HATCN 5 nm | SpMA1 90 nm | ST1:B1:TEG1 (25%:60%:15%) 30 nm | IC1 10 nm | ST1:LiQ (50%:50%) 30 nm | — |
| E2 | SpA1 70 nm | HATCN 5 nm | SpMA1 90 nm | ST1:B2:TEG1 (25%:60%:15%) 30 nm | IC1 10 nm | ST1:LiQ (50%:50%) 30 nm | — |
| E3 | SpA1 70 nm | HATCN 5 nm | SpMA1 90 nm | ST1:B4:TEG1 (25%:60%:15%) 30 nm | IC1 10 nm | ST1:LiQ (50%:50%) 30 nm | — |
| E4 | SpA1 70 nm | HATCN 5 nm | SpMA1 90 nm | IC1:B17:TEG1 (60%:35%:5%) 30 nm | IC1 10 nm | ST1:LiQ (50%:50%) 30 nm | — |
| E5 | SpA1 70 nm | HATCN 5 nm | SpMA1 90 nm | IC1:B18:TEG1 (60%:35%:5%) 30 nm | IC1 10 nm | ST1:LiQ (50%:50%) 30 nm | — |
| E6 | SpA1 70 nm | HATCN 5 nm | BPA1 90 nm | ST1:B3:TEG1 (30%:60%:10%) 30 nm | ST1 10 nm | ST1:LiQ (50%:50%) 30 nm | — |
| E7 | SpA1 70 nm | HATCN 5 nm | SpMA1 90 nm | ST1:B29:TEG1 (25%:60%:15%) 30 nm | IC1 10 nm | ST1:LiQ (50%:50%) 30 nm | — |
| E8 | SpA1 70 nm | HATCN 5 nm | SpMA1 90 nm | IC1:B12:TEG1 (70%:20%:10%) 30 nm | IC1 10 nm | ST1:LiQ (50%:50%) 30 nm | — |
| E9 | SpA1 70 nm | HATCN 5 nm | SpMA1 90 nm | ST1:B10:TEG1 (25%:60%:15%) 30 nm | IC1 10 nm | ST1:LiQ (50%:50%) 30 nm | — |
| E10 | SpA1 70 nm | HATCN 5 nm | SpMA1 90 nm | ST1:B7:TEG1 (25%:60%:15%) 30 nm | IC1 10 nm | ST1:LiQ (50%:50%) 30 nm | — |
| E11 | SpA1 70 nm | HATCN 5 nm | SpMA1 90 nm | ST1:B8:TEG1 (25%:60%:15%) 30 nm | IC1 10 nm | ST1:LiQ (50%:50%) 30 nm | — |
| E12 | SpA1 70 nm | HATCN 5 nm | SpMA1 90 nm | IC1:B21:TEG1 (30%:60%:10%) 30 nm | IC1 10 nm | ST1:LiQ (50%:50%) 30 nm | — |
| E13 | SpA1 70 nm | HATCN 5 nm | SpMA1 90 nm | IC1:B20:TEG1 (30%:60%:10%) 30 nm | IC1 10 nm | ST1:LiQ (50%:50%) 30 nm | — |
| E14 | SpA1 70 nm | HATCN 5 nm | SpMA1 90 nm | IC1:B19:TEG1 (30%:60%:10%) 30 nm | IC1 10 nm | ST1:LiQ (50%:50%) 30 nm | — |
| E15 | SpA1 70 nm | HATCN 5 nm | SpMA1 90 nm | B24:TEG1 (90%:10%) 30 nm | — | ST1:LiQ (50%:50%) 40 nm | — |
| E16 | SpA1 70 nm | HATCN 5 nm | SpMA1 90 nm | B25:TEG1 (90%:10%) 30 nm | — | ST1:LiQ (50%:50%) 40 nm | — |
| E17 | SpA1 70 nm | HATCN 5 nm | SpMA1 90 nm | B30:TEG1 (90%:10%) 30 nm | — | ST1:LiQ (50%:50%) 40 nm | — |
| E18 | SpA1 70 nm | HATCN 5 nm | SpMA1 90 nm | B32:TEG1 (90%:10%) 30 nm | — | ST1:LiQ (50%:50%) 40 nm | — |
| E19 | SpA1 70 nm | HATCN 5 nm | SpMA1 90 nm | B34:TEG1 (90%:10%) 30 nm | — | ST1:LiQ (50%:50%) 40 nm | — |
| E20 | SpA1 90 nm | HATCN 5 nm | SpMA1 130 nm | B34:TER1 (92%:8%) 40 nm | — | ST2:LiQ (50%:50%) 40 nm | — |
| E21 | SpA1 90 nm | HATCN 5 nm | SpMA1 130 nm | B13:TER1 (92%:8%) 40 nm | — | ST2:LiQ (50%:50%) 40 nm | — |
| E22 | SpA1 70 nm | HATCN 5 nm | SpMA1 90 nm | IC1:B11:TEG1 (30%:60%:10%) 30 nm | IC1 10 nm | ST1:LiQ (50%:50%) 30 nm | — |

TABLE 1-continued

Structure of the OLEDs

| Ex. | HTL Thickness | IL Thickness | EBL Thickness | EML Thickness | HBL Thickness | ETL Thickness | EIL |
|---|---|---|---|---|---|---|---|
| E23 | SpA1 70 nm | HATCN 5 nm | SpMA1 90 nm | ST1:IC4:TEG1 (25%:60%:15%) 30 nm | B30 10 nm | ST1:LiQ (50%:50%) 30 nm | — |
| E24 | SpA1 70 nm | HATCN 5 nm | SpMA1 90 nm | IC1:TEG1 (90%:10%) 30 nm | — | B13 40 nm | LiQ 3 nm |

TABLE 2

Data for the OLEDs

| Ex. | U1000 (V) | CE1000 (cd/A) | PE1000 (lm/W) | EQE 1000 | CIE x/y at 1000 cd/m$^2$ | L0 | L1 % | LT (h) |
|---|---|---|---|---|---|---|---|---|
| V1 | 3.6 | 51 | 44 | 14.1% | 0.34/0.62 | 10000 cd/m$^2$ | 70 | 240 |
| V2 | 3.8 | 51 | 43 | 14.3% | 0.33/0.63 | 10000 cd/m$^2$ | 70 | 210 |
| V3 | 3.2 | 54 | 54 | 15.1% | 0.33/0.63 | 10000 cd/m$^2$ | 80 | 190 |
| V4 | 4.5 | 11.2 | 7.8 | 12.1% | 0.67/0.33 | 4000 cd/m$^2$ | 80 | 410 |
| V5 | 3.5 | 57 | 52 | 16.2% | 0.34/0.62 | 10000 cd/m$^2$ | 70 | 160 |
| V6 | 3.5 | 56 | 50 | 15.7% | 0.34/0.62 | 10000 cd/m$^2$ | 70 | 350 |
| V7 | 3.8 | 50 | 42 | 13.9% | 0.33/0.63 | 10000 cd/m$^2$ | 70 | 190 |
| V8 | 3.5 | 59 | 52 | 16.4% | 0.33/0.62 | 10000 cd/m$^2$ | 70 | 160 |
| V9 | 3.3 | 53 | 51 | 14.8% | 0.33/0.61 | 10000 cd/m$^2$ | 70 | 150 |
| V10 | 3.6 | 57 | 49 | 15.8% | 0.33/0.62 | 10000 cd/m$^2$ | 70 | 150 |
| E1 | 3.5 | 60 | 54 | 16.7% | 0.34/0.62 | 10000 cd/m$^2$ | 70 | 420 |
| E2 | 3.5 | 57 | 52 | 16.1% | 0.35/0.62 | 10000 cd/m$^2$ | 70 | 410 |
| E3 | 3.6 | 56 | 50 | 15.8% | 0.34/0.62 | 10000 cd/m$^2$ | 70 | 430 |
| E4 | 3.4 | 60 | 55 | 16.7% | 0.33/0.63 | 10000 cd/m$^2$ | 70 | 450 |
| E5 | 3.6 | 56 | 48 | 15.5% | 0.33/0.62 | 10000 cd/m$^2$ | 70 | 330 |
| E6 | 3.7 | 53 | 45 | 14.7% | 0.33/0.62 | 10000 cd/m$^2$ | 70 | 320 |
| E7 | 3.6 | 57 | 51 | 16.0% | 0.34/0.63 | 10000 cd/m$^2$ | 70 | 370 |
| E8 | 3.3 | 61 | 57 | 16.9% | 0.33/0.62 | 10000 cd/m$^2$ | 80 | 230 |
| E9 | 3.5 | 51 | 49 | 14.3% | 0.33/0.63 | 10000 cd/m$^2$ | 70 | 370 |
| E10 | 3.6 | 57 | 50 | 15.8% | 0.32/0.62 | 10000 cd/m$^2$ | 70 | 370 |
| E11 | 3.6 | 55 | 48 | 15.2% | 0.34/0.62 | 10000 cd/m$^2$ | 70 | 400 |
| E12 | 3.5 | 50 | 44 | 13.9% | 0.33/0.62 | 10000 cd/m$^2$ | 70 | 380 |
| E13 | 3.5 | 55 | 50 | 15.3% | 0.33/0.62 | 10000 cd/m$^2$ | 70 | 390 |
| E14 | 3.4 | 60 | 55 | 16.7% | 0.33/0.63 | 10000 cd/m$^2$ | 70 | 360 |
| E15 | 3.5 | 60 | 54 | 16.5% | 0.33/0.63 | 10000 cd/m$^2$ | 70 | 130 |
| E16 | 3.5 | 59 | 52 | 16.3% | 0.33/0.62 | 10000 cd/m$^2$ | 70 | 140 |
| E17 | 3.6 | 56 | 49 | 15.5% | 0.32/0.62 | 10000 cd/m$^2$ | 70 | 190 |
| E18 | 3.5 | 61 | 55 | 17.0% | 0.33/0.63 | 10000 cd/m$^2$ | 70 | 140 |
| E19 | 3.4 | 54 | 50 | 15.2% | 0.33/0.62 | 10000 cd/m$^2$ | 70 | 200 |
| E20 | 4.6 | 10.7 | 7.3 | 11.6% | 0.67/0.33 | 4000 cd/m$^2$ | 80 | 510 |
| E21 | 4.2 | 11.8 | 8.7 | 12.8% | 0.67/0.33 | 4000 cd/m$^2$ | 80 | 380 |
| E22 | 3.6 | 59 | 51 | 16.4% | 0.34/0.62 | 10000 cd/m$^2$ | 70 | 350 |
| E23 | 3.5 | 55 | 49 | 15.4% | 0.34/0.62 | 10000 cd/m$^2$ | 70 | 380 |
| E24 | 3.7 | 56 | 49 | 15.7% | 0.33/0.63 | 10000 cd/m$^2$ | 70 | 190 |

TABLE 3

Structural formulae of the materials for the OLEDs

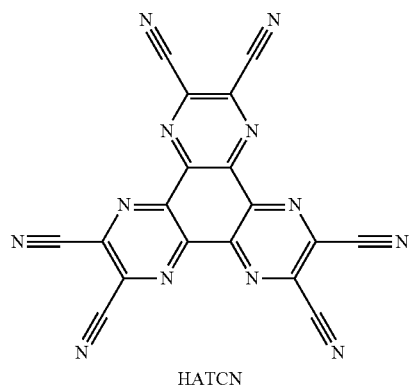

HATCN

TABLE 3-continued

Structural formulae of the materials for the OLEDs

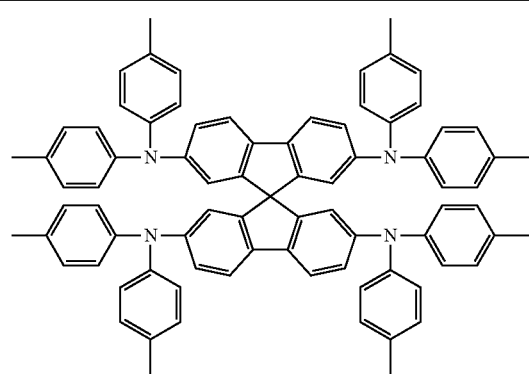

SpA1

TABLE 3-continued
Structural formulae of the materials for the OLEDs
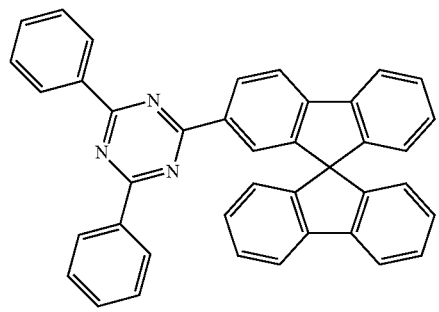
ST1
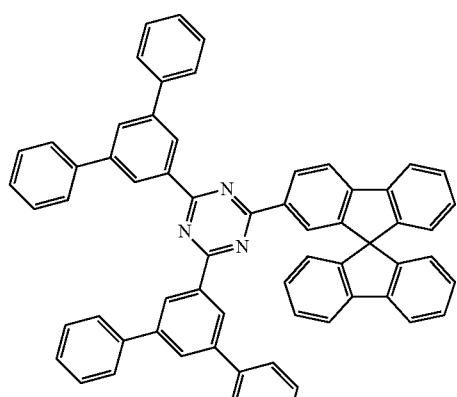
ST2
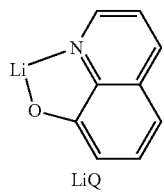
LiQ
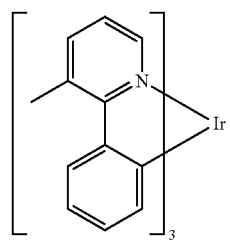
TEG1
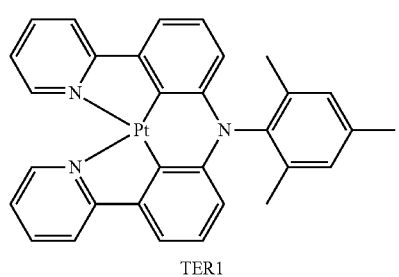
TER1
TABLE 3-continued
Structural formulae of the materials for the OLEDs
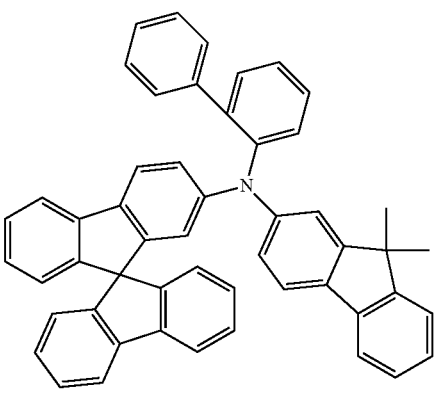
SpMA1
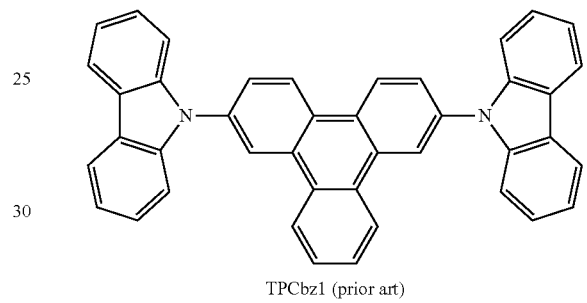
TPCbz1 (prior art)
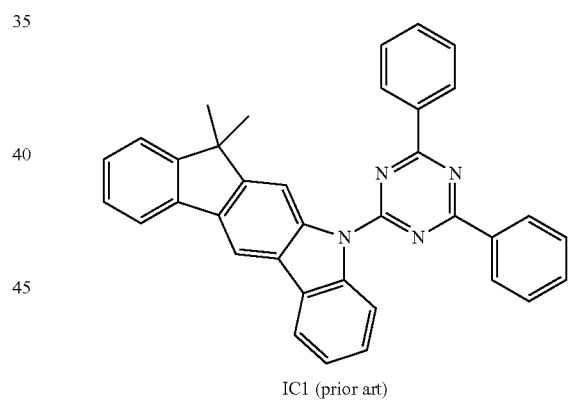
IC1 (prior art)
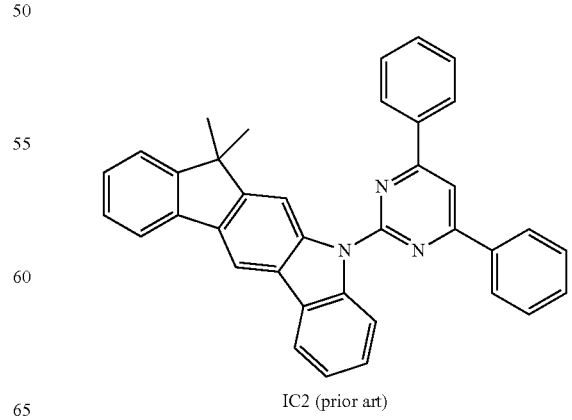
IC2 (prior art)

TABLE 3-continued
Structural formulae of the materials for the OLEDs
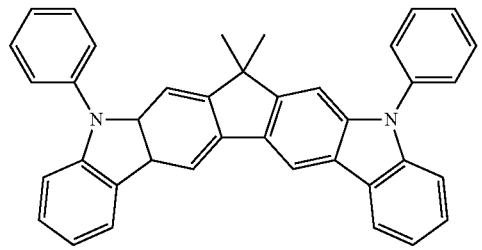
IC3 (prior art)
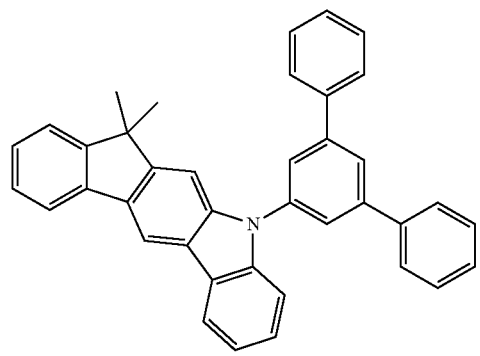
IC4 (prior art)
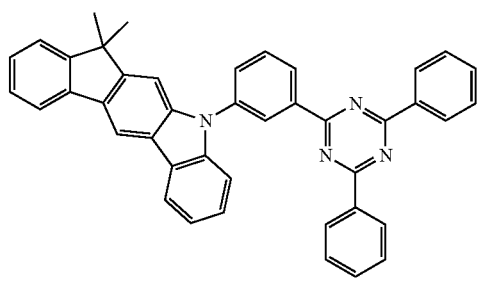
IC5 (prior art)
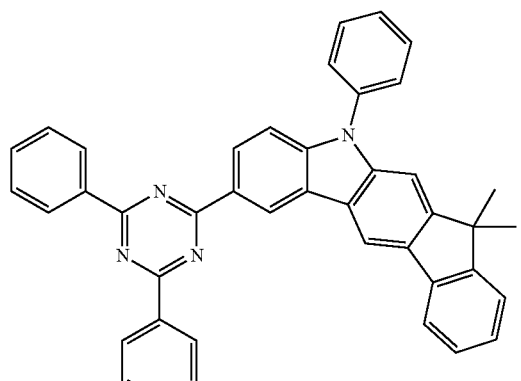
IC6 (prior art)
TABLE 3-continued
Structural formulae of the materials for the OLEDs
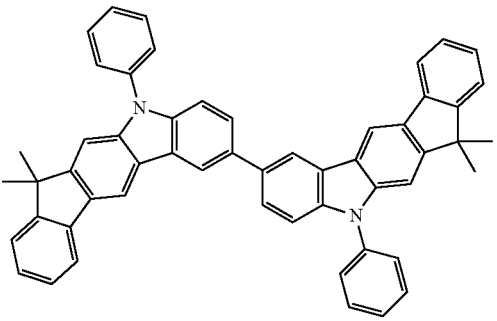
BIC1 (prior art)
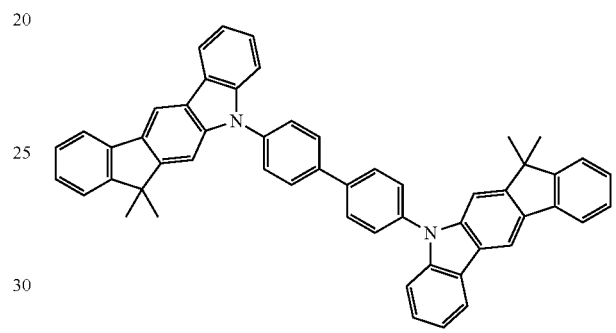
BIC2 (prior art)
The invention claimed is:
1. A compound of the formula (1), formula (2), formula (3), or formula (4),
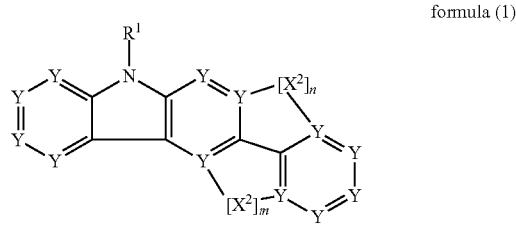
formula (1)
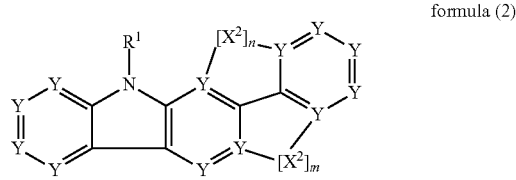
formula (2)
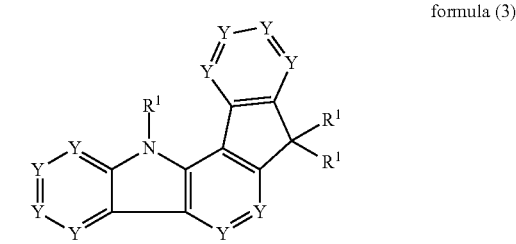
formula (3)

formula (4)

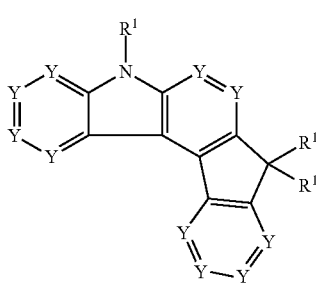

wherein

Y is C if a group $X^2$ is bonded to this group Y, or is identically on each occurrence CR if no group $X^2$ is bonded to this group Y;

$X^2$ is $C(R^1)_2$;

R, $R^1$ are identically or differently on each occurrence H, D, F, Cl, Br, I, $N(R^2)_2$, $N(Ar)_2$, C(=O)Ar, P(=O)$Ar_2$, S(=O)Ar, S(=O)$_2$Ar, $CR^2$=$CR^2$Ar, CN, $NO_2$, $Si(R^2)_3$, $B(OR^2)_2$, $OSO_2R^2$, a straight-chain alkyl, alkoxy, or thioalkoxy group having 1 to 40 C atoms or a branched or cyclic alkyl, alkoxy or thioalkoxy group having 3 to 40 C atoms, each of which is optionally substituted by one or more radicals $R^2$, where one or more non-adjacent $CH_2$ groups are optionally replaced by $R^2C$=$CR^2$, C≡C, $Si(R^2)_2$, C=O, C=$NR^2$, P(=O)($R^2$), SO, $SO_2$, $NR^2$, O, S, or $CONR^2$, and where one or more H atoms are optionally replaced by D, F, Cl, Br, I, CN, or $NO_2$, or an aromatic or heteroaromatic ring system having 5 to 60 aromatic ring atoms, optionally substituted by one or more radicals $R^2$, or an aryloxy or heteroaryloxy group having 5 to 40 aromatic ring atoms, optionally substituted by one or more radicals $R^2$, or an aralkyl or heteroaralkyl group having 5 to 40 aromatic ring atoms, optionally substituted by one or more radicals $R^2$, or a combination of these systems;

Ar is identically or differently on each occurrence an aromatic or heteroaromatic ring system, optionally substituted by one or more radicals $R^3$;

$R^2$ is identically or differently on each occurrence H, D, F, Cl, Br, I, $N(R^3)_2$, $N(Ar)_2$, C(=O)Ar, P(=O)$Ar_2$, S(=O)Ar, S(=O)$_2$Ar, $CR^3$=$CR^3$Ar, CN, $NO_2$, $Si(R^3)_3$, $B(OR^3)_2$, $OSO_2R^3$, a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals $R^3$, where one or more nonadjacent $CH_2$ groups are optionally replaced by $R^3C$=$CR^3$, C≡C, $Si(R^3)_2$, C=O, C=$NR^3$, P(=O)($R^3$), SO, $SO_2$, $NR^3$, O, S or $CONR^3$, and where one or more H atoms are optionally replaced by D, F, Cl, Br, I, CN or $NO_2$, or an aromatic or heteroaromatic ring system having 5 to 60 aromatic ring atoms, optionally substituted by one or more radicals $R^3$, or an aryloxy or heteroaryloxy group having 5 to 40 aromatic ring atoms, optionally substituted by one or more radicals $R^3$, or an aralkyl or heteroaralkyl group having 5 to 40 aromatic ring atoms, optionally substituted by one or more radicals $R^3$, or a combination of these systems;

$R^3$ is identically or differently on each occurrence H, D, an aliphatic hydrocarbon radical having 1 to 20 C atoms, an aryl or heteroaryl group having 5 to 40 ring atoms, or a combination of these groups;

n, m are identically or differently on each occurrence 0 or 1, with the proviso that n+m=1;

wherein at least one group R and/or $R^1$ is present and is a group of formula (5),

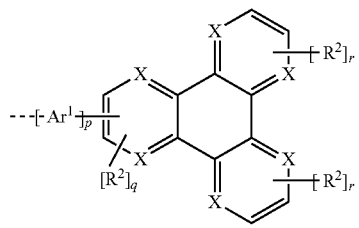

formula (5)

where the dashed bond indicates the linking of the group of the formula (5), $R^2$ has the meanings given above and furthermore:

X is C if the group $Ar^1$ or the remainder of the molecule is bonded to this X, and is otherwise identically or differently on each occurrence $CR^2$ or N;

$Ar^1$ is a divalent aromatic or heteroaromatic ring system having 5 to 40 aromatic ring atoms, optionally substituted by one or more radicals $R^2$;

p is identically or differently on each occurrence 0 or 1;

q, r is identically or differently on each occurrence 0, 1, or 2.

2. The compound of claim 1, wherein the compound is selected from compounds of the formula (1a), (2a), (3a), or (4a),

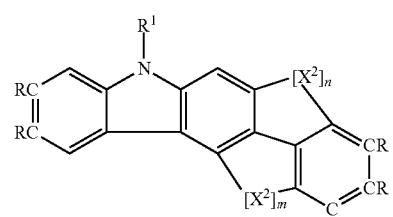

formula (1a)

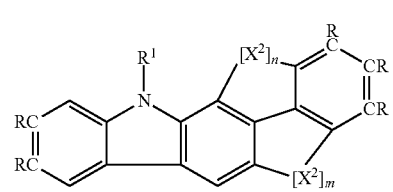

formula (2a)

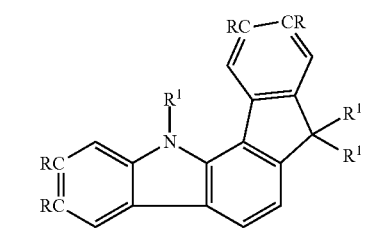

formula (3a)

formula (4a)

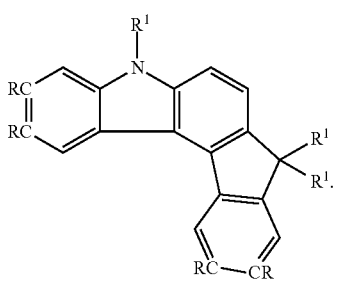

3. The compound of claim 1, wherein the group of the formula (5) is a group of formula (5a), formula (5a)

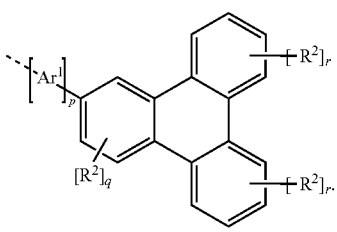

4. The compound of claim 1, wherein the group of the formula (5) represents a group of formula (5b) or (5c).

formula (5b)

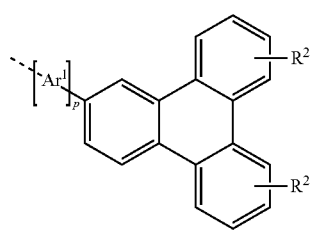

formula (5c)

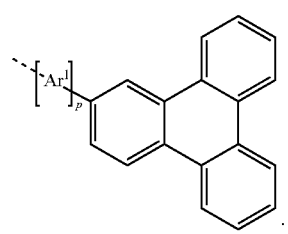

5. A mixture comprising at least one compound of claim 1 and at least one further compound.

6. A formulation comprising at least one compound of claim 1 and one or more solvents.

7. An electronic device comprising the compound of claim 1.

8. The electronic device of claim 7, wherein said electronic device is selected from the group consisting of organic electroluminescent devices, organic integrated circuits, organic field-effect transistors, organic thin-film transistors, organic light-emitting transistors, organic solar cells, organic dye-sensitised solar cells, organic optical detectors, organic photoreceptors, organic field-quench devices, light-emitting electrochemical cells, organic laser diodes, and organic plasmon emitting devices.

9. The electronic device according to claim 8, wherein said electronic device is an organic electroluminescent device and the compound is employed as matrix material for fluorescent or phosphorescent emitters and/or in a hole-blocking layer and/or in an electron-transport layer and/or in an electron-blocking or exciton-blocking layer and/or in a hole-transport layer.

10. The mixture of claim 5, wherein the at least one further compound is a phosphorescent dopant.

11. A formulation comprising the mixture of claim 5 and one or more solvents.

12. An electronic device comprising the mixture of claim 5.

13. The electronic device of claim 12, wherein said electronic device is selected from the group consisting of organic electroluminescent devices, organic integrated circuits, organic field-effect transistors, organic thin-film transistors, organic light-emitting transistors, organic solar cells, organic dye-sensitised solar cells, organic optical detectors, organic photoreceptors, organic field-quench devices, light-emitting electrochemical cells, organic laser diodes, and organic plasmon emitting devices.

14. The electronic device according to claim 13, wherein said electronic device is an organic electroluminescent device and the mixture is employed as matrix material for fluorescent or phosphorescent emitters and/or in a hole-blocking layer and/or in an electron-transport layer and/or in an electron-blocking or exciton-blocking layer and/or in a hole-transport layer.

15. The compound of claim 1, wherein the compound is selected from formula (1e) or formula (1i)

formula (1e)

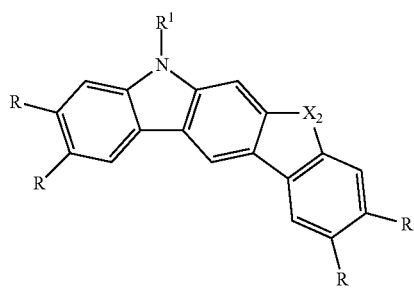

formula (1i)

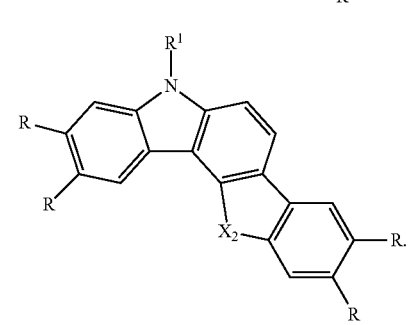

16. The compound of claim 1, wherein the compounds of formula (1), m=0 is represented by formula (1N), or n=0, is represented by formula (1M)

formula (1N)

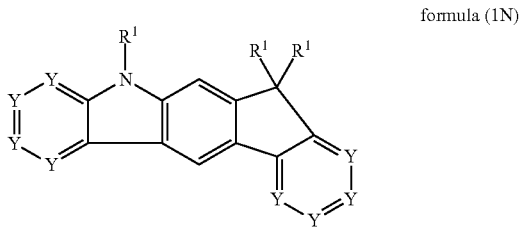

-continued formula (1M)

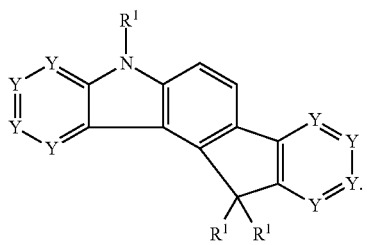

formula (2M)

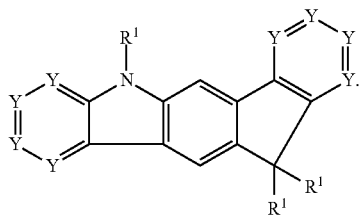

17. The compound of claim 1, wherein the compounds of formula (2), m=0 is represented by formula (2N), or n=0, is represented by formula (2M)

formula (2N)

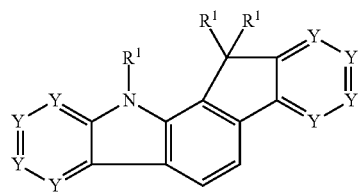

18. The compound of claim 1, wherein the group $R^1$ in the bridge $NR^1$ is an aromatic or heteroaromatic ring system with 6 to 24 aromatic ring atoms, optionally substituted with one or more radicals $R^2$.

19. The compound of claim 18, Wherein the group $R^1$ in the bridge $C(R^1)_2$ is a straight-chain alkyl group having 1 to 20 C atoms or a branched or cyclic alkyl group having 3 to 20 C atoms, optionally substituted with one or more radicals $R^2$, or an aromatic or heteroaromatic ring system having 5 to 60 aromatic ring atoms.

* * * * *